US008105828B2

(12) United States Patent
Owen, III et al.

(10) Patent No.: US 8,105,828 B2
(45) Date of Patent: Jan. 31, 2012

(54) STABLE CELL LINES AND METHODS FOR EVALUATING GASTROINTESTINAL ABSORPTION OF CHEMICALS

(75) Inventors: Albert J. Owen, III, West Chester, PA (US); Ismael J. Hidalgo, West Chester, PA (US); Jibin Li, West Chester, PA (US); Wei Zhang, Blackwood, NJ (US)

(73) Assignee: Absorption Systems Group, LLC, Exton, PA (US)

( * ) Notice: Subject to any disclaimer, the term of this patent is extended or adjusted under 35 U.S.C. 154(b) by 0 days.

(21) Appl. No.: 12/843,536

(22) Filed: Jul. 26, 2010

(65) Prior Publication Data

US 2010/0317049 A1    Dec. 16, 2010

Related U.S. Application Data

(62) Division of application No. 11/938,065, filed on Nov. 9, 2007, now Pat. No. 7,795,019.

(60) Provisional application No. 60/892,665, filed on Mar. 2, 2007, provisional application No. 60/857,938, filed on Nov. 10, 2006.

(51) Int. Cl.
*C07H 21/02* (2006.01)
*C07H 21/04* (2006.01)
*C12N 15/00* (2006.01)
*C12Q 1/68* (2006.01)

(52) U.S. Cl. .................... 435/325; 435/320.1; 536/23.1; 536/24.1; 536/24.5

(58) Field of Classification Search ........................ None
See application file for complete search history.

(56) References Cited

U.S. PATENT DOCUMENTS

| | | | |
|---|---|---|---|
| 5,872,014 A | 2/1999 | Sarkadi et al. | |
| 7,601,494 B2 | 10/2009 | Tian et al. | |
| 2005/0048464 A1 | 3/2005 | Tian et al. | |

FOREIGN PATENT DOCUMENTS

WO    WO 2006/021894    3/2006

OTHER PUBLICATIONS

Artursson et al., "Correlation between Oral Drug Absorption in Humans and Apparent Drug Permeability Coefficients in Human Intestinal Epithelial (Caco-2) Cells", Biochem. Biophys. Res. Commun., 1991, 175(3), 880-885.
Baker et al., "Novel Mechanisms for Antisense-Mediated Regulation of Gene Expression", Biochem. Biophys. Acta., 1999, 1489, 3-18.
Balimane et al., "Current Industrial Practices of Assessing Permeability and P-glycoprotein Interaction", AAPS J., 2006, 8, E1 -E13.
Bernstein et al., "Role for a Bidentate Ribonuclease in the Initiation Step of RNA Interference", Nature, 2001, 409(6818), 363-366.
Borst et al., "A Family of Drug Transporters: The Multidrug Resistance-associated Proteins", J. Natl. Cancer Inst., 2000, 92, 1295-1302.
Brummelkamp et al., "A System for Stable Expression of Short Interfering RNAs in Mammalian Cells", Science, Apr. 19, 2002, 296(5567), 550-553.
Celius et al., "Stable Supression of MDR1 Gene Expression and Function by RNAi in Caco-2 Cells", Biochem. Biophys. Res. Commun., 2004, 324, 365-371.
Cline et al., "Perspectives for Gene Therapy: Inserting new Genetic Information into Mammalian Cells by Physical Techniques and Viral Vectors", Pharmac. Ther., 1985, 29, 69-92.
Cotton et al., "Ribozyme Mediated Destruction of RNA in Vivo", EMBO J., 1989, 8(12), 3861-3866.
Denhardt, "Mechanism of Action of Antisense RNA: Sometime Inhibition of Transcription, Processing, Transport or Translation", Ann. N.Y. Acad. Sci., 1992, 660, 70-76.
Doyle et al., "A Multidrug Resistance Transporter from Human MCF-7 Breast Cancer Cells", Proc. Natl. Acad. Sci., USA, 1998, 95(26), 15665-15670.
Genbank Accession No. NM_004827, *Homo sapiens* ATP-Binding Cassette, Sub-Family Family B (MDR/TAP), Member 1 (ABCB1), mRNA, May 1, 2011, 7 pages.
Germann, "P-Glycoprotein: A Mediator of Multidrug Resistance in Tumor Cells", Eur. J. Cancer, 1996, 32A, 927-944.
Grishock et al., "Genes and Mechanisms related to RNA Interference Regulate Expression of the Small Temporal RNAs that Control *C. elegans* Developmental Timing", Cell, 2001, 106, 23-24.
Gutmann et al., "Evidence for Different ABC-Transporters in Caco-2 Cells Modulating Drug uptake", Pharm. Res. (NY), 1999, 16, 402-407.
Hirohashi et al., "Function and Expression of Multidrug Resistance-associated Protein Family in Human Colon Adenocarcinoma Cells (Caco-2)", J. Pharmacol. Exp.Ther., 2000, 292, 265-270.
Hunter et al., "Functional Expression of P-glycoprotein in Apical Membranes of Human Intestinal Caco-2 Cells. Kinetics of Vinblastine Secretion and Interaction with Modulators", J. Biol., Chem., 1993, 268(20), 14991-14997.
Hutvagner et al., "A Cellular Function for the RNA-Interference Enzyme Dicer in the Maturation of the let-7 small Temporal RNA", Science, 2001, 293, 834-838.
Jain, "RNAi and siRNA", Pharmacogenomics, 2004, 5(3), 239-242.
Ketting et al., "Dicer Functions in RNA Interference and in Synthesis of Small RNA involved in Developmental Timing in *C. elegans*", Genes Dev., 2001, 15(20), 2654-2659.
Lagos-Quintana et al., "Identification of Novel Genes Coding for Small expressed RNAs", Science, 2001, 294(5543), 853-858.
Lee et al., "siRNA—Getting the Message Out", European Journal of Pharmaceutical Sciences, Apr. 1, 2006, 27(5), 401-410.
Lee, "Mucosal Drug Delievery", J. Natl. Cancer Inst. Monogr., 2001, 29, 41-44.
McManus et al., "Gene Silencing using Micro-RNA Designed Hairpins", RNA, 2002, 8(6), 842-850.

(Continued)

*Primary Examiner* — Sean McGarry
(74) *Attorney, Agent, or Firm* — Woodcock Washburn LLP

(57) ABSTRACT

Nucleic acids and vectors for interfering with the expression of membrane efflux transport proteins in cells that express such proteins are provided. Also provided are cells and cell lines comprising such nucleic acids and vectors. Methods for screening chemicals and biomolecules for gastrointestinal absorption in animals, and kits for practicing such methods are also provided.

12 Claims, 14 Drawing Sheets

OTHER PUBLICATIONS

Miyagashi et al., "U6 Promoter-driven siRNAs with four uridine 3' Overhangs efficiently Suppress Targeted Gene Expression in Mammalian Cells", Nat. Biotech., 2002, 20(5), 497-500.

Mizuno et al., "Impact of Drug Transporter Studies on Drug Discovery and development", Pharmacological Rev., 2003, 55(3), 425-461.

Morris et al., "Lentivirus-Mediated RNA Interference Therapy for Human Immunodeficiency Virus Type 1 Infection", Human Gene Therapy, May 2006, 17(5), 479-486.

Neilsen, "Applications of Peptide Nucleic Acids", Curr. Opin. Biotech., 1999, 10, 71-75.

Nellen et al., "What Makes an mRNA Anti-Sense-itive?", Trends Biochem. Sci., 1993, 18(11), 419-423.

Paddison et al., "Short Hairpins RNA's (shRNAs) induce Sequence-Specific Silencing in Mammalian Cells", Genes and Dev., 2002, 16(8), 948-958.

Pasquinelli, "MicroRNAs: Deviants no Longer", Trends Gen., 2002, 18(4), 171-173.

Paul et al., "Effective Expression of Small Interfering RNA in Human Cells", Nat. Biotechnol., 2002, 20(5), 505-508.

Polli et al., (Borchardt, Ed.), "Pharmaceutical Profiling in Drug Discovery for Lead Selection", Am. Assoc. Pharm. Scientists, Arlington VA, 2004, 235-255.

Salphati et al., "Expression and Activity of the Efflux Transporters ABCB1, ABCC2 and ABCG2 in the Human Colorectal Carcinoma Cell Line LS513", European Journal of Pharmaceutical Sciences, Apr. 1, 2009, 463-468.

Staud et al., "Breast Cancer Resistance Protein (BCRP/ABCG2)", Int. J. Biochem. Cell Biol., 2005, 37(4), 720-725.

Stege et al., "Stable and Complete Overcoming of MDR1/P-glycoprotein Multidrug Resistance in Human Gastric Carcinoma Cells by RNA Interference", Cancer Gene Therapy, Jan. 28, 2004, 11(11), 699-706.

Stephens et al., "Kinetic Profiling of P-glycoprotein-mediated Drug Efflux in Rat an Humans Intestinal Epithelia", J. Pharmacol. Exp. Ther., 2001, 296(2), 584-591.

Sui et al., "DNA vector-based RNAi Technology to Suppress gene expression in Mammalian Cells", Proc. Natl. Acad. Sci., USA, 2002, 99(8), 5515-5520.

Troutman, "Novel Experimental Parameters to Quantify the Modulation of Absorptive and Secretory Transport of Compounds by P-glycoprotein in Cell Culture Models of Intestinal Epithelium", Pharm. Res., 2003, 20(8), 1210-1224.

Tuschl, Expanding Small RNA Interferences, Nat. Biotechnol., 2002, 20(5), 446-448.

U.S. Food and Drug Administration (FDA), "Drug Development and Drug Interactions", May 1, 2006, http://www.fda.gov/cder/druginteractions/default.htm.

Usman et al., "Hammerhead Ribozyme Engineering", Curr. Opin. Struct. Biol., 1996, 6(4), 527-533.

Van Asperen et al., "The Pharmacological Role of P-glycoprotein in the Intestinal Epithelium", Pharmacol. Res., 1998, 37(6), 429-435.

Van Breemen et al.,"Caco-2 Cells permeability Assays to measure Drug Absorption", Expert Opin. Drug Metab. Toxicol., 2005, 1(12), 175-185.

Varga et al., "Antisense Strategies: Functions and Applications in Immunology", Immun. Lett., 1999, 69(2), 217-224.

Wagner, "The State of the Art of Antisense research", Nat. Medicine, 1995, 1, 1116-1118.

Wakasugi et al., "Effect of the Clarithromycin on renal Excretion of Digoxin: Interaction with P-glycoprotein", Clin. Pharmacol., Ther., 1998, 64, 123-128.

Wang et al., "Evaluation of the MDR-MDCK Cell Line as a Permeability screen for the Blood-Brain Barrier", Int. J. Pharmaceutics, 2005, 288(2), 349-359.

Watanabe et al., "Construction of a Functional Transporter Analysis System Using MDR1 Knockdown Caco-2 Cells", Pharmaceutical Research, Aug. 1, 2005, 22(8), 1287-1293.

Waterhouse et al., "Virus Resistance and Gene Silencing in Plants can be Induced by Simultaneous Expression of Sense and Antisense RNA", Proc. Natl. Acad. Sci., USA, 1998, 95(23), 13959-13964.

Watson et al., "Functional Modeling of Tight Junctions in Intestinal Cell Monolayers Using Polyethylene glycol Oligomers", Am. J. Physiol. Cell Physiol., 2001, 281, C388-C397.

Weinstein et al. (Borchardt, Ed.,), "Pharmaceutical Profiling in Drug Discovery for Lead Selection", Am. Assoc. Pharm. Scientists, Arlington VA, 2004, 217-234.

Westphal et al., "Oral Bioavailability of Digoxin is Enhanced by Talinolol: Evidence for Involvement of Intestinal P-glycoprotein", Clin. Pharmacol. Ther., 2000, 68, 6-12.

Wiznerowicz et al., "Turning Silence: Conditional Systems for RNA Interference", Nature Methods, Sep. 2006, 3(9), 682-688.

Woolf, "The Stability, Toxicity and Effectiveness of Unmodified and Phosphorothioate Antisense Oligodeoxynucleotides in Xenopus Oocytes and Embryos", Nucleic Acids Res., 1990, 18(7), 1763-1769.

Wright et al., "Molecular and Cellular Physiology of Renal Organic Cation and Anion Transport", Phsyiol. Rev., 2004, 84(3), 897-1049.

Wu et al., "Small Interfering RNA-Induced Suppression of MDR1 (P-glycoprotein) Restores Sensitivity to Multidrug-resistance Cancer Cells", Cancer Res., 2003, 63(7), 1515-1519.

Xia et al., "Expression, Localization, and Functional Characteristics of Breast Cancer Resistance Protein in Caco-2 cells", Drug Metab. Dispos., 2005, 33(5), 637-643.

Yu et al., "RNA Interference by Expression of Short-Interfering RNA's and hairpin RNAs in Mammalian Cells", Proc. Natl. Acad. Sci., 2002, 99(9), 6047-6052.

Zeng et al., "Both Natural and Designed Micro RNAs can Inhibit the Expression of Cognate mRNAs when Expressed in Human Cells", Mol. Cell., 2002, 9(6), 1327-1333.

Zhang et al., "Scientific Perspectives on Drug transporters and their role in Drug Interactions", Molecular Pharmaceutics, 2006, 3, 62-69.

SEQUENCE LISTING

<160> NUMBER OF SEQ ID NOS: 27

<210> SEQ ID NO 1
<211> LENGTH: 58
<212> TYPE: DNA
<213> ORGANISM: Homo Sapiens

<400> SEQUENCE: 1
ccggccgaac acattggaag gaaatctcga gatttccttc caatgtgttc ggttttttg      58

<210> SEQ ID NO 2
<211> LENGTH: 58
<212> TYPE: DNA
<213> ORGANISM: Homo Sapiens

<400> SEQUENCE: 2
ccgggcagca attagaactg tgattctcga gaatcacagt tctaattgct gctttttg      58

<210> SEQ ID NO 3
<211> LENGTH: 58
<212> TYPE: DNA
<213> ORGANISM: Homo Sapiens

<400> SEQUENCE: 3
ccggcgacag aatagtaact tgtttctcga gaaacaagtt actattctgt cgttttttg      58

<210> SEQ ID NO 4
<211> LENGTH: 58
<212> TYPE: DNA
<213> ORGANISM: Homo Sapiens

<400> SEQUENCE: 4
ccgggctcat cgtttgtcta cagttctcga gaactgtaga caaacgatga gctttttg      58

<210> SEQ ID NO 5
<211> LENGTH: 58
<212> TYPE: DNA
<213> ORGANISM: Homo Sapiens

<400> SEQUENCE: 5
ccgggctgct ttcctgctga tctatctcga gatagatcag caggaaagca gctttttg      58

<210> SEQ ID NO 6
<211> LENGTH: 4872
<212> TYPE: DNA
<213> ORGANISM: Homo Sapiens

<400> SEQUENCE: 6
tattcagata ttctccagat tcctaaagat tagagatcat ttctcattct cctaggagta      60
ctcacttcag gaagcaacca gataaaagag aggtgcaacg gaagccagaa cattcctcct     120
ggaaattcaa cctgtttcgc agtttctcga ggaatcagca ttcagtcaat ccgggccggg     180
agcagtcatc tgtggtgagg ctgattggct gggcaggaac agcgccgggg cgtgggctga     240
gcacagccgc ttcgctctct tgccacagg aagcctgagc tcattcgagt agcggctctt      300
ccaagctcaa agaagcagag gccgctgttc gtttcctttta ggtctttcca ctaaagtcgg     360
agtatcttct tccaaaattt cacgtcttgg tggccgttcc aaggagcgcg aggtcggaat     420
ggatcttgaa ggggaccgca atggaggagc aaagaagaag aacttttttta aactgaacaa     480 taaaagtgaa aagataaga aggaaaagaa accaactgtc agtgtatttt caatgtttcg      540

```
ctattcaaat tggcttgaca agttgtatat ggtggtggga actttggctg ccatcatcca    600
tggggctgga cttcctctca tgatgctggt gtttggagaa atgacagata tctttgcaaa    660
tgcaggaaat ttagaagatc tgatgtcaaa catcactaat agaagtgata tcaatgatac    720
agggttcttc atgaatctgg aggaagacat gaccaggtat gcctattatt acagtggaat    780
tggtgctggg gtgctggttg ctgcttacat tcaggtttca ttttggtgcc tggcagctgg    840
aagacaaata cacaaaatta gaaacagtt ttttcatgct ataatgcgac aggagatagg    900
ctggtttgat gtgcacgatg ttggggagct taacacccga cttacagatg atgtctccaa    960
gattaatgaa ggaattggtg acaaaattgg aatgttcttt cagtcaatgg caacattttt   1020
cactgggttt atagtaggat ttacacgtgg ttggaagcta acccttgtga ttttggccat   1080
cagtcctgtt cttggactgt cagctgctgt ctgggcaaag atactatctt catttactga   1140
taaagaactc ttagcgtatg caaaagctgg agcagtagct gaagaggtct tggcagcaat   1200
tagaactgtg attgcatttg gaggacaaaa gaaagaactt gaaaggtaca acaaaaattt   1260
agaagaagct aaaagaattg ggataaagaa agctattaca gccaatattt ctataggtgc   1320
tgctttcctg ctgatctatg catcttatgc tctggccttc tggtatggga ccaccttggt   1380
cctctcaggg gaatattcta ttggacaagt actcactgta ttcttttctg tattaattgg   1440
ggcttttagt gttggacagg catctccaag cattgaagca tttgcaaatg caagaggagc   1500
agcttatgaa atcttcaaga taattgataa taagccaagt attgacagct attcgaagag   1560
tgggcacaaa ccagataata ttaagggaaa tttggaattc agaaatgttc acttcagtta   1620
cccatctcga aaagaagtta agatcttgaa gggtctgaac ctgaaggtgc agagtgggca   1680
gacggtggcc ctggttggaa acagtggctg tgggaagagc acaacagtcc agctgatgca   1740
gaggctctat gaccccacag aggggatggt cagtgttgat ggacaggata ttaggaccat   1800
aaatgtaagg tttctacggg aaatcattgg tgtggtgagt caggaacctg tattgtttgc   1860
caccacgata gctgaaaaca ttcgctatgg ccgtgaaaat gtcaccatgg atgagattga   1920
gaaagctgtc aaggaagcca atgcctatga ctttatcatg aaactgcctc ataaatttga   1980
caccctggtt ggagagagag gggcccagtt gagtggtggg cagaagcaga ggatcgccat   2040
tgcacgtgcc ctggttcgca accccaagat cctcctgctg gatgaggcca cgtcagcctt   2100
ggacacagaa agcgaagcag tggttcaggt ggctctggat aaggccagaa aaggtcggac   2160
caccattgtg atagctcatc gtttgtctac agttcgtaat gctgacgtca tcgctggttt   2220
cgatgatgga gtcattgtgg agaaaggaaa tcatgatgaa ctcatgaaag agaaaggcat   2280
ttacttcaaa cttgtcacaa tgcagacagc aggaaatgaa gttgaattag aaaatgcagc   2340
tgatgaatcc aaaagtgaaa ttgatgcctt ggaaatgtct tcaaatgatt caagatccag   2400
tctaataaga aaaagatcaa ctcgtaggag tgtccgtgga tcacaagccc aagacagaaa   2460
gcttagtacc aaagaggctc tggatgaaag tatacctcca gtttccttttt ggaggattat   2520
gaagctaaat ttaactgaat ggccttattt tgttgttggt gtattttgtg ccattataaa   2580
tggaggcctg caaccagcat ttgcaataat atttttcaaag attatagggg ttttacaag   2640
aattgatgat cctgaaacaa aacgacagaa tagtaacttg ttttcactat tgtttctagc   2700
ccttggaatt atttcttta ttacattttt ccttcagggt ttcacatttg gcaaagctgg   2760
agagatcctc accaagcggc tccgatacat ggttttccga tccatgctca gacaggatgt   2820
gagttggttt gatgacccta aaacaccac tggagcattg actaccaggc tcgccaatga   2880
tgctgctcaa gttaaagggg ctataggttc caggcttgct gtaattaccc agaatatagc   2940
```

| | |
|---|---|
| aaatcttggg acaggaataa ttatatcctt catctatggt tggcaactaa cactgttact | 3000 |
| cttagcaatt gtacccatca ttgcaatagc aggagttgtt gaaatgaaaa tgttgtctgg | 3060 |
| acaagcactg aaagataaga agaactaga aggttctggg aagatcgcta ctgaagcaat | 3120 |
| agaaaacttc cgaaccgttg tttctttgac tcaggagcag aagtttgaac atatgtatgc | 3180 |
| tcagagtttg caggtaccat acagaaactc tttgaggaaa gcacacatct ttggaattac | 3240 |
| attttccttc acccaggcaa tgatgtattt ttcctatgct ggatgtttcc ggtttggagc | 3300 |
| ctacttggtg gcacataaac tcatgagctt tgaggatgtt ctgttagtat tttcagctgt | 3360 |
| tgtctttggt gccatggccg tggggcaagt cagttcattt gctcctgact atgccaaagc | 3420 |
| caaaatatca gcagcccaca tcatcatgat cattgaaaaa accccttttga ttgacagcta | 3480 |
| cagcacggaa ggcctaatgc cgaacacatt ggaaggaaat gtcacatttg gtgaagttgt | 3540 |
| attcaactat cccacccgac cggacatccc agtgcttcag ggactgagcc tggaggtgaa | 3600 |
| gaagggccag acgctggctc tggtgggcag cagtggctgt gggaagagca cagtggtcca | 3660 |
| gctcctggag cggttctacg accccttggc agggaaagtg ctgcttgatg gcaaagaaat | 3720 |
| aaagcgactg aatgttcagt ggctccgagc acacctgggc atcgtgtccc aggagcccat | 3780 |
| cctgtttgac tgcagcattg ctgagaacat tgcctatgga gacaacagcc gggtggtgtc | 3840 |
| acaggaagag attgtgaggg cagcaaagga ggccaacata catgccttca tcgagtcact | 3900 |
| gcctaataaa tatagcacta agtaggaga caaaggaact cagctctctg gtggccagaa | 3960 |
| acaacgcatt gccatagctc gtgcccttgt tagacagcct catattttgc ttttggatga | 4020 |
| agccacgtca gctctggata cagaaagtga aaaggttgtc caagaagccc tggacaaagc | 4080 |
| cagagaaggc cgcaccctgca ttgtgattgc tcaccgcctg tccaccatcc agaatgcaga | 4140 |
| cttaatagtg gtgtttcaga atggcagagt caaggagcat ggcacgcatc agcagctgct | 4200 |
| ggcacagaaa ggcatctatt tttcaatggt cagtgtccag gctggaacaa agcgccagtg | 4260 |
| aactctgact gtatgagatg ttaaatactt tttaatattt gtttagatat gacatttatt | 4320 |
| caaagttaaa agcaaacact tacagaatta tgaagaggta tctgtttaac attcctcag | 4380 |
| tcaagttcag agtcttcaga gacttcgtaa ttaaaggaac agagtgagag acatcatcaa | 4440 |
| gtggagagaa atcatagttt aaactgcatt ataaatttta taacagaatt aaagtagatt | 4500 |
| ttaaagata aaatgtgtaa ttttgtttat attttcccat ttggactgta actgactgcc | 4560 |
| ttgctaaaag attatagaag tagcaaaaag tattgaaatg tttgcataaa gtgtctataa | 4620 |
| taaaactaaa ctttcatgtg actggagtca tcttgtccaa actgcctgtg aatatatctt | 4680 |
| ctctcaattg gaatattgta gataacttct gctttaaaaa agttttcttt aaatatacct | 4740 |
| actcattttt gtgggaatgg ttaagcagtt taaataattc ctgttgtata tgtctattca | 4800 |
| cattgggtct tacagaacca tctggcttca ttcttcttgg acttgatcct gctgattctt | 4860 |
| gcatttccac at | 4872 |

<210> SEQ ID NO 7
<211> LENGTH: 4868
<212> TYPE: DNA
<213> ORGANISM: Homo Sapiens

<400> SEQUENCE: 7

| | |
|---|---|
| gcggccgcgt ctttgttcca gacgcagtcc aggaatcatg ctggagaagt tctgcaactc | 60 |
| tacttttttgg aattcctcat tcctggacag tccggaggca gacctgccac tttgttttga | 120 |
| gcaaactgtt ctggtgtgga ttcccttggg cttcctatgg ctcctggccc cctggcagct | 180 |

-continued

```
tctccacgtg tataaatcca ggaccaagag atcctctacc accaaactct atcttgctaa     240
gcaggtattc gttggttttc ttcttattct agcagccata gagctggccc ttgtactcac     300
agaagactct ggacaagcca cagtccctgc tgttcgatat accaatccaa gcctctacct     360
aggcacatgg ctcctggttt tgctgatcca atacagcaga caatggtgtg tacagaaaaa     420
ctcctggttc ctgtccctat tctggattct ctcgatactc tgtggcactt tccaatttca     480
gactctgatc cggacactct tacagggtga caattctaat ctagcctact cctgcctgtt     540
cttcatctcc tacggattcc agatcctgat cctgatcttt tcagcatttt cagaaaataa     600
tgagtcatca aataatccat catccatagc ttcattcctg agtagcatta cctacagctg     660
gtatgacagc atcattctga aaggctacaa gcgtcctctg cactcgagg atgtctggga      720 agttgatgaa gagatgaaaa ccaagacatt agtgagcaag tttgaaacgc acatgaagag     780
agagctgcag aaagccaggc gggcactcca gagacggcag gagaagagct cccagcagaa     840
ctctggagcc aggctgcctg gcttgaacaa gaatcagagt caaagccaag atgcccttgt     900
cctggaagat gttgaaaaga aaaaaagaa gtctgggacc aaaaaagatg ttccaaaatc      960
ctggttgatg aaggctctgt tcaaaacttt ctacatggtg ctcctgaaat cattcctact     1020
gaagctagtg aatgacatct tcacgtttgt gagtcctcag ctgctgaaat tgctgatctc     1080
ctttgcaagt gaccgtgaca catatttgtg gattggatat ctctgtgcaa tcctcttatt     1140
cactgcggct ctcattcagt ctttctgcct tcagtgttat ttccaactgt gcttcaagct     1200
gggtgtaaaa gtacggacag ctatcatggc ttctgtatat aagaaggcat tgacccctatc    1260 caacttggcc aggaaggagt acaccgttgg agaaacagtg aacctgatgt ctgtggatgc     1320
ccagaagctc atggatgtga ccaacttcat gcacatgctg tggtcaagtg ttctacagat     1380
tgtcttatct atcttcttcc tatggagaga gttgggaccc tcagtcttag caggtgttgg     1440
ggtgatggtg cttgtaatcc caattaatgc gatactgtcc accaagagta agaccattca     1500
ggtcaaaaat atgaagaata agacaaacg tttaaagatc atgaatgaga ttcttagtgg      1560
aatcaagatc ctgaaatatt ttgcctggga accttcattc agagaccaag tacaaaacct     1620
ccggaagaaa gagctcaaga acctgctggc ctttagtcaa ctacagtgtg tagtaatatt     1680
cgtcttccag ttaactccag tcctggtatc tgtggtcaca ttttctgttt atgtcctggt     1740
ggatagcaac aatatttttgg atgcacaaaa ggccttcacc tccattaccc tcttcaatat    1800
cctgcgcttt cccctgagca tgcttcccat gatgatctcc tccatgctcc aggccagtgt     1860
ttccacagag cggctagaga agtacttggg agggatgac ttggacacat ctgccattcg      1920
acatgactgc aattttgaca aagccatgca gttttctgag gcctccttta cctgggaaca    1980
tgattcggaa gccacagtcc gagatgtgaa cctggacatt atggcaggcc aacttgtggc    2040
tgtgataggc cctgtcggct ctgggaaatc ctccttgata tcagccatgc tgggagaaat    2100
ggaaaatgtc cacgggcaca tcaccatcaa gggcaccact gcctatgtcc cacagcagtc    2160
ctggattcag aatggcacca taaggacaa catccttttt ggaacagagt taatgaaaa      2220 gaggtaccag caagtactgg aggcctgtgc tctcctccca gacttggaaa tgctgcctgg    2280
aggagatttg gctgagattg gagagaaggg tataaatctt agtggggtc agaagcagcg     2340 gatcagcctg gccagagcta cctaccaaaa tttagacatc tatcttctag atgacccct     2400 gtctgcagtg gatgctcatg taggaaaaca tatttttaat aaggtcttgg gccccaatgg    2460
cctgttgaaa ggcaagactc gactcttggt tacacatagc atgcactttc ttcctcaagt    2520
ggatgagatt gtagttctgg ggaatggaac aattgtagag aaaggatcct acagtgctct    2580
```

-continued

| | |
|---|---|
| cctggccaaa aaaggagagt tgctaagaa tctgaagaca tttctaagac atacaggccc | 2640 |
| tgaagaggaa gccacagtcc atgatggcag tgaagaagaa gacgatgact atgggctgat | 2700 |
| atccagtgtg aaagagatcc ccgaagatgc agcctccata accatgagaa gagagaacag | 2760 |
| ctttcgtcga acacttagcc gcagttctag gtccaatggc aggcatctga agtccctgag | 2820 |
| aaactccttg aaaactcgga atgtgaatag cctgaaggaa gacgaagaac tagtgaaagg | 2880 |
| acaaaaacta attaagaagg aattcataga aactggaaag gtgaagttct ccatctacct | 2940 |
| ggagtaccta caagcaatag gattgttttc gatattcttc atcatccttg cgtttgtgat | 3000 |
| gaattctgtg gcttttattg gatccaacct ctggctcagt gcttggacca gtgactctaa | 3060 |
| aatcttcaat agcaccgact atccagcatc tcagagggac atgagagttg agtctacgg | 3120 |
| agctctggga ttagcccaag gtatatttgt gttcatagca catttctgga gtgcctttgg | 3180 |
| tttcgtccat gcatcaaata tcttgcacaa gcaactgctg aacaatatcc ttcgagcacc | 3240 |
| tatgagattt tttgacacaa cacccacagg ccggattgtg aacaggtttg ccggcgatat | 3300 |
| ttccacagtg gatgacaccc tgcctcagtc cttgcgcagc tggattacat gcttcctggg | 3360 |
| gataatcagc acccttgtca tgatctgcat ggccactcct gtcttcacca tcatcgtcat | 3420 |
| tcctcttggc attatttatg tatctgttca gatgttttat gtgtctacct cccgccagct | 3480 |
| gaggcgtctg gactctgtca ccaggtcccc aatctactct cacttcagcg agaccgtatc | 3540 |
| aggtttgcca gttatccgtg cctttgagca ccagcagcga tttctgaaac acaatgaggt | 3600 |
| gaggattgac accaaccaga aatgtgtctt ttcctggatc acctccaaca ggtggcttgc | 3660 |
| aattcgcctg gagctggttg ggaacctgac tgtcttcttt tcagccttga tgatggttat | 3720 |
| ttatagagat acccctaagtg gggacactgt tggctttgtt ctgtccaatg cactcaatat | 3780 |
| cacacaaacc ctgaactggc tggtgaggat gacatcagaa atagagacca acattgtggc | 3840 |
| tgttgagcga ataactgagt acacaaaagt ggaaaatgag gcaccctggg tgactgataa | 3900 |
| gaggcctccg ccagattggc ccagcaaagg caagatccag tttaacaact accaagtgcg | 3960 |
| gtaccgacct gagctggatc tggtcctcag agggatcact tgtgacatcg gtagcatgga | 4020 |
| gaagattggt gtggtgggca ggacaggagc tggaaagtca tccctcacaa actgcctctc | 4080 |
| cagaatctta gaggctgccg gtggtcagat tatcattgat ggagtagata ttgcttccat | 4140 |
| tgggctccac gacctccgag agaagctgac catcatcccc caggacccca tcctgttctc | 4200 |
| tggaagcctg aggatgaatc tcgaccctttt caacaactac tcagatgagg agatttggaa | 4260 |
| ggccttggag ctggctcacc tcaagtctttt tgtggccagc ctgcaacttg ggttatccca | 4320 |
| cgaagtgaca gaggctggtg gcaacctgag cataggccag aggcagctgc tgtgcctggg | 4380 |
| cagggctctg cttcggaaat ccaagatcct ggtcctggat gaggccactg ctgcggtgga | 4440 |
| tctagagaca gacaacctca ttcagacgac catccaaaac gagttcgccc actgcacagt | 4500 |
| gatcaccatc gcccacaggc tgcacaccat catggacagt gacaaggtaa tggtcctaga | 4560 |
| caacgggaag attatagagt gcggcagccc tgaagaactg ctacaaatcc ctggacccctt | 4620 |
| ttactttatg gctaaggaag ctggcattga gaatgtgaac agcacaaaat tctagcagaa | 4680 |
| ggccccatgg gttagaaaag gactataaga ataatttctt atttaatttt attttttata | 4740 |
| aaatacagaa tacatacaaa agtgtgtata aaatgtacgt tttaaaaaag gataagtgaa | 4800 |
| cacccatgaa cctactaccc aggttaagaa aataaatgtc accaggtact tgagaaaccc | 4860 |
| ctcgattg | 4868 |

<210> SEQ ID NO 8

```
<211> LENGTH: 4445
<212> TYPE: DNA
<213> ORGANISM: Homo Sapiens

<400> SEQUENCE: 8
gtcagcgctg cctgagctcg tccctggat gtccgggtct ccccaggcgg ccacccgccg      60
gctcccatcg tgacctccag ccgcagcgcc tcccacgccg gccgccgcgc gaggggagcg     120
ctcgggcgcg ccgggtgtgg ttgggggaag gggttgtgcc gcgcgcgggc tgcgtgctgt     180
gcccactcaa aaggttccgg gcgcgcagga gggaagaggc agtgcccgcc actcccactg     240
agattgagag acgcggcaag gaggcagcct gtggaggaac tgggtaggat ttaggaacgc     300
accgtgcaca tgcttggtgg tcttgttaag tggaaactgc tgctttagag tttgtttgga     360
aggtccgggt gactcatccc aacatttaca tccttaattg ttaaagcgct gcctccgagc     420
gcacgcatcc tgagatcctg agcctttggt taagaccgag ctctattaag ctgaaaagat     480
aaaaactctc cagatgtctt ccagtaatgt cgaagttttt atcccagtgt cacaaggaaa     540
caccaatggc ttccccgcga cagcttccaa tgacctgaag gcatttactg aaggagctgt     600
gttaagtttt cataacatct gctatcgagt aaaactgaag agtggctttc taccttgtcg     660
aaaaccagtt gagaaagaaa tattatcgaa tatcaatggg atcatgaaac tggtctcaa      720 cgccatcctg ggacccacag gtggaggcaa atcttcgtta ttagatgtct tagctgcaag     780
gaaagatcca agtggattat ctggagatgt tctgataaat ggagcaccgc gacctgccaa     840
tttcaaatgt aattcaggtt acgtggtaca agatgatgtt gtgatgggca ctctgacggt     900
gagagaaaac ttacagttct cagcagctct tcggcttgca caactatga cgaatcatga     960 aaaaaacgaa cggattaaca gggtcattca agagttaggt ctggataaag tggcagactc    1020
caaggttgga actcagttta ccgtggtgt gtctggagga gaaagaaaa ggactagtat    1080 aggaatggag cttatcactg atccttccat cttgttcttg gatgagccta caactggctt    1140
agactcaagc acagcaaatg ctgtccttt gctcctgaaa aggatgtcta agcagggacg    1200
aacaatcatc ttctccattc atcagcctcg atattccatc ttcaagttgt ttgatagcct    1260
caccttattg gcctcaggaa gacttatgtt ccacgggcct gctcaggagg ccttgggata    1320
ctttgaatca gctggttatc actgtgaggc ctataataac cctgcagact tcttcttgga    1380
catcattaat ggagattcca ctgctgtggc attaaacaga gaagaagact ttaaagccac    1440
agagatcata gagccttcca agcaggataa gccactcata gaaaattag cggagattta    1500 tgtcaactcc tccttctaca aagagacaaa agctgaatta catcaacttt ccggggtga    1560 gaagaagaag aagatcacag tcttcaagga gatcagctac accacctcct tctgtcatca    1620
actcagatgg gtttccaagc gttcattcaa aaacttgctg ggtaatcccc aggcctctat    1680
agctcagatc attgtcacag tcgtactggg actggttata ggtgccattt actttgggct    1740
aaaaaatgat tctactggaa tccagaacag agctggggtt ctcttcttcc tgacgaccaa    1800
ccagtgtttc agcagtgttt cagccgtgga actctttgtg gtagagaaga agctcttcat    1860
acatgaatac atcagcggat actacagagt gtcatcttat ttccttggaa aactgttatc    1920
tgatttatta cccatgagga tgttaccaag tattatattt acctgtatag tgtacttcat    1980
gttaggattg aagccaaagg cagatgcctt cttcgttatg atgtttaccc ttatgatggt    2040
ggcttattca gccagttcca tggcactggc catagcagca ggtcagagtg tggtttctgt    2100
agcaacactt ctcatgacca tctgtttgt gtttatgatg atttttcag gtctgttggt    2160 caatctcaca accattgcat cttggctgtc atggcttcag tacttcagca ttccacgata    2220
```

-continued

```
tggatttacg gctttgcagc ataatgaatt tttgggacaa aacttctgcc caggactcaa    2280
tgcaacagga aacaatcctt gtaactatgc aacatgtact ggcgaagaat atttggtaaa    2340
gcagggcatc gatctctcac cctggggctt gtggaagaat cacgtggcct tggcttgtat    2400
gattgttatt ttcctcacaa ttgcctacct gaaattgtta tttcttaaaa aatattctta    2460
aatttcccct taattcagta tgatttatcc tcacataaaa aagaagcact ttgattgaag    2520
tattcaatca agttttttg ttgttttctg ttcccttgcc atcacactgt tgcacagcag     2580
caattgtttt aaagagatac attttagaa atcacaacaa actgaattaa acatgaaaga    2640
acccaagaca tcatgtatcg catattagtt aatctcctca gacagtaacc atggggaaga    2700
aatctggtct aatttattaa tctaaaaaag gagaattgaa ttctggaaac tcctgacaag    2760
ttattactgt ctctggcatt tgtttcctca tctttaaaat gaataggtag gttagtagcc    2820
cttcagtctt aatactttat gatgctatgg tttgccatta tttaataaat gacaaatgta    2880
ttaatgctat actggaaatg taaaattgaa aatatgttgg aaaaaagatt ctgtcttata    2940
gggtaaaaaa agccaccgtg atagaaaaaa aatcttttg ataagcacat taaagttaat     3000
agaacttact gatattcctg tctagtggta taatatctca ggaatcttgg ctgagggttt    3060
ggaactgtgg gtagagtaga gggccaggag tccagtaata gaattcttgc accatttctg    3120
gaacattcta gctctgggag gtcacgtaac cttcttgggg tagttcagtg gtttagtggt    3180
ttataatcca ggtgtgcgtc agaatcatct gaggaacttt gctaaaatac aaaaatctgg    3240
cctaagtagc tccagatcta ccttcataaa ggaatctgac cactcctgga tttggtaatt    3300
tccaagttct gaaaatttta cttaggattt aataactatt aacatctgtc cctacatagg    3360
ttttctttcc tacttatata ccttatgttc tcttcattct aaccttcatc agtaataggg    3420
aaatgtttta attttatttt tttagttgaa gggtaatgta ccaaaaaata tagttcagtg    3480
aattaaaatg aacacacatg tgcaaccatc aattcaggtc aagaaataga agattgtagc    3540
acacaaaagc ctactcagcc attctcccag tcactacttc cttccttacc cctgggttat    3600
ttttgaaatg acacttgatg tatttccctc tgttgctgtt atgagaacat tgctacagcc    3660
aagtgttgtg tttctgtgtg cataggttga tacttaatta tctccccact ttttaataaa    3720
cttttaattt ggaataatt ttagattgac agaaagttg caaagatagt gaggaaagtt      3780
cctgtctact ctttgctcag cttcccttaa tgttaacatt ttatatagca agatgcattt    3840
gtcaaagcta acaagttaac attggtacaa tcactgttaa ttaaactgca cacaatattc    3900
agatttcacc acttttccac taatattctt tcattgttct aggattcaat tcaggagacc    3960
acatttcatc tagccctctt ttttaaaagt aaatactttt cagcacttac aggagttaac    4020
tgagctgggg catcatggtg tatagacgcc ctgacactgg tcatcttgga attcatttag    4080
tttgtcagtg ggtgccctga cattctgtca caacatcaat ttgggaacat ggcattatat    4140
ttttatcttt gaactttttt ctttttggat gacatttgat taatgcgtca tcttggaaca    4200
cattatcttt tttcttggtt atgtgatcag gaagattaat cagttttcc tgttcttggt     4260 ataattcctg ctttcacat acctgtccct tacagttctc tatatatacc cttcccttat     4320
tacacagaga gaaatatcta tctatacttt ttacacaaaa tatacttcaa aagaaacaaa    4380
acagccacaa ttattaactt tttaaataaa tgagaattta attatatcct aaaaaaaaaa    4440
aaaaa                                                                4445
```

<210> SEQ ID NO 9
<211> LENGTH: 20
<212> TYPE: DNA

```
<213> ORGANISM: Homo Sapiens

<400> SEQUENCE: 9
gctcctgact atgccaaagc                                                  20

<210> SEQ ID NO 10
<211> LENGTH: 20
<212> TYPE: DNA
<213> ORGANISM: Homo Sapiens

<400> SEQUENCE: 10
tcttcacctc caggctcagt                                                  20

<210> SEQ ID NO 11
<211> LENGTH: 20
<212> TYPE: DNA
<213> ORGANISM: Homo Sapiens

<400> SEQUENCE: 11
ctggttggga acctgactgt                                                  20

<210> SEQ ID NO 12
<211> LENGTH: 20
<212> TYPE: DNA
<213> ORGANISM: Homo Sapiens

<400> SEQUENCE: 12
caacagccac aatgttggtc                                                  20

<210> SEQ ID NO 13
<211> LENGTH: 20
<212> TYPE: DNA
<213> ORGANISM: Homo Sapiens

<400> SEQUENCE: 13
gtggccttgg cttgtatgat                                                  20

<210> SEQ ID NO 14
<211> LENGTH: 20
<212> TYPE: DNA
<213> ORGANISM: Homo Sapiens

<400> SEQUENCE: 14
gatggcaagg gaacagaaaa                                                  20

<210> SEQ ID NO 15
<211> LENGTH: 21
<212> TYPE: DNA
<213> ORGANISM: Homo Sapiens

<400> SEQUENCE: 15
actatcggca atgagcggtt c                                                21

<210> SEQ ID NO 16
<211> LENGTH: 21
<212> TYPE: DNA
<213> ORGANISM: Homo Sapiens

<400> SEQUENCE: 16
agagccacca atccacacag a                                                21

<210> SEQ ID NO 17
<211> LENGTH: 58
<212> TYPE: DNA
```

<213> ORGANISM: Homo Sapiens

<400> SEQUENCE: 17
ccggcgtgta taaatccagg accaactcga gttggtcctg gatttataca cgttttttg    58

<210> SEQ ID NO 18
<211> LENGTH: 58
<212> TYPE: DNA
<213> ORGANISM: Homo Sapiens

<400> SEQUENCE: 18
ccggcctggt ggatagcaac aatatctcga gatattgttg ctatccacca ggttttttg    58

<210> SEQ ID NO 19
<211> LENGTH: 58
<212> TYPE: DNA
<213> ORGANISM: Homo Sapiens

<400> SEQUENCE: 19
ccgggcatct gaagtccctg agaaactcga gtttctcagg gacttcagat gcttttttg    58

<210> SEQ ID NO 20
<211> LENGTH: 58
<212> TYPE: DNA
<213> ORGANISM: Homo Sapiens

<400> SEQUENCE: 20
ccgggccggt ggtcagatta tcattctcga gaatgataat ctgaccaccg gcttttttg    58

<210> SEQ ID NO 21
<211> LENGTH: 58
<212> TYPE: DNA
<213> ORGANISM: Homo Sapiens

<400> SEQUENCE: 21
ccggccatag cttcattcct gagtactcga gtactcagga atgaagctat ggttttttg    58

<210> SEQ ID NO 22
<211> LENGTH: 58
<212> TYPE: DNA
<213> ORGANISM: Homo Sapiens

<400> SEQUENCE: 22
ccgggcctcg atattccatc ttcaactcga gttgaagatg aatatcgag gcttttttg     58

<210> SEQ ID NO 23
<211> LENGTH: 58
<212> TYPE: DNA
<213> ORGANISM: Homo Sapiens

<400> SEQUENCE: 23
ccgggcaaca actatgacga atcatctcga gatgattcgt catagttgtt gcttttttg    58

<210> SEQ ID NO 24
<211> LENGTH: 58
<212> TYPE: DNA
<213> ORGANISM: Homo Sapiens

<400> SEQUENCE: 24
ccggccttct tcgttatgat gtttactcga gtaaacatca taacgaagaa ggttttttg    58

<210> SEQ ID NO 25
<211> LENGTH: 58
<212> TYPE: DNA

```
<213> ORGANISM: Homo Sapiens

<400> SEQUENCE: 25
ccgggctgtg gcattaaaca gagaactcga gttctctgtt taatgccaca gcttttttg        58

<210> SEQ ID NO 26
<211> LENGTH: 58
<212> TYPE: DNA
<213> ORGANISM: Homo Sapiens

<400> SEQUENCE: 26
ccggcctgcc aatttcaaat gtaatctcga gattacattt gaaattggca ggtttttg         58

<210> SEQ ID NO 27
<211> LENGTH: 57
<212> TYPE: DNA
<213> ORGANISM: Homo Sapiens

<400> SEQUENCE: 27
ccggcaacaa gatgaagagc accaactcga gttggtgctc ttcatcttgt tgtttttt        57
```

STABLE CELL LINES AND METHODS FOR EVALUATING GASTROINTESTINAL ABSORPTION OF CHEMICALS

CROSS-REFERENCE TO RELATED APPLICATIONS

This application is a divisional of U.S. patent application Ser. No. 11/938,065, filed Nov. 9, 2007, now allowed, which claims the benefit of U.S. Provisional Application No. 60/892,665, filed Mar. 2, 2007, and of U.S. Provisional Application No. 60/857,938, filed Nov. 10, 2006, all of which are incorporated by reference herein.

FIELD

The invention relates generally to the field of pharmacology. More specifically, the invention features stable cell lines, kits, and methods for predicting the absorption of chemicals such as drugs, nutritional supplements, and environmental chemicals upon administration to animals or humans.

BACKGROUND

Various publications, including patents, published applications, technical articles and scholarly articles are cited throughout the specification. Each of these cited publications is incorporated by reference herein, in its entirety and for all purposes.

Drug absorption is the sum total of the effects of various mechanisms by which drugs pass from the point of entry into the bloodstream. The rate and efficiency of drug absorption affects the rate and extent to which a drug reaches its intended site of action. Gastrointestinal absorption of orally administered drugs is, in part, a function of the permeability of mucosa in the gastrointestinal tract, particularly in the intestines, and also, in part, a function of the transit rate through the various organs of the gastrointestinal tract as the transit rate establishes the length of time the drug is localized to an absorption site.

Intestinal absorption of drugs can occur via different routes. Many orally administered drugs are absorbed by passive transcellular diffusion through the cell membrane of enterocytes (Van Asperen J et al. (1998) Pharm. Res. 37:429-35) or by passive paracellular diffusion through the tight junctions in the intestinal epithelium (Watson C J et al. (2001) Am. J. Physiol. Cell Physiol. 281:C388-C397). Epithelial drug absorption is also mediated by membrane transport proteins (Lee V H (2001) J. Natl. Cancer Inst. Monogr. 29:41-4). Such transport proteins can also serve as an impediment to drug absorption.

Various efflux transporters have been described, including members of the multidrug resistance protein (MRP) family (Borst P et al. (2000) J. Natl. Cancer Inst. 92:1295-1302), P-glycoprotein (P-gp) (Germann U A (1996) Eur. J. Cancer 32A:927-44), and breast cancer resistance protein (BCRP) (Staud F et al. (2005) Int. J. Biochem. Cell Biol. 374:720-5; Doyle L A et al. (1998) Proc. Natl. Acad. Sci. USA. 9526:15665-70), among others. Such efflux transport proteins are believed to be primarily responsible for low or variable absorption of orally administered drugs (Stephens R H et al. (2001) J. Pharmacol. Exp. Ther. 296:584-91).

Drug absorption and the factors that facilitate or impede it are thus important considerations in drug design and the evaluation of lead compounds as potential therapeutic agents. Several models are available for assessing absorption in the intestine. These models include the parallel artificial membrane permeability assay (PAMPA), in situ intestinal recirculating and single-pass perfusion, Ussing chambers, and cell lines, including Madin-Darby canine kidney cells (MDCK), and Caco-2 cells (Balimane P V et al. (2006) AAPS J. 8:E1-13).

Caco-2 cells, which were derived from a human colon adenocarcinoma, are a widely used model for intestinal absorption studies. When grown and allowed to differentiate, Caco-2 cells are morphologically similar to enterocytes and express many of the enzymes present in the small intestinal brush border, and thus closely resemble the environment and functions of the small intestine. Caco-2 cells provide an additional advantage for intestinal absorption studies in that they express at least three drug efflux transporter proteins, including P-gp (Hunter J et al. (1993) J. Biol. Chem. 268:14991-7), MRP proteins (Hirohashi T et al. (2000) J. Pharmacol. Exp. Ther. 292:265-70; Gutmann H et al. (1999) Pharm. Res. (NY) 16:402-7), and BCRP (Xia C Q et al. (2005) Drug Metab. Dispos. 33:637-43).

For drug absorption studies, it is desirable to evaluate the contributions of drug efflux transport proteins to impaired absorption. This can be accomplished by inhibiting the expression or activity of the transporters, particularly P-gp. In general, chemicals such as cyclosporine A are used to block the activity of P-gp. Chemical inhibition of transporters presents a disadvantage insofar as such chemicals also inhibit other cellular proteins and functions, and thus can skew the results of absorption experiments. Recently, the expression of P-gp in Caco-2 cells was shown to be reduced using RNAi technology (Watanabe T et al. (2005) Pharm. Res. 22:1287-93), and the expression of multidrug resistant gene 1 (MDR1) in Caco-2 cells was shown to be reduced using RNAi technology (Celius T et al. (2004) Biochem. Biophys. Res. Comm. 324:365-71). Inhibition of P-gp expression by RNAi enhanced the intracellular accumulation of and restored the sensitivity to compounds transported by P-gp (Wu H et al. (2003) Cancer Res. 63:1515-19). While genetically downregulating P-gp in Caco-2 cells represents an improvement over the use of chemical inhibitors, studies of drug absorption in this model are disadvantaged in that the knockdown of P-gp expression alone does not account for contributions of extant transporters such as MRP and BCRP to drug efflux and impaired absorption. In addition, shRNA synthesized in vitro and directly transfected into cells reduces gene expression only transiently, and expression is restored a few days after transfection. Moreover, in vitro-synthesized shRNA is also often limited to cells that are easily transfected, and very little is known about the stability of inhibition of gene expression after several cell passages.

To accurately evaluate and predict the intestinal absorption of lead compounds, it is desired that the relative contributions of any and all efflux transport proteins be accounted for and controlled. Similarly, it is desirable to produce and utilize stable cell lines to genetically control the expression and/or function of such transport proteins on a more permanent basis. The present invention addresses these long-felt needs.

SUMMARY

The invention features isolated nucleic acid molecules for inhibiting expression of at least one membrane efflux transport protein, the nucleic acid molecule comprising the nucleotide sequence of SEQ ID NO: 1, 2, 3, 4, 5, 17, 18, 19, 20, 21, 22, 23, 24, 25, or 26 or allelic variants thereof. The nucleic acid molecules can be single, double, or triple stranded. In some preferred aspects, the nucleic acid molecules are RNA.

Vectors comprising nucleic acid sequences encoding a nucleic acid molecule for inhibiting expression of a membrane efflux transport protein, wherein said nucleic acid molecule comprises SEQ ID NO: 1, 2, 3, 4, 5, 17, 18, 19, 20, 21, 22, 23, 24, 25, or 26, or allelic variants thereof are also provided. In the vectors, the nucleic acid molecule can be operably linked to one or more regulatory elements such as an inducible or constitutive promoter. The vectors can be viral vectors, and in some preferred embodiments are lentivirus vectors.

Host cells transformed with such vectors are also provided by this invention. It is preferred that such host cells chosen for transformation with the vectors express at least one membrane efflux transport protein such that transformation will result in inhibition of the expression of the protein. The membrane efflux transport protein can be any such protein. Examples of membrane efflux transport proteins include P-glycoprotein, Multidrug Resistance-Associated Protein 2, and Breast Cancer Resistance Protein. Host cells can be epithelial cells, and are preferably intestinal epithelial cells, and are more preferably human intestinal epithelial cells. Examples of suitable cells include Caco-2 cells, C2BBe1 cells, HT-29 cells, and T-84 cells. Host cell cultures are also provided.

Also featured are methods for screening compounds for gastrointestinal absorption in an animal such as a human comprising stably inhibiting the expression of at least one membrane efflux transport protein in a cell, contacting the cell with a test compound, measuring transcellular transport of the test compound, and comparing the transcellular transport measurements with reference values for transcellular transport of compounds with no gastrointestinal absorption, low gastrointestinal absorption, moderate gastrointestinal absorption, or high gastrointestinal absorption. The measurements relative to the reference values are indicative of the gastrointestinal absorption of the compound in the body of the animal Examples of membrane efflux transport proteins include P-glycoprotein, Multidrug Resistance-Associated Protein 2, and Breast Cancer Resistance Protein.

In such methods, the inhibiting can comprise stably transforming the cell with a nucleic acid molecule that interferes with the expression of the at least one membrane efflux transport protein. Examples of suitable cells include Caco-2 cells, C2BBe1 cells, HT-29 cells, and T-84 cells. Suitable nucleic acid molecules include those having SEQ ID NO: 1, 2, 3, 4, 5, 17, 18, 19, 20, 21, 22, 23, 24, 25, or 26, and conservatively modified variants or allelic variants thereof. One non-limiting example of stable transformation involves the use of viral, and preferably lentiviral vectors that comprise the nucleic acid molecule. In some aspects, a single nucleic acid molecule can inhibit the expression of two or more membrane efflux transport proteins.

Also featured are methods for screening compounds for gastrointestinal absorption in an animal such as a human comprising stably inhibiting the expression of a first membrane efflux transport protein in a cell, stably inhibiting the expression of a second membrane efflux transport protein in a second cell, contacting the first and second cells with a test compound, measuring transcellular transport of the test compound in the first and second cells, and comparing the transcellular transport measurements with reference values for transcellular transport of compounds with no gastrointestinal absorption, low gastrointestinal absorption, moderate gastrointestinal absorption, or high gastrointestinal absorption. In some embodiments, the methods further comprise stably inhibiting the expression of a third membrane efflux transport protein in a third cell, contacting the first, second, and third cells with a test compound, measuring transcellular transport of the test compound in the first, second, and third cells, and comparing the transcellular transport measurements with reference values for transcellular transport of compounds with no gastrointestinal absorption, low gastrointestinal absorption, moderate gastrointestinal absorption, or high gastrointestinal absorption. For each comparison, the measurements indicate the relative contribution of the first, second, and third membrane efflux transport protein to transcellular transport of the test compound, and the measurements relative to the reference values are predictive of the gastrointestinal absorption of the compound in the body of the animal. Examples of membrane efflux transport proteins include P-glycoprotein, Multidrug Resistance-Associated Protein 2, and Breast Cancer Resistance Protein.

In such methods, the inhibition of the first, second, and/or third membrane efflux transport protein can comprise transforming the cell with a nucleic acid molecule that interferes with the expression of the at least one membrane efflux transport protein. Examples of suitable cells include Caco-2 cells, C2BBe1 cells, HT-29 cells, and T-84 cells. Suitable nucleic acid molecules include those having SEQ ID NO: 1, 2, 3, 4, 5, 17, 18, 19, 20, 21, 22, 23, 24, 25, or 26, and conservatively modified variants or allelic variants thereof. One non-limiting example of stable inhibition involves the use of viral, and preferably lentiviral vectors that comprise the nucleic acid molecule. In some aspects, a single nucleic acid molecule can inhibit the expression of two or more membrane efflux transport proteins.

The invention also provides methods for inhibiting the expression of a membrane efflux transport protein. The methods comprise stably transforming a cell with a vector comprising a nucleic acid sequence encoding a nucleic acid molecule that interferes with the expression of a membrane efflux transport protein, and expressing said nucleic acid molecule in the cell, wherein expression of the nucleic acid molecule inhibits the expression of the membrane efflux transport protein. Lentivirus vectors are preferred. The membrane efflux transport protein can be P-glycoprotein, Multidrug Resistance-Associated Protein 2, or Breast Cancer Resistance Protein. The nucleic acid sequence can comprise SEQ ID NO: 1, 2, 3, 4, 5, 17, 18, 19, 20, 21, 22, 23, 24, 25, or 26, or conservatively modified variants or allelic variants thereof. One non-limiting example of stable transformation involves the use of viral, and preferably lentiviral vectors that comprise the nucleic acid molecule. In some aspects, a single nucleic acid molecule can inhibit the expression of two or more membrane efflux transport proteins.

Kits for screening compounds for gastrointestinal absorption in animals are provided by the invention. In some embodiments, such kits can comprise, in one or more containers, a cell stably transformed with at least one nucleic acid molecule for inhibiting expression of at least one membrane efflux transport protein and instructions for using the kit in a method for screening compounds for gastrointestinal absorption in animals. The kits can further comprise additional cells stably transformed with a nucleic acid molecule that interferes with the expression of additional membrane efflux transport protein. Examples of membrane efflux transport proteins include P-glycoprotein, Multidrug Resistance-Associated Protein 2, and Breast Cancer Resistance Protein. Examples of suitable cells include Caco-2 cells, C2BBe1 cells, HT-29 cells, and T-84 cells. Suitable nucleic acid molecules include those having SEQ ID NO: 1, 2, 3, 4, 5, 17, 18, 19, 20, 21, 22, 23, 24, 25, or 26, and conservatively modified variants or allelic variants thereof.

The invention also features methods for identifying compounds that inhibit the efflux activity of a membrane efflux transport protein. Such methods, in some embodiments, comprise stably inhibiting the expression of a membrane efflux transport protein in a first cell, contacting the first cell with a substrate of the membrane efflux transport protein, contacting a second cell expressing the membrane efflux transport protein with a test compound and a substrate of the membrane efflux transport protein, determining the efflux activity of the membrane efflux transport protein in the first cell, and in the second cell in the presence and absence of the test compound, and comparing the determined efflux activities, wherein a decrease in the efflux activity in the presence of the test compound relative to the efflux activity in the absence of the test compound, and at least partial identity of the efflux activity in the presence of the test compound with the efflux activity in the first cell indicates that the test compound specifically inhibits the membrane efflux transport protein.

In such methods, the stable inhibition of the membrane efflux transport protein in the first cell can comprise transforming the cell with a nucleic acid molecule that interferes with the expression of the at least one membrane efflux transport protein. Examples of membrane efflux transport proteins include P-glycoprotein, Multidrug Resistance-Associated Protein 2, and Breast Cancer Resistance Protein. Suitable nucleic acid molecules include those having SEQ ID NO: 1, 2, 3, 4, 5, 17, 18, 19, 20, 21, 22, 23, 24, 25, or 26, and conservatively modified variants or allelic variants thereof. Examples of cells that can serve as the first and/or second cell include Caco-2 cells, C2BBe1 cells, HT-29 cells, and T-84 cells. One non-limiting example of stable inhibition involves the use of viral, and preferably lentiviral vectors that comprise the nucleic acid molecule. In some aspects, a single nucleic acid molecule can inhibit the expression of two or more membrane efflux transport proteins.

Any known substrate of the membrane efflux transport protein of interest can be used in the methods. Examples of such substrates include digoxin for P-glycoprotein, vinblastine or dinitrophenyl-5-glutathione for Multidrug Resistance-Associated Protein 2, and mitoxantrone or estrone-3-sulfate for Breast Cancer Resistance Protein.

DETAILED DESCRIPTION

Figure 1:
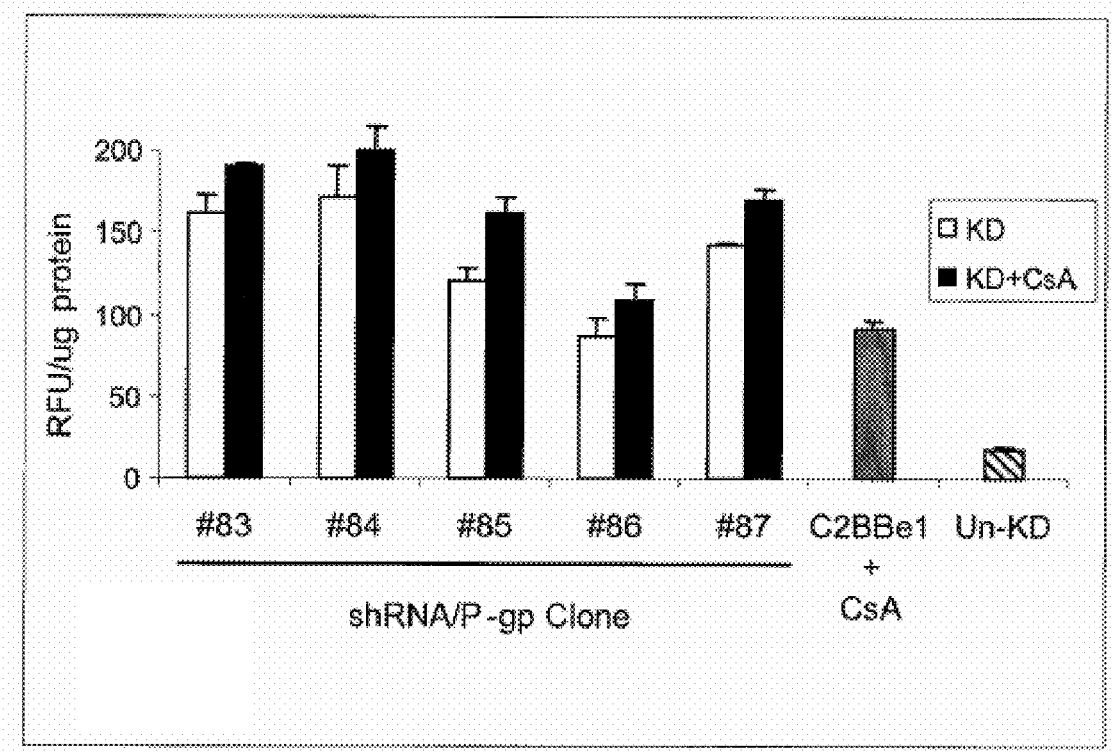
FIG. 1 shows P-gp function was significantly decreased in cells transduced with lentiviruses containing SEQ ID NOs: 1, 2, 3, 4, or 5 (shRNA/P-gp 83, 84, 85, 86, or 87, respectively) as described herein, as determined by intracellular calcein fluorescence. shRNA/P-gp clone cells (KD) were treated in parallel with Cyclosporin A (CsA) (KD+CsA), an established P-gp inhibitor. CsA was used as a positive control (C2BBe1+CsA), and unknockdown, non-transduced C2BBe1 cells (Un-KD) were used as a negative control to show baseline calcein retention.

Various terms relating to the methods and other aspects of the present invention are used throughout the specification and claims. Such terms are to be given their ordinary meaning in the art to which the invention pertains, unless otherwise indicated. Other specifically defined terms are to be construed in a manner consistent with the definition provided herein. Although any methods and materials similar or equivalent to those described herein can be used in the practice for testing of the present invention, the preferred materials and methods are described herein.

The following abbreviations are used throughout the specification. Papp: Permeability coefficient; PappA-B: Permeability coefficient in the apical (A) to basolateral (B) direction; PappB-A: Permeability coefficient in the basolateral (B) to apical (A) direction; ER: Efflux ratio, PappB-A/PappA-B ratio; P-gp: P-glycoprotein; MDR1: Multi-drug resistance protein 1; BCRP: Breast cancer resistance protein; MRP: Multi-drug resistance-associated protein; MRP2: Multi-drug resistance-associated protein 2; DMEM, Dulbecco's Modified Eagle Medium; FBS, fetal bovine serum; FTC: Fumitremorgin C; CsA: Cyclosporin A; MK571: MRP Inhibitor; TEER, transepithelial electrical resistance; KD: Knockeddown; WT: Wild-type, unmodified parental cell line; C2BBe1WT: Unmodified C2BBe1 cells; C2BBe1 Pgp-KD: C2BBe1 cells in which the expression of Pgp has been suppressed; C2BBe1 BCRP-KD: C2BBe1 cells in which the expression of BCRP has been suppressed; C2BBe1 MRP2-KD: C2BBe1 cells in which the expression of MRP2 has been suppressed; MDCK: Madin-Darby canine kidney; MDR1-MDCK: MDCK cell line transfected with the human MDR1 gene, which overexpresses; BCRP-MDCK: MDCK cell line transfected with the human BCRP gene, which overexpresses; MRP2-MDCK: MDCK cell line transfected with the human MRP2 gene, which overexpresses; nt, nucleotide.

As used in this specification and the appended claims, the singular forms "a," "an," and "the" include plural referents unless the content clearly dictates otherwise. Thus, for example, reference to "a cell" includes a combination of two or more cells, and the like.

The term "about" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Isolated" means altered "by the hand of man" from the natural state. If a molecule or composition occurs in nature, it has been "isolated" if it has been changed or removed from its original environment, or both. For example, a polynucleotide or a polypeptide naturally present in a living plant or animal is not "isolated," but the same polynucleotide or polypeptide separated from the coexisting materials of its natural state is "isolated" as the term is employed herein.

"Polynucleotide," synonymously referred to as "nucleic acid molecule," refers to any polyribonucleotide or polydeoxyribonucleotide, which may be unmodified RNA or DNA or modified RNA or DNA. "Polynucleotides" include, without limitation single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

A "vector" is a replicon, such as plasmid, phage, cosmid, or virus to which another nucleic acid segment may be operably inserted so as to bring about the replication or expression of the segment.

The term "express," "expressed," or "expression" of a nucleic acid molecule refers to the biosynthesis of a gene product. The term encompasses the transcription of a gene into RNA. For example, but not by way of limitation, a regulatory gene such as an antisense nucleic acid or interfering nucleic acid can be expressed by transcription as antisense RNA or RNAi or shRNA. The term also encompasses translation of RNA into one or more polypeptides, and encompasses all naturally occurring post-transcriptional and post-translational modifications.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g., enhancers) in an expression vector.

A "heterologous" region of a nucleic acid construct is an identifiable segment (or segments) of the nucleic acid molecule within a larger molecule that is not found in association with the larger molecule in nature. Thus, when the heterologous region encodes a mammalian gene, the gene will usually be flanked by DNA that does not flank the mammalian genomic DNA in the genome of the source organism.

A cell has been "transformed" or "transduced" by exogenous or heterologous nucleic acids such as DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell, or "stable cell" is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

As used herein, "test compound" refers to any purified molecule, substantially purified molecule, molecules that are one or more components of a mixture of compounds, or a mixture of a compound with any other material that can be analyzed using the methods of the present invention. Test compounds can be organic or inorganic chemicals, or biomolecules, and all fragments, analogs, homologs, conjugates, and derivatives thereof "Biomolecules" include proteins, polypeptides, nucleic acids, lipids, monosaccharides, polysaccharides, and all fragments, analogs, homologs, conjugates, and derivatives thereof. Test compounds can be of natural or synthetic origin, and can be isolated or purified from their naturally occurring sources, or can be synthesized de novo. Test compounds can be defined in terms of structure or composition, or can be undefined. The compound can be an isolated product of unknown structure, a mixture of several known products, or an undefined composition comprising one or more compounds. Examples of undefined compositions include cell and tissue extracts, growth medium in which prokaryotic, eukaryotic, and archaebacterial cells have been cultured, fermentation broths, protein expression libraries, and the like.

"Membrane efflux transport protein" refers to any protein transporters localized to a cell membrane. Such transport proteins can have as one of their biological functions the ability to mediate the removal of compounds from the cell interior, herein referred to as "efflux activity." Efflux activity can result in broad substrate specificity resistance to multiple structure-unrelated therapeutic agents, i.e., multidrug resistance (MDR). The ability of membrane efflux transport protein to confer clinical MDR has generated considerable interest in identifying the substrates and/or inhibitors of such protein and so reversing innate or acquired drug resistance (N. Mizuno, et al. (2003) Pharmacological Rev. 55:425-61).

As used herein, the term "modulate" means any change, enhancement or inhibition in the amount, quality, or activity of a particular biomolecule or pathway. "Inhibit" or "inhibition" or "interfere" means to reduce, decrease, block, prevent, delay, inactivate, desensitize, stop, or downregulate the biological activity or expression of a molecule, protein or pathway of interest. In some preferred embodiments of the invention, the level of the expression or biological activity of a protein or pathway of interest, for example, efflux activity or expression of membrane efflux proteins, refers to a decrease (inhibition or downregulation) or increase (upregulation) of greater than from about 50% to about 99%, and more specifically, about 50%, 51%, 52%, 53%, 54%, 55%, 56%, 57%, 58%, 59%, 60%, 61%, 62%, 63%, 64%, 65%, 66%, 67%, 68%, 69% 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or more. The inhibition may be direct, i.e., operate on the molecule or pathway of interest itself, or indirect, i.e., operate on a molecule or pathway that affects the molecule or pathway of interest.

"Knockdown" refers to a cell or organism having reduced expression of one or more genes. As will be appreciated by those skilled in the art, a knockdown will exhibit at least about a 20% reduction in expression, preferably will exhibit at least about a 50% reduction in expression, and more preferably will exhibit at least about a 75% reduction in expression, although higher reductions are possible, including at least about a 80%, 81%, 82%, 83%, 84%, 85%, 86%, 87%, 88%, 89%, 90%, 91%, 92%, 93%, 94%, 95%, 96%, 97%, 98%, 99%, or more reduction in expression.

With respect to nucleic acids, the term "percent identity" refers to the percentage of sequence identity found in a comparison of two or more nucleic acid sequences.

"Gastrointestinal absorption" refers to the uptake of chemicals, including biomolecules and test compounds, into or across tissues that comprise the gastrointestinal tract. For example, absorption includes, but is not limited to, uptake of compounds from the apical side of a cell and the release of compounds from the basolateral side of a cell. The gastrointestinal tract comprises the stomach, small intestine, and large intestine. "No gastrointestinal absorption" means 0% of the compound is absorbed. "Low gastrointestinal absorption" means that more than 0%, but less than 25% of a compound is absorbed. "Moderate gastrointestinal absorption" means that greater than or equal to 25% but less than 85% of a compound is absorbed. "High gastrointestinal absorption" means that greater than or equal to 85% of a compound is absorbed.

As used herein, "measure" or "determine" refers to any qualitative or quantitative determinations.

"Transcellular transport" refers to the movement of a compound across a layer of epithelial cells whereby the compound is moved through the cells and not the spaces between cells such as tight junctions. By way of contrast, "paracellular transport" refers to the movement of a compound across a layer of epithelial cell whereby the compound is moved through the tight junctions between cells.

The following sections set forth the general procedures involved in practicing the present invention. To the extent that specific materials are mentioned, it is merely for the purpose of illustration, and is not intended to limit the invention. Unless otherwise specified, general biochemical and molecular biological procedures, such as those set forth in Ausubel et al., CURRENT PROTOCOLS IN MOLECULAR BIOLOGY, John Wiley & Sons, New York, 1998; Sambrook et al., MOLECULAR CLONING: A LABORATORY MANUAL, 2D ED., Cold Spring Harbor Laboratory Press, Plainview, N.Y., 1989; Kaufman et al., Eds., HAND- BOOK OF MOLECULAR AND CELLULAR METHODS IN BIOLOGY AND MEDICINE, CRC Press, Boca Raton, 1995. PROTEIN EXPRESSION: A PRACTICAL APPROACH (S J Higgins and B. D Hames, Eds.) Oxford University Press, Oxford, UK 1999; Charles Hardin et al. CLONING, GENE EXPRESSION, AND PROTEIN PURIFICATION: EXPERIMENTAL PROCEDURES AND PROCESS RATIONALE Oxford University Press, Inc. New York, N.Y. 2001; and MEMBRANE PROTEIN PROTOCOLS: EXPRESSION, PURIFICATION, AND CHARACTERIZATION (METHODS IN MOLECULAR BIOLOGY (Clifton, N.J.), V. 228.) Barry Steven Selinsky, Humana Press, Inc. Totowa, N.J. 2003 are used.

It is to be understood that this invention is not limited to particular methods, reagents, compounds, compositions or biological systems, which can, of course, vary. It is also to be understood that the terminology used herein is for the purpose of describing particular embodiments only, and is not intended to be limiting.

Efflux transport proteins, particularly those expressed by intestinal cells, can limit the absorption of substrate drugs, and can mediate drug-drug interactions that alter, frequently reducing, drug availability or efficacy. Thus, understanding the role of the various efflux transporters in drug absorption is important in the development of lead compounds. To date, the study of efflux transporters has largely relied on the use of chemical inhibitors. However, the use of chemical inhibitors is problematic as the inhibitors are not specific and can affect other cellular processes thereby blurring the overall picture of drug absorption. It has been discovered in accordance with the present invention that the expression of the various efflux transport proteins can be stably inhibited at the genetic level using virally-transformed cells. It has further been discovered that targeted knockdown of the various transporters permits the identification of the particular transporters involved in drug transport with a high degree of certainty. The knockdown approach described herein provides stable, sequence-specific silencing of membrane efflux transport proteins induced by endogenous expression of shRNA by lentiviral vectors. The invention is advantageous over previous knockdown attempts as the transformation with lentiviral vectors provides permanent, stable inhibition of gene expression, and provides the additional advantage of circumventing non-specific inhibition of other cellular functions that would be expected from chemical inhibition.

Accordingly, in one aspect, the invention features methods for screening test compounds for gastrointestinal absorption in animals. The methods comprise modulating, and preferably inhibiting, the expression of at least one membrane efflux transport protein in a cell, contacting the cell with a test compound, measuring transcellular transport of the test compound, and comparing the transcellular transport measurements with reference values for transcellular transport of compounds with no gastrointestinal absorption, low gastrointestinal absorption, moderate gastrointestinal absorption, or high gastrointestinal absorption. The values obtained by experiments measuring the transcellular transport of the compound indicate the degree to which the test compound is likely to be absorbed upon administration to the animal. The methods are thus useful as in vitro models, among other things.

Membrane efflux transport proteins, synonymously referred to herein as drug transporters or drug transport proteins, generally are comprised of one or more subunits that span the plasma membrane of mammalian cells, including mammalian epithelial cells. Mammalian epithelial cells are often polarized cells, meaning that their membrane composition differs between the apical or outward facing portion of the cell, and the basolateral or inward portion of the cell. By apical or outward, it is meant that such portions of the cell face a body compartment connected with the outside environment, such as the lumen of the intestine or the lining of the urinary tract or the bile duct. By basolateral or inward, it is meant that such portions of the cell face the interior of the body, typically the body's blood supply. Epithelial cells play a role in absorption and elimination of nutrients, drugs and environmental toxins as well as metabolites derived from compounds in each of these categories. Epithelial cells can grow together in sheets in which neighboring cells are linked together by tight junctions, which are intercellular connections that limit the diffusion of ions and larger molecules between cells, called paracellular transport.

Liver hepatocytes and brain capillary endothelial cells share certain common features with epithelial cells, including the presence of tight junctions and asymmetric expression of membrane transport proteins. Many epithelial cells maintain this asymmetrical orientation even when cultured outside the body. This can require special in vitro culture conditions, such as the use of collagen-coated plastic ware, or the addition of one or more differentiation-inducing proteins or hormones to the cell culture medium. Other specialized culture conditions are known to and readily practiced by those of skill in the art.

Membrane efflux transporters can be distributed asymmetrically in epithelial cells. This asymmetrical distribution can lead to vectorial transport of compounds that are substrates for such transporters. Vectorial transport means that the rate of transport of a compound differs significantly depending on whether the compound is applied to the apical or basolateral surface of an epithelial cell layer.

Mammalian membrane transporters can be divided into two general families based on their gene sequence relationships and modes of compound transport. The first class is referred to as ABC transporters. The term "ABC" refers to a common structural feature of this family of transporters, the presence of an Adenosine triphosphate (A) binding (B) cassette (C) structural motif. These transport proteins typically move chemicals from inside of a cell or from within the phospholipid bilayer of the cell membrane to outside the cell against an unfavorable concentration gradient by using the energy provided by the hydrolytic cleavage of adenosine triphosphate (ATP) to adenosine diphosphate (ADP) and phosphate ion (Pi). Without intending to be limited to any particular theory or mechanism of action, it is believed that, in addition to their roles as drug transporters, members of the ABC family play a role in excretion of bile salts and phospholipids into the bile as well as regulating the phospholipid and cholesterol content of cellular membranes.

The second major family of transporters present in mammals is referred to as SLC family where the abbreviation "SLC" refers to the major characteristics of this family of "Solute Linked Carriers," namely that transport of drugs into or out of a cell is linked to transport of a physiological solute, such as sodium ion, proton or metabolic product, in either the opposite direction, via solute exchange, or in the same direction, via co-transport. Unlike the ABC family of transporters, the SLC family generally does not require energy derived from ATP hydrolysis to function. Instead, such transporters utilize the concentration gradients of the co-transported and/or exchanged molecules or ions as an energy source for transporting drugs against an unfavorable concentration gradient. Also, unlike ABC family transporters, SLC frequently mediate compound uptake into cells. In some cases, such as in kidney tubule epithelial cells, SLC and ABC transporters are present on opposite sides of the polarized epithelium and work in concert to deliver compounds from the blood into the urine against unfavorable concentration gradients (Wright S. et al. (2004) Physiol. Rev 84:987-1049).

Table 1, below, lists human members of the ABC transporter family and some of their known substrates and inhibitors (Zhang L, et al. (2006) Molecular Pharmaceutics 3: 62-9). The list of substrates and inhibitors is for illustration purposes, and is not intended to be exhaustive.

TABLE 1

ABC transport proteins and known substrates and inhibitors

| Transporter Gene | Common Aliases | Tissue Distribution | Substrates | Inhibitors |
|---|---|---|---|---|
| ABCB1 | P-gp, MDR1 | Intestine, liver, kidney, brain, placenta, adrenal, testes | Digoxin, fexofenadine, indinavir, vincristine, colchicine, topotecan, paclitaxel, loperamide | Ritonavir, cyclosporine, verapamil, erythromycin, ketoconazole, itraconazole, quinidine, elacridar (GF120918), azithromycin, valspodar (PSC833), LY335979 |
| ABCB11 | BSEP | Liver | Vinblastine | |
| ABCC1 | MRP1 | Intestine, liver, kidney, brain | Adefovir, indinavir | |
| ABCC2 | MRP2, CMOAT | Intestine, kidney, liver, brain | Indinavir, cisplatin | Cyclosporine |
| ABCC3 | MRP3, CMOAT2 | Intestine, liver, kidney, placenta | Etoposide, methotrexate, tenoposide | |
| ABCC6 | MRP6 | Liver, kidney | Cisplatin, daunorubicin | |
| ABCG2 | BCRP | Intestine, liver, breast, placenta | Duanorubicin, doxorubicin, topotecan, rosuvastatin, sulfasalazine | Elacridar (GF120918), fumitremorgin C, gefitinib |

The drug rifampin and the herbal supplement St. John's wort are established inducers of increased ABCB1 gene expression. The ABC transporter family mediates transport of drugs from a wide variety of therapeutic classes, including antineoplastic drugs, such as cisplatin and topotecan, antiviral drugs, such as indinavir and adefovir and the anti-hyperlipidemic drug, rosuvastatin. There is considerable overlap among substrates for different transporters. For example, indinavir is a substrate for ABCB1, ABCC1, and ABCC2. Similarly, topotecan is a substrate for ABCB1 and ABCG2. At least in the case of ABCB1, or P-gp as it is commonly referred to, several drugs from a wide range of therapeutic classes can inhibit the transporter without being substrates of the transporter. Orthologs of these human transporters with varying degrees of gene sequence homology exist in other mammalian species, such as rats, mice, dogs and non-human primates.

The inventive methods are applicable for analyzing test compounds for their gastrointestinal absorption in any animal, preferably are applicable to mammals, including companion animals such as dogs, cats, rabbits, and are most preferably applicable to humans. As such, the methods can be carried out in any cell that is representative of an animal or group of animals of interest. The cells can be freshly isolated, established cell lines, or can be cell lines produced de novo. The cell preferably expresses at least one membrane efflux transport protein, although in some embodiments, the cell expresses 2, 3, 4, 5, 6, 7, 8, 9, 10, or more such transport proteins. In some aspects, the cell can be engineered specifically to express a particular membrane efflux transport protein, and can be engineered specifically to express two or more particular membrane efflux transport proteins. Moreover, such cells can be engineered to express the particular membrane efflux transport proteins at a particular density, or, in polarized cells, at a particular location on the cell surface, for example, at the basal surface, at the apical surface, both the basal and apical surfaces, or neither the basal or apical surfaces. Methods for transforming cells to express a particular efflux protein transgene are known in the art and are routinely practiced, including those that are described and exemplified herein. Non-limiting examples of membrane efflux transport proteins that are suitable for analysis using the claimed methods and described cells include P-glycoprotein, Multidrug Resistance-Associated Protein 2, and Breast Cancer Resistance Protein. Such transporters can have SEQ ID NOs: 6, 7, or 8, or allelic variants, homologs, and analogs thereof.

The cell is preferably isolated from or alternatively has the characteristics of a cell isolated from the gastrointestinal tract of the animal. For example, the cell can be isolated from the stomach, the small intestine, or the large intestine, including from any subpart of these organs. In some preferred embodiments, the cells are intestinal cells, particularly intestinal epithelial cells. In some preferred embodiments, the cells are intestinal cell lines. In highly preferred embodiments, the cells are Caco-2 cells, C2BBe1 cells, HT-29 cells, or T-84 cells. Alternatively, Madin-Darby Canine Kidney (MDCK) cells, a cell type known to approximate many of the characteristics of polarized epithelial cells of the gastrointestinal tract of animals, could also be used as one embodiment of the present invention (Maksymowych, A B and Simpson L L, J. Biol. Chem. 273:21950-57 (1998)). MDCK cells (MDR-MDCK) have already been used to assess human P-gp mediated transport of blood-brain barrier compounds (Wang, Q. et al., Int. J. Pharmaceutics 288:349-59 (2005)).

Modulation of the expression of the at least one membrane efflux transport protein can occur by any means suitable in the art. In highly preferred embodiments, the expression of the transport proteins is inhibited. In some aspects, the inhibition is effectuated on the genetic level. For example, in cells specifically engineered to express a transgene encoding a particular efflux transport protein, the transgene can be placed under control of an inducible promoter. Inducible promoters suitable for use in this invention will be known to those of skill in the art.

In some preferred embodiments, genes encoding membrane efflux transport proteins such as P-glycoprotein, Multidrug Resistance-Associated Protein 2, and Breast Cancer Resistance Protein can be inhibited through the use of a variety of other post-transcriptional gene silencing (RNA silencing) techniques. RNA silencing involves the processing of double-stranded RNA (dsRNA) into small 21-28 nucleotide fragments by an RNase H-based enzyme ("Dicer" or "Dicer-like"). The cleavage products, which are siRNA (small interfering RNA) or miRNA (micro-RNA) are incorporated into protein effector complexes that regulate gene expression in a sequence-specific manner.

RNA interference (RNAi) is a mechanism of post-transcriptional gene silencing mediated by double-stranded RNA (dsRNA), which is distinct from antisense and ribozyme-based approaches (see Jain K K Pharmacogenomics (2004) 5:239-42, for a review of RNAi and siRNA). RNA interference is useful in a method for inhibiting the expression of a membrane efflux transport protein in an animal such as a human by administering to the animal a nucleic acid (e.g., dsRNA) that hybridizes under stringent conditions to a gene encoding a membrane efflux transport protein, and attenuates expression of the target gene. RNA interference provides shRNA or siRNA that comprise multiple sequences that target one or more regions of the membrane efflux transport protein target gene. dsRNA molecules (shRNA or siRNA) are believed to direct sequence-specific degradation of mRNA in cells of various types after first undergoing processing by an RNase III-like enzyme called DICER (Bernstein E et al. (2001) Nature 409:363-366) into smaller dsRNA molecules comprised of two 21 nt strands, each of which has a 5' phosphate group and a 3' hydroxyl, and includes a 19 nt region precisely complementary with the other strand, so that there is a 19 nt duplex region flanked by 2 nt-3' overhangs. RNAi is thus mediated by short interfering RNAs (siRNA), which typically comprise a double-stranded region approximately 19 nucleotides in length with 1-2 nucleotide 3' overhangs on each strand, resulting in a total length of between approximately 21 and 23 nucleotides. In mammalian cells, dsRNA longer than approximately 30 nucleotides typically induces nonspecific mRNA degradation via the interferon response. However, the presence of siRNA in mammalian cells, rather than inducing the interferon response, results in sequence-specific gene silencing.

Viral vectors or DNA vectors encode short hairpin RNA (shRNA) which are processed in the cell cytoplasm to short interfering RNA (siRNA). In general, a short, interfering RNA (siRNA) comprises an RNA duplex that is preferably approximately 19 basepairs long and optionally further comprises one or two single-stranded overhangs or loops. An siRNA may comprise two RNA strands hybridized together, or may alternatively comprise a single RNA strand that includes a self-hybridizing portion. siRNAs may include one or more free strand ends, which may include phosphate and/or hydroxyl groups. siRNAs typically include a portion that hybridizes under stringent conditions with a target transcript. One strand of the siRNA (or, the self-hybridizing portion of the siRNA) is typically precisely complementary with a region of the target transcript, meaning that the siRNA hybridizes to the target transcript without a single mismatch. In certain embodiments of the invention in which perfect complementarity is not achieved, it is generally preferred that any mismatches be located at or near the siRNA termini.

siRNAs have been shown to downregulate gene expression when transferred into mammalian cells by such methods as transfection, electroporation, cationic liposome-mediated transfection, or microinjection, or when expressed in cells via any of a variety of plasmid-based approaches. RNA interference using siRNA is reviewed in, e.g., Tuschl T (2002) Nat. Biotechnol. 20:446-8; Yu J-Y et al. (2002) Proc. Natl. Acad. Sci. 99:6047-52; Sui G et al. (2002) Proc. Natl. Acad. Sci. USA., 99:5515-20; Paddison P J et al. (2002) Genes and Dev. 16:948-58; Brummelkamp T R et al. (2002) Science 296:550-3, 2002; Miyagashi M et al. (2002) Nat. Biotech. 20:497-500; and, Paul C P et al. (2002) *Nat. Biotechnol.* 20:505-8. As described in these and other references, the siRNA may consist of two individual nucleic acid strands or of a single strand with a self-complementary region capable of forming a hairpin (stem-loop) structure. A number of variations in structure, length, number of mismatches, size of loop, identity of nucleotides in overhangs, etc., are consistent with effective siRNA-triggered gene silencing. While not wishing to be bound by any theory, it is thought that intracellular processing (e.g., by DICER) of a variety of different precursors results in production of siRNA capable of effectively mediating gene silencing. Generally it is preferred to target exons rather than introns, and it may also be preferable to select sequences complementary to regions within the 3' portion of the target transcript. Generally it is preferred to select sequences that contain approximately equimolar ratio of the different nucleotides and to avoid stretches in which a single residue is repeated multiple times.

siRNAs may thus comprise RNA molecules having a double-stranded region approximately 19 nucleotides in length with 1-2 nucleotide 3' overhangs on each strand, resulting in a total length of between approximately 21 and 23 nucleotides. As used herein, siRNAs also include various RNA structures that may be processed in vivo to generate such molecules. Such structures include RNA strands containing two complementary elements that hybridize to one another to form a stem, a loop, and optionally an overhang, preferably a 3' overhang. Preferably, the stem is approximately 19 bp long, the loop is about 1-20, more preferably about 4-10, and most preferably about 6-8 nt long and/or the overhang is about 1-20, and more preferably about 2-15 nt long. In certain embodiments of the invention the stem is minimally 19 nucleotides in length and may be up to approximately 29 nucleotides in length. Loops of 4 nucleotides or greater are less likely subject to steric constraints than are shorter loops and therefore may be preferred. The overhang may include a 5' phosphate and a 3' hydroxyl. The overhang may, but need not comprise a plurality of U residues, e.g., between 1 and 5 U residues. Classical siRNAs as described above trigger degradation of mRNAs to which they are targeted, thereby also reducing the rate of protein synthesis. In addition to siRNAs that act via the classical pathway, certain siRNAs that bind to the 3' UTR of a template transcript may inhibit expression of a protein encoded by the template transcript by a mechanism related to but distinct from classic RNA interference, e.g., by reducing translation of the transcript rather than decreasing its stability. Such RNAs are referred to as microRNAs (miRNAs) and are typically between approximately 20 and 26 nucleotides in length, e.g., 22 nt in length. It is believed that they are derived from larger precursors known as small temporal RNAs (stRNAs) or mRNA precursors, which are typically approximately 70 nt long with an approximately 4-15 nt loop (Grishok A et al. (2001) Cell 106:23-4; Hutvagner G et al. (2001) Science 293:834-8; Ketting R F et al. (2001) Genes Dev. 15:2654-9). Endogenous RNAs of this type have been identified in a number of organisms including mammals, suggesting that this mechanism of post-transcriptional gene silencing may be widespread (Lagos-Quintana M et al. (2001) Science 294: 853-8, 2001; Pasquinelli A E (2002) Trends Gen. 18:171-3). MicroRNAs have been shown to block translation of target transcripts containing target sites in mammalian cells (Zeng Y et al. (2002) Mol. Cell. 9:1327-33).

siRNAs such as naturally occurring or artificial (i.e., designed by humans) mRNAs that bind within the 3' UTR (or elsewhere in a target transcript) and inhibit translation may tolerate a larger number of mismatches in the siRNA/template duplex, and particularly may tolerate mismatches within the central region of the duplex. In fact, there is evidence that some mismatches may be desirable or required as naturally occurring stRNAs frequently exhibit such mismatches as do mRNAs that have been shown to inhibit translation in vitro. For example, when hybridized with the target transcript such siRNAs frequently include two stretches of perfect complementarity separated by a region of mismatch. A variety of structures are possible. For example, the mRNA may include multiple areas of nonidentity (mismatch). The areas of nonidentity (mismatch) need not be symmetrical in the sense that both the target and the mRNA include nonpaired nucleotides.

Typically the stretches of perfect complementarity are at least 5 nucleotides in length, e.g., 6, 7, or more nucleotides in length, while the regions of mismatch may be, for example, 1, 2, 3, or 4 nucleotides in length.

Hairpin structures designed to mimic siRNAs and mRNA precursors are processed intracellularly into molecules capable of reducing or inhibiting expression of target transcripts (McManus M T et al. (2002) RNA 8:842-50). These hairpin structures, which are based on classical siRNAs consisting of two RNA strands forming a 19 by duplex structure are classified as class I or class II hairpins. Class I hairpins incorporate a loop at the 5' or 3' end of the antisense siRNA strand (i.e., the strand complementary to the target transcript whose inhibition is desired) but are otherwise identical to classical siRNAs. Class II hairpins resemble mRNA precursors in that they include a 19 nt duplex region and a loop at either the 3' or 5' end of the antisense strand of the duplex in addition to one or more nucleotide mismatches in the stem. These molecules are processed intracellularly into small RNA duplex structures capable of mediating silencing. They appear to exert their effects through degradation of the target mRNA rather than through translational repression as is thought to be the case for naturally occurring mRNAs and stRNAs.

Thus it is evident that a diverse set of RNA molecules containing duplex structures is able to mediate silencing through various mechanisms. For the purposes of the present invention, any such RNA, one portion of which binds to a target transcript and reduces its expression, whether by triggering degradation, by inhibiting translation, or by other means, is considered to be an siRNA, and any structure that generates such an siRNA (i.e., serves as a precursor to the RNA) is useful in the practice of the present invention.

A further method of RNA interference for use in the present invention is the use of short hairpin RNAs (shRNA). A plasmid containing a DNA sequence encoding for a particular desired siRNA sequence is delivered into a target cell via transfection or virally-mediated infection. Once in the cell, the DNA sequence is continuously transcribed into RNA molecules that loop back on themselves and form hairpin structures through intramolecular base pairing. These hairpin structures, once processed by the cell, are equivalent to transfected siRNA molecules and are used by the cell to mediate RNAi of the desired protein. The use of shRNA has an advantage over siRNA transfection as the former can lead to stable, long-term inhibition of protein expression. Inhibition of protein expression by transfected siRNAs is a transient phenomenon that does not occur for times periods longer than several days. In some cases, this may be preferable and desired. In cases where longer periods of protein inhibition are necessary, shRNA mediated inhibition is preferable. The use of shRNA is particularly preferred. Typically, siRNA-encoding vectors are constructs comprising a promoter, a sequence of the target gene to be silenced in the "sense" orientation, a spacer, the antisense of the target gene sequence, and a terminator.

Inhibition of the expression of the membrane efflux transport proteins can also be effectuated by other means that are known and readily practiced in the art. For example, antisense nucleic acids can be used. Antisense RNA transcripts have a base sequence complementary to part or all of any other RNA transcript in the same cell. Such transcripts have been shown to modulate gene expression through a variety of mechanisms including the modulation of RNA splicing, the modulation of RNA transport and the modulation of the translation of mRNA (Denhardt D T (1992) Ann. N Y Acad. Sci. 660:70-6, 1992; Nellen W et al. (1993) Trends Biochem. Sci. 18:419-23; and, Baker B F et al. (1999) Biochim. Biophys. Acta. 1489: 3-18). Accordingly, in certain embodiments of the invention, inhibition of one or more membrane efflux transport proteins in a cell is accomplished by expressing an antisense nucleic acid molecule in the cell.

Antisense nucleic acids are generally single-stranded nucleic acids (DNA, RNA, modified DNA, or modified RNA) complementary to a portion of a target nucleic acid (e.g., an mRNA transcript) and therefore able to bind to the target to form a duplex. Typically, they are oligonucleotides that range from 15 to 35 nucleotides in length but may range from 10 up to approximately 50 nucleotides in length. Binding typically reduces or inhibits the function of the target nucleic acid, such as a gene encoding a membrane efflux transport protein. For example, antisense oligonucleotides may block transcription when bound to genomic DNA, inhibit translation when bound to mRNA, and/or lead to degradation of the nucleic acid. Inhibition of the expression of a membrane efflux transport protein can be achieved by the administration of antisense nucleic acids or peptide nucleic acids comprising sequences complementary to those of the mRNA that encodes the membrane efflux transport protein. Antisense technology and its applications are well known in the art and are described in Phillips, M. I. (ed.) *Antisense Technology, Methods Enzymol.*, 2000, Volumes 313 and 314, Academic Press, San Diego, and references mentioned therein. See also Crooke, S. (ed.) "ANTISENSE DRUG TECHNOLOGY: PRINCIPLES, STRATEGIES, AND APPLICATIONS" (1$^{st}$ Edition) Marcel Dekker; and references cited therein.

Antisense oligonucleotides can be synthesized with a base sequence that is complementary to a portion of any RNA transcript in the cell. Antisense oligonucleotides can modulate gene expression through a variety of mechanisms including the modulation of RNA splicing, the modulation of RNA transport and the modulation of the translation of mRNA. Various properties of antisense oligonucleotides including stability, toxicity, tissue distribution, and cellular uptake and binding affinity may be altered through chemical modifications including (i) replacement of the phosphodiester backbone (e.g., peptide nucleic acid, phosphorothioate oligonucleotides, and phosphoramidate oligonucleotides), (ii) modification of the sugar base (e.g., 2'-O-propylribose and 2'-methoxyethoxyribose), and (iii) modification of the nucleoside (e.g., C-5 propynyl U, C-5 thiazole U, and phenoxazine C) (Wagner R W (1995) Nat. Medicine 1:1116-8; Varga L V et al. (1999) Immun. Lett. 69:217-24; Neilsen P E (1999) Curr. Opin. Biotech. 10:71-5; and, Woolf T M (1990) Nucleic Acids Res. 18:1763-9).

Inhibition of membrane efflux transport proteins can also be effectuated by use of ribozymes. Certain nucleic acid molecules referred to as ribozymes or deoxyribozymes have been shown to catalyze the sequence-specific cleavage of RNA molecules. The cleavage site is determined by complementary pairing of nucleotides in the RNA or DNA enzyme with nucleotides in the target RNA. Thus, RNA and DNA enzymes can be designed to cleave to any RNA molecule, thereby increasing its rate of degradation (Cotten M et al. (1989) EMBO J. 8: 3861-6, 1989; and, Usman N et al. (1996) Curr. Opin. Struct. Biol. 1:527-33).

In preferred aspects of the invention, the cells used in the inventive methods can be specifically transformed with transcription-silencing nucleic acids such as shRNA or siRNA, or can be transformed with vectors encoding such nucleic acids such that the cell expresses the inhibitory nucleic acid molecules. Transformation of the cells can be carried out according to any means suitable in the art, including those described and exemplified herein. In specific embodiments, the inhibitory nucleic acid molecules comprise SEQ ID NO: 1, 2, 3, 4, 5, 17, 18, 19, 20, 21, 22, 23, 24, 25, or 26, or analogs, homologs, derivatives, or allelic variants thereof.

In accordance with the inventive methods, test compounds can be screened at a single dose, or with multiple doses. In some embodiments, the test compound is evaluated at multiple dosages ranging from the compound's free maximal therapeutic plasma concentration (Cmax) to a concentration equal to or greater than 500-fold over the compound's Cmax. In some embodiment, the test compound is evaluated at multiple dosages ranging from the compound's Cmax to a concentration equal to or greater than 250-fold over the compound's Cmax. In some embodiments, the test compound is evaluated at multiple dosages ranging from the compound's Cmax to a concentration equal to or greater than 100-fold over the compound's Cmax. In some embodiments, the test compound is evaluated at multiple dosages ranging from the compound's Cmax to a concentration equal to or greater than 50-fold over the compound's Cmax. In some embodiments, the test compound is evaluated at multiple dosages ranging from the compound's Cmax to a concentration equal to or greater than 30-fold over the compound's Cmax. In some embodiments, the test compound is evaluated at multiple dosages ranging from the compound's Cmax to a concentration equal to or greater than 10-fold over the compound's Cmax. Cmax can be determined according to any means available in the art. The skilled artisan will appreciate that such means are known and routine in the art. The compound can be tested at 1, 2, 3, 4, 5, 6, 7, 8, 9, 10, 11, 12, 13, 14, 15, or more concentrations within this range.

In some aspects, multiple test compounds are contacted with the cell to evaluate drug-drug interactions. Drug-drug interactions are defined as influences of one drug on the pharmacokinetics or pharmacodynamics of a second drug co-administered to the same subject. Pharmacokinetics refers to the influence of varying drug doses and methods of administration on the concentration of drug in various body tissues, such as blood, blood plasma, brain, etc., as a function of time after drug administration. Pharmacodynamics refers to the study of the influence of drug dose and route of administration on the pharmacological response, such as blood pressure, blood lipid level, number of infectious viral particles in a tissue, etc., to drug administration. Drug-drug interactions typically occur by one of three mechanisms: 1) two or more drugs compete for the same limited quantity of an enzyme or transport protein responsible for their metabolism, uptake or efflux in the body; 2) one drug inhibits an enzyme, uptake or efflux transporter that mediates the metabolism, uptake or excretion of one or more other drugs by the body; or 3) one drug enhances or inhibits the production of an enzyme, uptake or efflux transporter responsible for the metabolism, uptake or efflux of one or more other drugs in the body. In some cases the interacting substance is not a drug, but rather a natural component of a dietary product, such as a component of a fruit juice, such as grapefruit juice, or an herbal supplement, such as Saint John's wort. Instances of drug-drug interaction associated with a membrane efflux transport protein have been reported. For example, the oral bioavailability of digoxin, a p-glycoprotein substrate, was increased by talinolol (Westphal K et al. (2000) Clin. Pharmacol. Ther. 68:6-12). In another instance, renal clearance of digoxin was hampered by clarithromycin resulting in elevated systemic digoxin concentration (Wakasugi H et al. (1998) Clin. Pharmacol. Ther. 64:123-8). Therefore, membrane efflux transport protein mediated drug-drug interactions may alter the pharmacokinetics of a drug in terms of drug absorption, distribution, and clearance, and may lead to unexpected response to the drug. Cell lines with varying patterns of efflux transport protein expression offer the ability to identify substrates and inhibitors of such protein explicitly, and thus make it possible to predict potential drug-drug interactions and to provide guidance for adjustment of drug dosage regimen. On Sep. 11, 2006, the US Food and Drug Administration (FDA) announced a draft guidance discussing the importance of in vitro assays for determining drug-drug interactions and suggesting ways in which such assays could be carried out. The guidance also provides recommendations on human clinical studies that can be used to confirm or refute the in vitro findings (http://www.fda.gov/cder/drug/drugInteractions/default.htm).

Also featured are methods for screening compounds for gastrointestinal absorption that utilize a parallel analysis of the inhibition of different membrane efflux transport proteins in separate cells. For example, a given test compound can be screened in a panel of cells, each cell in the panel being a knockdown for expression of a different membrane efflux transport protein, or a different combination of membrane efflux transport proteins. Using such methods, those of skill in the art can advantageously determine the contribution of each individual transport protein or of particular combinations of transport proteins on the gastrointestinal absorption of a test compound.

Accordingly, in some aspects, the inventive methods comprise inhibiting the expression of a first membrane efflux transport protein in a first cell and inhibiting the expression of a second membrane efflux transport protein in a second cell, contacting the first and second cells with a test compound, and measuring transcellular transport of the test compound in the first and second cells. The transcellular transport measurements from each of the first and second cells can then be compared with reference values for transcellular transport of compounds with no gastrointestinal absorption, low gastrointestinal absorption, moderate gastrointestinal absorption, or high gastrointestinal absorption. The measurements indicate the role of the first and second membrane efflux transport proteins in transcellular transport of the test compound. In addition, the measurements relative to the reference values are predictive of the gastrointestinal absorption of the compound in the body of the animal of interest.

In some aspects, the methods comprise inhibiting additional membrane efflux transport proteins such as a third, fourth, fifth, sixth, or more transport proteins, or combinations thereof, in separate cells, thereby expanding the number of cells in the panel. Thus, in preferred embodiments, the methods comprise inhibiting the expression of a first membrane efflux transport protein in a first cell, inhibiting the expression of a second membrane efflux transport protein in a second cell, and inhibiting the expression of a third membrane efflux transport protein in a third cell, contacting the first, second, and third cells with a test compound, and measuring transcellular transport of the test compound in the first, second, and third cells. The transcellular transport measurements from each of the first, second, and third cells can then be compared with reference values for transcellular transport of compounds with no gastrointestinal absorption, low gastrointestinal absorption, moderate gastrointestinal absorption, or high gastrointestinal absorption. The measurements indicate the role of the first, second, and third membrane efflux transport proteins in transcellular transport of the test compound. In addition, the measurements relative to the reference values are predictive of the gastrointestinal absorption of the compound in the body of the animal of interest.

Variations on such methods comprise inhibiting the expression of two or more membrane efflux transport proteins in a first cell, and at least one membrane efflux transport protein in a second cell. In some aspects, the expression of two or more membrane efflux transport proteins can be inhibited, for example, by means of a single nucleic acid molecule that can inhibit the expression of two or more membrane efflux transport proteins. The membrane efflux transport protein in the second cell can be the same as one of the membrane efflux transport proteins in the first cell, or can be a different membrane efflux transport protein. These methods provide the skilled artisan with the advantage of being able to discern and characterize any synergistic effect of membrane efflux transport proteins in the cell.

The second, third, fourth (and the like) cells can be freshly isolated, established cell lines, or can be cell lines produced de novo. The cells preferably expresses at least one membrane efflux transport protein, although in some embodiments, the cell expresses 2, 3, 4, 5, 6, 7, 8, 9, 10, or more such transport proteins. In some aspects, the cells can be engineered specifically to express a particular membrane efflux transport protein, and can be engineered specifically to express two or more particular membrane efflux transport proteins. Moreover, such cells can be engineered to express the particular membrane efflux transport proteins at a particular density, or, in polarized cells, at a particular location on the cell surface, for example, at the basal surface, at the apical surface, both the basal and apical surfaces, or neither the basal or apical surfaces.

Non-limiting examples of membrane efflux transport proteins that are contemplated for analysis using panels of cells include P-glycoprotein, Multidrug Resistance-Associated Protein 2, and Breast Cancer Resistance Protein.

The cells are preferably isolated from, or alternatively have the characteristics of a cell isolated from the gastrointestinal tract of the animal of interest. For example, the cells can be isolated from the stomach, the small intestine, or the large intestine, including from any subpart of these organs. In some preferred embodiments, the cells are intestinal cells, particularly intestinal epithelial cells. In some preferred embodiments, the cells are intestinal cell lines, which can be neoplastically transformed, or otherwise immortalized. In highly preferred embodiments, the cells are Caco-2 cells, C2BBe1 cells, HT-29 cells, or T-84 cells.

Transcellular transport of the test compound in any of the first, second, third, or more cells can be measured according to any means suitable in the art. Transepithelial electrical resistance (TEER) measurements, which are routinely carried out, can also be used. Liquid chromatography-mass spectrometry (LC-MS) and LC-tandem mass spectrometry (LC-MS-MS) can be used (van Breemen R B, et al. (2005) Expert Opin. Drug Metab. Toxicol. 1:175-85). In addition, fluorescent dyes or radioisotope can be used, for example, by tagging the test compound with an acceptable dye or isotope as the labels can be conveniently detected by fluorescence or liquid scintillation counting. Non-limiting examples include fluorescent Rhodamine 123, and radiolabeled cyclosporine A, digoxin, ritonavir, taxol, verapamil, and vinblastine (Troutman M T (2003) Pharm. Res. 20:1210-24).

Unidirectional (mucosal-to-serosal transport) or bidirectional (mucosal-to-serosal and serosal-to-mucosal transport) permeability of the cells can be measured. In the unidirectional transport, a drug solution is added to the apical (mucosal) side of the cell monolayers, samples are collected from the basolateral (serosal) side, and a permeability coefficient is determined by the accumulative drug transported across divided by the time, surface area and dose concentration. In the bidirectional transport, both permeability coefficients in apical-to-basolateral (mucosal-to-serosal) and basolateral-to-apical (serosal-to-mucosal) directions are determined. Several mammalian epithelial cell lines plated onto the upper well of dual well tissue culture plates have been used for the purpose of studying the permeability and transport of various chemicals, including drugs, toxins and nutrients (Weinstein K et al. in "Pharmaceutical Profiling in Drug Discovery for Lead Selection", R.T. Borchardt, E. H. Kerns, C. A. Lipinski, D. R. Thakker and B. Wang, eds., pp 217-234, Am. Assoc. Pharm. Scientists, Arlington, Va., 2004. J. Polli and C. Serabjit-Singh, ibid, pp 235-255.)

Measurements of the transcellular transport of the test compound can be directly compared with reference values for the transcellular transport, i.e., gastrointestinal absorption rate, efficiency, capacity, etc., of compounds in which transcellular transport has been previously characterized. For example, measurements obtained from the test compound can be compared to reference values for compounds with no gastrointestinal absorption, with low gastrointestinal absorption, with moderate gastrointestinal absorption, with high gastrointestinal absorption, or with any combination of such reference values. Non-limiting examples of such reference values are provided by Table 2 (Artursson P. et al. (1991) Biochem. Biophys. Res. Commun 175:880-5).

TABLE 2

Correlation of C2BBe1 permeability and absorption in human cells

| Drug | $P_{app}$ in C2BBE1 cells ($10^{-6}$ cm/s) | % Absorption in human |
|---|---|---|
| Corticosterone | 54.5 | 100 |
| Testosterone | 51.8 | 100 |
| Propranolol | 41.9 | 90 |
| Alprenolol | 40.5 | 93 |
| Warfarin | 38.3 | 98 |
| Metoptolol | 27 | 95 |
| Felodipine | 22.7 | 100 |
| Hydrocortisone | 21.5 | 89 |
| Dexamethasone | 12.5 | 100 |
| Salicylic acid | 11.9 | 100 |
| Acetylsalicylic acid | 2.4 | 100 |
| Practolol | 0.9 | 100 |
| Terbutaline | 0.38 | 73 |
| Atenolol | 0.2 | 50 |
| Mannitol | 0.18 | 16 |
| Arginine-vasopressin | 0.14 | 0 |
| Sulphasalazine | 0.13 | 13 |
| 1-Deamino-8-D-arginine | 0.13 | 1 |
| Olsalazine | 0.11 | 2 |
| Polyethylene glycol | 0.052 | 0 |

The test compound measurement values experimentally obtained relative to the reference values is indicative, and at least predictive, of the test compound's absorption in the gastrointestinal tract of the animal of interest. It is contemplated that compounds characterized according to the methods of the invention can serve as reference compounds, representing the relative degree of gastrointestinal absorption, against which additional test compounds can be compared.

The invention also features methods for inhibiting the expression of membrane efflux transport proteins in cells. In some embodiments, the methods comprise stably transforming a cell with a nucleic acid molecule that interferes with the expression of the membrane efflux transport protein. The nucleic acid molecule can inhibit the expression by inhibiting the transcription of the gene encoding the membrane efflux transport protein, or can inhibit the expression by inhibiting the translation of mRNA into the protein.

The nucleic acid molecule can be any regulatory gene or fragment of a gene whose expression or presence in the cell inhibits transcription or translation of the efflux transport protein gene product. In preferred embodiments, the nucleic acid molecule is RNA. In more preferred embodiments, the nucleic acid molecule is interfering RNA, and is preferably double stranded. Non-limiting examples of interfering RNA include siRNA and shRNA.

It has been discovered in accordance with the present invention that certain individual nucleic acid molecules can inhibit the expression of two or more membrane efflux transport proteins. Accordingly, such nucleic acid molecules can be advantageously used in any of the inventive methods described and exemplified herein. A non-limiting example of an individual nucleic acid molecule that can inhibit two or more membrane efflux transport proteins is SEQ ID NO: 25. This nucleic acid molecule has been demonstrated to inhibit the expression of at least both BCRP and MRP2. The observation that a single nucleic acid molecule can inhibit two or more membrane efflux transport proteins represents a significant advance for the determination of the relative contribution of select membrane efflux transport proteins on cellular absorption and transport of compounds.

A cell can be transformed with such nucleic acid molecules according to any means available in the art such as those describe or exemplified herein. It is preferred that cells are stably transformed with a vector comprising a nucleic acid sequence encoding such regulatory nucleic acid molecules. Any vector suitable for transformation of the particular cell of interest can be used in the present invention. In preferred embodiments, the vector is a viral vector. In more preferred embodiments, the vector is a lentivirus vector.

The regulatory nucleic acid molecule can comprise any sequence complementary to, or otherwise amenable to hybridization to and/or interference with the expression of a gene encoding the membrane efflux transport protein of interest. Non-limiting examples of such nucleic acid sequences include SEQ ID NOs: 1, 2, 3, 4, 5, 17, 18, 19, 20, 21, 22, 23, 24, 25, and 26, and allelic variants thereof. Preferred, but non-limiting examples of membrane efflux transport proteins include P-glycoprotein, Multidrug Resistance-Associated Protein-2, and Breast Cancer Resistance Protein.

Preferred cells that can be targeted for modulation, particularly inhibition, of the expression of membrane efflux transport proteins can be any cell that expresses such transport proteins. Such cells can express the transport proteins naturally, or the cells can be engineered to express the transport proteins. The cells can be isolated fresh from a host organism, or can be cell lines. It is preferred that such cells be of a gastrointestinal lineage, and it is particularly preferred that such cells be intestinal epithelial cells. Non-limiting examples of cell lines amenable to genetic regulation according to the inventive methods include Caco-2 cells, C2BBe1 cells, HT-29 cells, T-84 cells, and HRT-18 cells.

The invention also features isolated nucleic acid molecules for the genetic regulation of membrane efflux transport expression. Considered in terms of their sequences, the nucleic acid molecules of the invention that encode regulatory, particularly inhibitory, sequences include SEQ ID NOs: 1, 2, 3, 4, 5, 17, 18, 19, 20, 21, 22, 23, 24, 25, and 26, and allelic variants, homologs, and natural mutants of SEQ ID NOs: 1, 2, 3, 4, 5, 17, 18, 19, 20, 21, 22, 23, 24, 25, and 26. Because such variants and homologs are expected to possess certain differences in nucleotide sequence, this invention provides isolated polynucleotides that have at least about 60%, preferably at least about 61%, 62%, 63%, 64%, 65%, 66%, 67%, 68%, 69% or 70%, more preferably at least about 71%, 72%, 73%, 74%, 75%, 76%, 77%. 78%, 79%, or 80%, even more preferably 81%, 82%, 83%, 84%, 85%, 86%, 87%, 88%, 89%, and even more preferably 90%, 91%, 92%, 93%, 94%, 95%, and most preferably 96%, 97%, 98% and 99% or more identity with any one of SEQ ID NOs: 1, 2, 3, 4, 5, 17, 18, 19, 20, 21, 22, 23, 24, 25, and 26. Because of the natural sequence variation likely to exist among genes encoding these regulatory sequences in different individuals, one skilled in the art would expect to find this level of variation, while still maintaining the unique properties of the polynucleotides of the present invention. Accordingly, such variants and homologs are considered substantially the same as one another and are included within the scope of the present invention.

Nucleic acid molecules of the invention may be prepared by two general methods: (1) they may be synthesized from appropriate nucleotide triphosphates, or (2) they may be isolated from biological sources. Both methods utilize protocols well known in the art.

The availability of nucleotide sequence information such as the entire nucleic acid sequence of the membrane efflux transport protein, for example, SEQ ID NOs: 6-8, enables preparation of an isolated nucleic acid molecule of the invention by oligonucleotide synthesis. Synthetic oligonucleotides may be prepared by the phosphoramadite method employed in the Applied Biosystems 38A DNA Synthesizer or similar devices. The resultant construct may be purified according to methods known in the art, such as high performance liquid chromatography (HPLC). A synthetic DNA molecule so constructed may then be cloned and amplified in an appropriate vector.

Nucleic acids of the present invention may be maintained as DNA in any convenient cloning vector. In a preferred embodiment, clones are maintained in plasmid cloning/expression vector, either of which can be propagated in a suitable prokaryotic or eukaryotic host cell.

Nucleic acid molecules of the invention include cDNA, genomic DNA, RNA, and fragments thereof which may be single-, double-, or even triple-stranded. Thus, this invention provides oligonucleotides (sense or antisense strands of DNA or RNA) having sequences capable of hybridizing with at least one sequence of a nucleic acid molecule of the present invention, in particular, SEQ ID NOs: 6-8. Such oligonucleotides are useful as probes for detecting genes encoding membrane efflux transport proteins, or for the positive or negative regulation of expression of genes encoding a membrane efflux transport protein at or before translation of the mRNA into proteins. Methods in which oligonucleotides or polynucleotides may be utilized as probes for such assays include, but are not limited to: (1) in situ hybridization; (2) Southern hybridization (3) northern hybridization; and (4) assorted amplification reactions such as polymerase chain reactions (PCR) and ligase chain reaction (LCR).

Also featured in accordance with the present invention are vectors and kits for producing transgenic host cells that comprise a polynucleotide encoding a regulatory sequence for inhibiting the expression of a membrane efflux transport protein, or homolog, analog or variant thereof in a sense or antisense orientation, or a construct under control of cell or tissue-specific promoters and/or other regulatory sequences. Such vectors are suitable for modulating, and preferably inhibiting, the expression of any membrane efflux transport protein. In preferred embodiments, the membrane efflux transport protein is P-glycoprotein, Multidrug Resistance-Associated Protein 2, or Breast Cancer Resistance Protein.

Suitable host cells include, but are not limited to, plant cells, bacterial cells, yeast and other fungal cells, insect cells and mammalian cells. More preferred are human cells. Even more preferred are human intestinal epithelial cells. Most preferred are Caco-2 cells, C2BBe1 cells, HT-29 cells, or T-84 cells.

Vectors for transforming a wide variety of these host cells are well known to those of skill in the art. They include, but are not limited to, plasmids, phagemids, cosmids, baculoviruses, bacmids, bacterial artificial chromosomes (BACs), yeast artificial chromosomes (YACs), as well as other bacterial, yeast and viral vectors. In preferred aspects of the invention, viral vectors are used. It is particularly preferred that lentiviral vectors are used.

Typically, kits for producing transgenic host cells will contain one or more appropriate vectors and instructions for producing the transgenic cells using the vector. Kits may further include one or more additional components, such as culture media for culturing the cells, reagents for performing transformation of the cells and reagents for testing the transgenic cells for gene expression or regulation, to name only a few.

In one embodiment, the coding region of the regulatory sequence is placed under a powerful constitutive promoter, such as the promoters for the following genes: hypoxanthine phosphoribosyl transferase (HPRT), adenosine deaminase, pyruvate kinase, β-actin, human myosin, human hemoglobin, human muscle creatine, and others. In addition, many viral promoters function constitutively in eukaryotic cells and are suitable for use in the present invention. Such viral promoters include without limitation, Cytomegalovirus (CMV) immediate early promoter, the early and late promoters of SV40, the Mouse Mammary Tumor Virus (MMTV) promoter, the long terminal repeats (LTRs) of Maloney leukemia virus, Human Immunodeficiency Virus (HIV), Epstein Barr Virus (EBV), Rous Sarcoma Virus (RSV), and other retroviruses, and the thymidine kinase promoter of Herpes Simplex Virus. Other promoters are known to those of ordinary skill in the art. In one embodiment, the coding region of the regulatory sequence is placed under an inducible promoter such as the metallothionein promoter, tetracycline-inducible promoter, doxycycline-inducible promoter, promoters that contain one or more interferon-stimulated response elements (ISRE) such as protein kinase R 2',5'-oligoadenylate synthetases, Mx genes, ADAR1, and the like. Other suitable inducible promoters will be known to those of skill in the art.

The vectors of the invention can be used to transform various cells with the various regulatory nucleic acid sequences of the invention. Thus, another aspect of the invention features host cells transformed with vectors comprising a nucleic acid sequence encoding a nucleic acid molecule for modulating, preferably inhibiting, the expression of a membrane efflux transport protein. Numerous techniques are known in the art for the introduction of foreign genes into cells and may be used to construct the recombinant cells for purposes of carrying out the inventive methods, in accordance with the various embodiments of the invention. The technique used should provide for the stable transfer of the heterologous gene sequence to the host cell, such that the heterologous gene sequence is heritable and expressible by the cell progeny, and so that the necessary development and physiological functions of the recipient cells are not disrupted. Techniques which may be used include, but are not limited to, chromosome transfer (e.g., cell fusion, chromosome-mediated gene transfer, micro cell-mediated gene transfer), physical methods (e.g., transfection, spheroplast fusion, microinjection, electroporation, liposome carrier), viral vector transfer (e.g., recombinant DNA viruses, recombinant RNA viruses) and the like (described in Cline M J (1985) Pharmac. Ther. 29:69-92). It is preferable that a viral vector be used to transform the cells of the invention. It is more preferable that the viral vector be a lentiviral vector.

Knockdown cells with inhibited expression of membrane efflux transport proteins can be created by inhibiting the translation of mRNA encoding the transport protein by "post-transcriptional gene silencing." The gene from the species targeted for down-regulation, or a fragment thereof, may be utilized to control the production of the encoded protein. Full-length antisense molecules can be used for this purpose. Alternatively, antisense oligonucleotides targeted to specific regions of the mRNA that are critical for translation may be utilized. The use of antisense molecules to decrease expression levels of a pre-determined gene is known in the art. Antisense molecules may be provided in situ by transforming cells with a DNA construct which, upon transcription, produces the antisense RNA sequences. Such constructs can be designed to produce full-length or partial antisense sequences. This gene silencing effect can be enhanced by transgenically over-producing both sense and antisense RNA of the gene coding sequence so that a high amount of dsRNA is produced (for example see Waterhouse et al. (1998) Proc. Natl. Acad. Sci. U.S.A. 95:13959-64). In this regard, dsRNA containing sequences that correspond to part or all of at least one intron have been found particularly effective. In one embodiment, part or all of the coding sequence antisense strand is expressed by a transgene. In another embodiment, hybridizing sense and antisense strands of part or all of the coding sequence for one or more membrane efflux transport proteins are transgenically expressed. Cells of the invention, C2BBE1 cells transduced with lentiviruses encoding interfering nucleic acid molecules (SEQ ID NOs: 1, 3, 21, 24, 25, and 26), have been placed with the Amer. Type Cult. Coll. (10801 University Blvd., Manassas, Va. 20110-2209) on Nov. 6, 2007 and have been assigned Access. Nos. PTA-8752, PTA-8753, PTA-8751, PTA-8754, and PTA-8755, respectively.

The invention also features kits for screening compounds for gastrointestinal absorption in animals. In some embodiments, the kits comprise a cell that has been transformed with at least one nucleic acid molecule that inhibits expression of at least one membrane efflux transport protein, as well as instructions for using the kit in a method for screening compounds for gastrointestinal absorption in animals. The kits of the invention can further comprise a second cell transformed with a nucleic acid molecule that interferes with the expression of a second membrane efflux transport protein. The kit of the invention can also further comprise a second and third cell transformed with a nucleic acid molecule that interferes with the expression of a second and third membrane efflux transport protein.

The cells of the kits can be Caco-2 cells, and preferably are C2BBe1 cells. However, any cell that stably expresses at least one membrane efflux transport protein of interest can be used. The cells can be transformed with any nucleic acid molecule that inhibits the expression of the membrane efflux transport protein of interest, such as but not limited to, those that are described and exemplified herein. For example, the nucleic acid molecule used to transform the cells can have at least one of SEQ ID NO: 1, 2, 3, 4, 5, 17, 18, 19, 20, 21, 22, 23, 24, 25, or 26, or allelic variants thereof.

In the inventive kits, the membrane efflux transport protein of interest whose expression is inhibited by transformation of the cell with the interfering nucleic acid can be any efflux transport protein known in the art, or later discovered. In preferred embodiments, the membrane efflux transport protein is at least one of P-glycoprotein, Multidrug Resistance-Associated Protein 2, or Breast Cancer Resistance Protein.

In some embodiments, the inventive kits comprise a cell that expresses a membrane transport efflux protein, a lentivirus vector for transformation of the cell, and optionally comprises at least one nucleic acid molecule that inhibits the expression of at least one membrane efflux transport protein expressed by the cell. For example, said nucleic acid molecule can be subcloned into the lentivirus vector, and the vector can be used to transform the cell. It is contemplated that any nucleic acid that can inhibit the expression of the membrane efflux transport protein can be subcloned into the lentivirus vector, and used to transform the cell to inhibit the expression of the efflux transport protein. The kits of this embodiment can comprise instructions for using the kit in a method for screening compounds for gastrointestinal absorption in animals. The instructions can also teach how to subclone an inhibitory nucleic acid into the lentivirus vector.

The invention also features methods for identifying compounds that inhibit the biological activity of a membrane efflux transport protein. It is preferred that the biological activity that is inhibited is the efflux activity of the transport protein. In some embodiments, the methods comprise inhibiting the expression of a membrane efflux transport protein in a first cell, contacting the first cell with a substrate of the membrane efflux transport protein, and determining the biological activity of the membrane efflux transport protein in the first cell. The methods also comprise contacting a second cell in which expression of the membrane efflux transport protein is not inhibited with a test compound and a substrate of the membrane efflux transport protein, and in parallel, contacting a second cell in which expression of the membrane efflux transport protein is not inhibited with a substrate of the membrane efflux transport protein, and determining the biological activity of the membrane efflux transport protein in the second cell in the presence and absence of the test compound. After the biological activity of the membrane transport protein is determined for the first cell, the second cell in the presence of the test compound, and the second cell in the absence of the test compound, the biological activities can be compared. A decrease in the biological activity in the second cell in the presence of the test compound relative to the biological activity in the second cell in the absence of the test compound, and at least partial identity of the determined value for the biological activity of the membrane transport protein in the second cell in the presence of the test compound with the determined value for the biological activity in the first cell is indicative that the test compound specifically inhibits the membrane efflux transport protein.

Genetic knockdown of the expression of membrane efflux transport proteins inhibits about 20% of the efflux activity of the transport protein, frequently inhibits about 50% of the activity, and can inhibit 80% or more of the activity, as exemplified herein. Thus, by "at least partial identity" it is meant that chemical inhibition of a transport protein by a test compound can match or exceed the levels of inhibition of efflux activity determined for knockdown cells, or can fall below the levels of inhibition the efflux activity of knockdown cells. Identity pertains to the inhibition of efflux activity. For illustration purposes, genetic inhibition of a first cell may provide for 90% inhibition of efflux activity in the first cell, relative to controls. In comparison, the test compound may provide for 80% inhibition of the efflux activity, relative to controls. Although the test compound in this scenario provides less inhibition than the genetic knockdown, the 80% inhibition provides at least partial identity to the 90% inhibition of the genetic knockdown. In this example, 90% inhibition by the test compound would be full or complete identity.

In some embodiments of the inventive methods, inhibiting the expression of a membrane efflux transport protein in the first cell comprises transforming the first cell with a nucleic acid molecule that interferes with the expression of the membrane efflux transport protein. The nucleic acid molecule can be an interfering nucleic acid molecule as described and exemplified herein. In preferred embodiments, the nucleic acid molecule is RNA, and in more preferred embodiments, the nucleic acid molecule comprises SEQ ID NO: 1, 2, 3, 4, 5, 17, 18, 19, 20, 21, 22, 23, 24, 25, or 26 or allelic variants thereof.

In some highly preferred embodiments, the membrane efflux transport protein of interest is P-glycoprotein, Multidrug Resistance-Associated Protein 2, or Breast Cancer Resistance Protein. The P-glycoprotein, Multidrug Resistance-Associated Protein 2, or Breast Cancer Resistance Protein can be the target of genetic knockdown in the first cell, and the target of chemical inhibition being screened for in the second cell. In some embodiments, the first cell or second cell is a Caco-2 cell, or a C2BBe1 cell, or combinations thereof.

Any known substrate of the membrane efflux transport protein of interest can be used in the screening methods. Non-limiting examples of such substrates include digoxin for P-glycoprotein, vinblastine or dinitrophenyl-5-glutathione for Multidrug Resistance-Associated Protein 2, and mitoxantrone or estrone-3-sulfate for Breast Cancer Resistance Protein.

In some aspects, the inventive test compound screening methods can be modified and adapted to screen for multiple test compounds. For example, two or more membrane efflux transport proteins can be inhibited in the first cell, and at least one, preferably two or more test compounds are contacted with the second cell. The biological activity, such as efflux activity, of each membrane efflux protein that is inhibited in the first cell, and that is expressed in the second cell is then determined in the presence or absence of a test compound, and the determined values of the biological activity are compared as described above. As such, a decrease in the biological activity in the second cell in the presence of the test compound(s) relative to the biological activity in the second cell in the absence of the test compound(s), and at least partial identity of the determined value for the biological activity of the membrane transport protein(s) in the second cell in the presence of the test compound(s) with the determined value for the biological activity in the first cell is indicative that the test compound(s) specifically inhibit(s) the membrane efflux transport protein(s).

Compounds identified by any of the foregoing inventive screening methods are contemplated to be within the scope of this invention. Such compounds are preferably inhibitors of membrane efflux transport proteins, and more preferably are inhibitors of P-gp, MRP2, or BCRP.

The following examples are provided to describe the invention in greater detail. They are intended to illustrate, not to limit, the invention.

EXAMPLE 1

General Experimental Procedures

Cell Line. The parental cell line, C2BBe1 (ATCC Accession Number CRL-2102), was used in the experiments described herein to evaluate absorption potential of candidate drug molecules. The C2BBe1 cell line was derived from the Caco-2 cell line in 1988 by limiting dilution. The clone was selected on the basis of morphological homogeneity and exclusive apical villin localization. C2BBe1 cells form a polarized monolayer with an apical brush border (BB) morphologically comparable to that of the human colon. Isolated BBs contain the microvillar proteins villin, fimbrin, sucrase-isomaltase, BB myosin-1, and the terminal web proteins fodrin and myosin II. The cells express substantial levels of BB myosin I similar to that of the human enterocyte. Although clonal, and far more homogeneous than the parental Caco-2 cell line with respect to BB expression, these cells are still heterogeneous for microvillar length, microvillar aggregation, and levels of expression of certain BB proteins.

Cell Seeding and Quality Control. Transwell® devices (Corning, Inc., Corning, N.Y.) containing monolayers of cells were prepared as follows: Up to one or two dozen 12-well Transwell® devices were prepared at one time from the same parent stock flask. Any cells not used for seeding Transwell® devices were recultured in T-150 stock tissue culture flasks. Each insert of a 12-well Transwell® device was pretreated with rat tail collagen to promote cell attachment. Then, 1.5 mL of cell culture media (90% Dulbecco's Modified Eagle Medium supplemented with 10% fetal bovine serum) was added to the bottom wells of a 12-well Transwell® device. The cells were detached from T-150 tissue culture flasks by trypsinization, and resuspended in cell culture media. Clumps of cells were broken up by repeated pipetting to generate a uniform suspension of cells. The number of cells in suspension was counted using a hemocytometer. Supplemental cell culture medium was added to the cell suspension to bring the cell count to approximately 136,000 cells per mL. 0.5 mL of cell suspension, containing approximately 68,000 cells, was added to each upper well of the 12-well Transwell® device. The cells were allowed to attach overnight and fed with fresh cell culture medium the following day by adding 0.5 mL of medium to the upper chamber and 1.5 mL of medium to the lower chamber of each well. Medium was changed every other day for at least 20 days prior to testing a randomly selected device from each lot for cell confluence and transporter function.

Quality control (QC) testing of a batch of Transwell® devices was carried out as follows: Randomly selected inserts from a batch of Transwell® devices were removed for the QC assay. The cells were placed in a blank Transwell® bottom plate containing Hank's Balanced Salt Solution (HBSS) pH 7.4 containing 10 mM HEPES and 15 mM glucose (HBSSg) pre-warmed to 37° C. The medium was aspirated from the wells and HBSSg was used to rinse the cell monolayers on the inserts. Fresh HBSSg was added after the monolayers were washed, the inserts were removed from the assay plate, and the transepithelial electrical resistance (TEER) value of the monolayers was determined using an ENDOHM transepithelial electrical resistance measurement apparatus (World Precision Instruments).

Monolayers having a TEER value above 100 ohm/cm$^2$ are considered acceptable for use in permeability studies. If the TEER value fell below this range, the rest of the batch was re-cultured with fresh medium for additional time and retested. If the batch failed three times, the entire batch was rejected. Sample wells from the batch that were above the acceptable limit were tested for permeability of reference compounds as follows: The following pre-warmed QC solution was added to the upper chamber of the Transwell® insert; 0.5 mM Lucifer Yellow, 10 µM Atenolol, 10 µM Propranolol, 10 µM Pindolol and 10 µM Digoxin in HBSSg pH 7.4±0.2. The bottom wells contained HBSSg pre-warmed to 37° C. The Transwell device was placed in a humidified incubator and incubated for 2 hours at 37° C. in an atmosphere containing 5% $CO_2$. At end of the incubation period, samples were withdrawn from the bottom well for analysis of Lucifer Yellow content by fluorescence detection, and the other compounds by LC/MS/MS.

Permeability values were calculated from the donor (upper well) concentrations and net increases in receiver (bottom well) concentrations at the 2 hour sampling interval. The permeability for the time interval, Papp (t1–t2), was calculated according to the following formula: $Papp(t1-t2) = ((Ct2-Ct1)/(t2-t1)) \times Vr/(A \times Cd)$. Ct2–Ct1 is the cumulative concentration difference in the receiver (bottom) compartment at each time interval in µM, (in this example Ct1 is assumed to be "0" because the entire time interval (120 min) is used in the calculation); Vr is the volume of the receiver compartment (in cm$^3$); A is the area of the cell monolayer (1.13 cm$^2$ for 12-well Transwell®), and Cd is concentration in the donor sample compartment (upper well) in µM, which is equal to the concentration in the donor solution described above. The apparent permeability for each compound used for QC purposes was the average of all Papp values calculated for all replicates tested, typically 3 replicate inserts per assay condition.

This assay was repeated by adding the QC solution to the bottom well of the Transwell® and measuring the digoxin concentration in the upper well after 2 hours. A calculated Papp for digoxin transport from the lower to the upper well that is at least 3 times higher than that calculated for transport from the upper to the lower well indicates functional expression of P-gp in the cell monolayers.

shRNA. To knockdown P-gp expression and activity in the C2BBe1 parental cell line, RNAi technology was used. The goal was long term silencing of the P-gp gene. Five 21 nucleotide shRNA duplexes (SEQ ID NOs: 1-5) from five different parts of the human P-gp genome (Gen Bank Accession No. NM_000927) were designed using the MISSION® search database of the Sigma-Aldrich™ website, which is produced and distributed under license from the Massachusetts Institute of Technology.

Calcein-AM assay. To determine activity of the P-gp protein, calcein-AM assays were conducted. Calcein-AM (3',6'-Di(O-acetyl-2',7'-bis[N,N-bis(carboxymethyl)-aminomethyl]fluorescein tetraacetoxymethyl ester) is a hydrophobic ester of the fluorescent molecule calcein. Calcein-AM is converted to the fluorescent parent calcein by intracellular sterases. Calcein-AM is also a substrate of P-gp (U.S. Pat. No. 5,872,014). Calcein-AM cannot readily enter cells when P-gp is present in the cell membrane and functional. However, when P-gp is not present or not functional, calcein-AM can readily enter a cell and be quickly converted to its fluorescent counterpart, calcein. Therefore, in the calcein-AM assay, high intracellular fluorescence is an indication of low P-gp expression or function.

To determine the P-gp activity, cells were plated in 96-well tissue culture plates and cultured for 48. After 48 hours, cell culture media was removed and the cells were washed with phosphate buffered saline solution (PBS). After washing, cells were incubated with 1 µM calcein-AM for 30 minutes. Parental cells treated with Cyclosporin A, an established P-gp inhibitor, were used as a positive control to verify the P-gp inhibition increased the intracellular fluorescence in parental cell lines. After incubation with calcein-AM, the cells were rinsed with fresh control buffer and fluorescence was measured using a Fluo-star fluorescence plate reader (BMG Lab Technologies, NC) with excitation and emission filters set at wavelengths of 485 nm and 538 nm, respectively.

RT-PCR. Total RNA was extracted from cells according to the following protocol. Cells were harvested from culture by centrifugation, resuspended in 1 ml of TRIzol® reagent (Invitrogen, Carlsbad, Calif.), and incubated at room temperature for 5 minutes with gentle shaking. The suspension was transferred to a 1.5 ml centrifuge tube, to which 200 µl of Chloroform was added, followed by an additional 5 minute incubation period with shaking. After incubation, the suspension was centrifuged at 12,000×g for 12 minutes at 4° C. The supernatant was transferred to a fresh, sterile 1.5 ml centrifuge tube, and supplemented with 0.5 ml of 2-propanol per 1 ml of TRIzol reagent, and incubated for 10 minutes at room temperature. The mixture was then centrifuged at 12,000×g for an additional 12 minutes at 4° C. After centrifugation, the supernatant was removed and the pellet was washed with 75% ethanol. The sample was re-centrifuged at 7500×g for 5 minutes at 4° C., followed by the removal of the supernatant. The pellet was allowed to air dry at room temperature. The pellet was resuspended in pre-warmed (55° C.) nuclease-free water, and incubated at 55° C. for 10 minutes. RNA yield and purity were quantified by absorbance at 260 nm and 280 nm.

RT-PCR mixtures were set up as 50 µl samples containing buffer, 1-2 µg of RNA, 10 µM of Forward primer, 10 µM of Reverse primer, Taq polymerase, and water. Primers to amplify human P-gylcoprotein were as follows: P-gp Forward 5'-GCTCCTGACTATGCCAAAGC-3' (SEQ ID NO: 9); and, P-gp Reverse 5'-TCTTCACCTCCAGGCTCAGT-3' (SEQ ID NO: 10). Primers to amplify human MRP2 were as follows: MRP2 Forward 5'-CTGGTTGGGAACCT-GACTGT-3' (SEQ ID NO: 11); and, MRP2 Reverse 5'-CAA-CAGCCACAATGTTGGTC-3' (SEQ ID NO: 12). Primes to amplify human BCRP were as follows: BCRP Forward 5'-GTGGCCTTGGCTTGTATGAT 3' (SEQ ID NO: 13); and, BCRP Reverse 5'-GATGGCAAGGGAACAGAAAA 3' (SEQ ID NO: 14). Human β-actin was amplified in parallel as a positive control using the following primers: β-actin Forward 5'-ACTATCGGCAATGAGCGGTTC-3' (SEQ ID NO: 15); and, β-actin Reverse 5'-AGAGCCACCAATCCACA-CAGA-3' (SEQ ID NO: 16).

The PCR cycles proceeded in a programmable thermocycler with the following parameters: cDNA synthesis, 1 cycle, 55° C. for 30 minutes; denaturation, 1 cycle, 94° C. for 2 minutes; PCR amplification, 40 cycles of 94° C. for 15 seconds, 62° C. for 30 seconds, 72° C. for 1 minute; and, final extension, 1 cycle, 72° C. for 5 minutes. Amplification was confirmed by electrophoresis in 2% agarose gels.

Western Blotting. Cellular monolayers were grown to confluency in 90% DMEM+10% FBS, media was removed, and monolayers were washed using 1×PBS. To lyse the cells, 500 µl of RIPA lysis buffer, 1× (Santa Crux Biotechnologies, CA, Cat #sc-24948), was applied to the cells and incubated on ice for 10 min. Lysed cells were harvested and centrifuged at 12,000×g 4° C. The supernatant/protein lysate was transferred to a clean tube, and the protein concentration was determined following the protocol of the BCA protein assay kit (Pierce, Ill., Cat #23225).

Protein extracts were subject to SDS PAGE as follows. About 25 to 50 µg of protein sample was loaded onto 8% SDS polyacrylamide gels, and run at 130 volts for 1 hour. Following electrophoresis, proteins were transferred to PVDF membranes using a BioRad MiniProtean 3 electrophoresis cell following a protocol provided by Bio-Rad.

After the proteins were transferred, the membranes were blocked with 0.2% Iblock solution (Applied Biosystems, CA. catalog #T2015) in Tris-Buffered Saline (TBS) containing 0.05% Tween-20™ (TBST) for 1 hour. Blocked membranes were incubated with primary antibody; for P-gp mouse anti-human P-gp, C494, Abcam, Cambridge, Mass., catalog# ab2265 diluted 1:500 in blocking solution overnight at 4° C.; for MRP2 polyclonal rabbit anti-human MRP2 antibody (Abcam, Cambridge, Mass., Cat# 50213) diluted 1:1,000 and; for BCRP mouse anti-human BCRP antibody (Abcam, Cambridge, Mass., Cat# ab3380). Unbound antibody was removed by washing 3× in TBST. After washing, the membranes were reacted with the secondary antibody, goat anti-mouse IgG linked to horse radish peroxidase, (goat anti-mouse IgG-HRP, Chemicon catalog #AP124) diluted 1:25,000 in block solution for 1 hour. Unbound secondary antibody was removed by washing 3 times with TBST. Bound antibody was visualized using Super Signal West Femto Chemiluminescent Substrate (Pierce, catalog #34094), and viewed with Epi Chem II darkroom from UVP, Inc (Upland, Calif.) following the manufacturer's protocols.

Bidirectional Transcellular Transport assay. Cell monolayers were grown to confluence (approximately 20 to 28 days after seeding) on collagen-coated, microporous, polycarbonate membranes in 12-well Costar Transwell® plates containing 90% DMEM+10% FBS in the top and bottom wells. Growth medium was changed every two to three days. Spent medium was removed by aspiration, and fresh medium was added to each of the wells. All wells were given fresh medium the day prior to the transport assays. Plates were certified as meeting in-house acceptance criteria prior to studies with test compounds. Details of the plates used and their certification are shown in the examples below. Plate certification using reference compounds was performed using Hank's Balanced Salt Solution containing 10 mM HEPES and 15 mM glucose at a pH of 7.4±0.1.

The permeability assay buffer for the test articles was Hank's Balanced Salt Solution containing 10 mM HEPES, 15 mM glucose, at a pH of 7.4±0.1. The dosing solution concentrations in assay buffer varied with the test compound. Typical concentrations of test compound were 10 µM in Hank's Balanced Salt Solution containing 10 mM HEPES, 15 mM glucose, at a pH of 7.4±0.1. At each time point, 1 and 2 hours, a 200-µL aliquot was taken from the receiver chamber (the bottom or basolateral chamber for apical to basolateral [A-to-B] permeability determinations or the top or apical chamber for basolateral to apical permeability [B-to-A] determinations) and replaced with fresh assay buffer. Cells were dosed on the apical side (A-to-B) or basolateral side (B-to-A) and incubated at 37° C. with 5% $CO_2$ and 90% relative humidity. Each determination was performed in duplicate. The permeability of Lucifer Yellow, a monolayer integrity marker compound, was also measured for each monolayer using a fluorescence assay. Lucifer Yellow Papp values are examined to determine whether monolayer integrity was impaired during the permeation study. Monolayers exhibiting abnormally high Lucifer Yellow permeability values were excluded from further analysis. All other compounds were assayed by LC/MS using electrospray ionization as summarized below.

The apparent permeability, Papp, and percent recovery were calculated according to the following formulas:

$$Papp = (dCr/dt) \times Vr/(A \times Cd0)$$

$$\text{Percent Recovery} = 100 \times (((Vr \times Cr\text{final}) + (Vd \times Cd\text{final}))/(Vd \times Cd0))$$

where, dCr/dt is cumulative concentration in the receiver compartment versus time; Vr is the volume of the receiver compartment in $cm^3$; Vd is the volume of the donor compartment in $cm^3$; A is the area of the cell monolayer (1.13 $cm^2$ for 12-well Transwell); Cd0 is the concentration of the dosing solution at time 0; Crfinal is the cumulative receiver concentration at the end of the incubation period; and, Cdfinal is the concentration of the donor at the end of the incubation period.

Summary of LC/MS Analytical Methods. A liquid chromatography instrument (LC) capable of generating a gradient of eluting buffer (mobile) phase was used. A chromatography column (Keystone Hypersil BDS C18 30×2.0 mm i.d., 3 μm, with guard column) was connected to the LC, and a 10 μL sample of buffer from the transport assay was injected into the column by the autosampler connected to the LC. Two mobile phases were continuously mixed in various proportions to establish a compositional gradient. Typical mobile phases used for this assay are an aqueous buffer, such as 25 mM Ammonium Formate Buffer, pH 3.5, and an organic solvent, such as acetonitrile. The elution gradient was formed by mixing appropriate proportions of mobile phases from two mobile phase reservoirs. In the example listed below, one reservoir contained the aqueous buffer and the second reservoir contained a mixture of acetonitrile and aqueous buffer in the proportion of 9:1 (volume:volume). The gradient program in the LC can be set to form a variety of gradients from linear, in which the composition changes from buffer to acetonitrile plus buffer at a fixed rate, to ballistic, in which the composition changes suddenly from buffer to acetonitrile plus buffer at a specific time in the analysis. Gradient program conditions for the analysis used herein are listed in Table 3, in which % A refers to the fraction of aqueous buffer in the gradient and % B refers to the fraction of acetonitrile-buffer mixture in the gradient. The time column refers to the time after the sample is injected with 0.0 minutes being the sample injection point. In this example the gradient is a ballistic gradient, suddenly changing composition at 1.5 minutes after sample injection.

TABLE 3

LC gradient program conditions

| Time (Min) | % A | % B |
|---|---|---|
| 0.0 | 100 | 0 |
| 0.5 | 100 | 0 |
| 1.5 | 0 | 100 |
| 2.0 | 0 | 100 |
| 2.1 | 100 | 0 |
| 3.5 | 100 | 0 |

The LC autosampler syringe was rinsed with 0.2% formic acid in water/acetonitrile/2-propanol: 1/1/1 (v/v/v) between injections.

The eluant from the chromatographic column was directed to the electrospray interface of a triple quadropole mass spectrometer (MS/MS), where the solvent and buffer were evaporated, and compounds eluted from the chromatographic column were ionized to form positive or negative ions.

In the examples below an instrument, typically a PE SCIEX API 2000, 3000 or in some cases a 4000 model, was used to separate and detect the ions. Triple quadropole instruments, such as these, can separate parent ions using the first quadropole magnetic, fragment them in the second quadropole chamber and detect specific fragments of the parent ion using the third quadropole to focus ions of a pre-specified mass onto the instrument's detector. This mode of detection is frequently referred to as Multiple Reaction Monitoring or MRM. MRM permits very specific and sensitive detection of compounds of interest with mass resolutions of at least ±1 atomic mass units and limits of detection in the nanogram per milliliter range.

Typical parent and fragment ions used for detection of the compounds mentioned in the examples are presented in Table 4.

TABLE 4

Parent and fragment ions used for detection

| Compound | Q1/Q3 |
|---|---|
| Atenolol | +267.4/145.2 |
| Propanolol | +260.4/116.2 |
| Pindolol | +249.3/116.2 |
| Digoxin | +798.6/651.5 |

Q1 refers to the mass selection setting of the first quadropole magnet and Q3 refers to the mass selection setting of the second quadropole magnet. The "+" sign refers to the sign of the charge on the ions being monitored.

Another parameter that can be adjusted on these mass spectrometers is the dwell time, which refers to the time period in which the two quadropoles are set to select and detect a particular combination of parent and fragment (daughter) ions. Multiple compounds can be detected in the same chromatographic analysis by appropriate adjustment of the chromatographic conditions and the mass spectrometer dwell times. Typical dwell times range from about 10 to about 100 milliseconds per ion pair combination. Skilled analysts can usually determine a combination of chromatographic conditions and dwell times that will allow detection and quantification of up to about 6 compounds in the same sample, provided that their ion masses differ by at least 5 atomic mass units.

Analytical standards with concentrations ranging from about 1 ng/mL up to about 1,000 ng/mL were prepared in the same matrix as used for transport assay samples. A standard curve was prepared by plotting the MS/MS detector response versus the standard concentration. The standard curve was fitted to a linear or polynomial response curve using software provided by the instrument manufacturer. The concentration of compound in the unknowns was determined by back calculating from the detector response. Alternatively, the ratio of detector responses between the compounds of interest and a reference standard compound added to the standards and samples at a fixed concentration is used to construct the standard curve and quantify unknowns. This is known as the internal standard method of sample quantification.

EXAMPLE 2

Transduction of C2BBe1 Cells with Interfering Nucleic Acid Sequences

Interfering nucleic acid sequences were subcloned into MISSION™ shRNA Human Tumor Suppressor Lentiviral Transduction Particles (Sigma-Aldrich, St. Louis, Mo.). Lentiviruses containing the interfering sequences (SEQ ID NOs 1, 2, 3, 4, or 5) were used to transduce C2BBe1 cells according to the manufacturer's protocols. In brief, C2BBe1 cells were seeded into a 96 well plate at $1.6 \times 10^4$ cells per well in cell culture media (90% DMEM+10% FBS), and incubated at 37° C. for 24 hours prior to transduction. On the day of transduction, media was removed from the wells and lentiviral particles were added to the wells at 0.5, 1.0, or 5.0 MOI (multiplicity of infection) and incubated with the cells for 24 hours at 37° C. Media containing unbound lentiviral particles was removed after this incubation, and fresh media was supplied. At 48 hours post-transduction, selective medium containing 10 μg/mL puromycin was added and changed every 3-4 days thereafter to select for transduced cells. Five puromycin-resistant isolates generated at an MOI of 1.0 were prepared as individual cell clones, giving rise to shRNA/P-gp clones #83, 84, 85, 86, and 87 (these clones correspond to transduction with lentiviruses containing SEQ ID NOs 1, 2, 3, 4, or 5, respectively). Each of the five cell clones were expanded and evaluated using the various assays described herein. shRNA/P-gp clones #83 and 85 have been placed with the Amer. Type Cult. Coll. (10801 University Blvd., Manassas, Va. 20110-2209) on Nov. 6, 2007 and have been assigned Access. No. PTA-8752 and Access. No. PTA-8753, respectively.

EXAMPLE 3

P-gp Gene Expression in shRNA/P-gp Clone Cells

Figure 2:
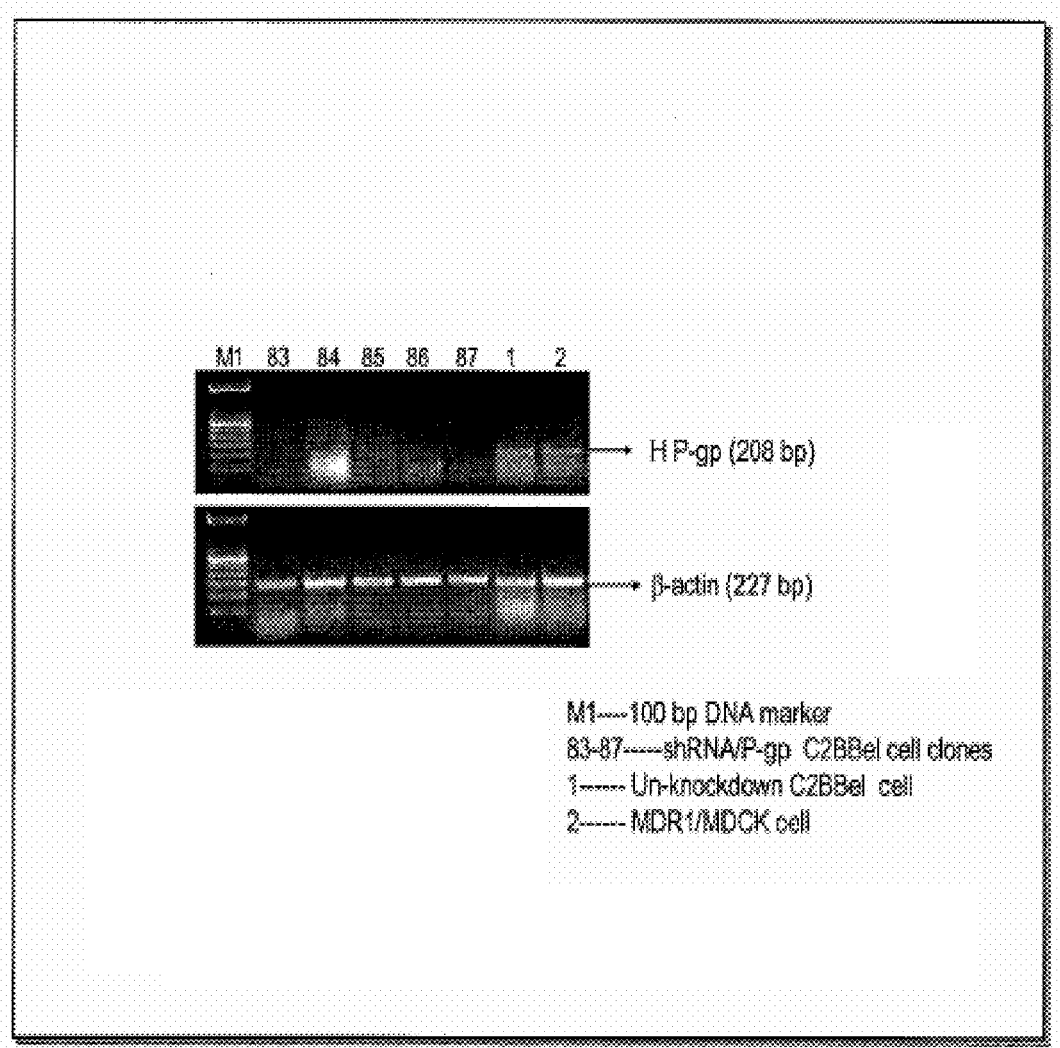
FIG. 2 shows gel electrophoretic analysis of RT-PCR amplified human P-gp mRNA from shRNA/P-gp clone cells and control cells. Non-transduced C2BBe1 (un-knockdown C2BBE1 cells) and MDR1/MDCK cells, shown in lanes labeled 1 and 2, respectively, prominently display a 208 base pair (bp) band corresponding to P-gp (top panel). In contrast, cells transduced with lentiviruses containing SEQ ID NOs: 1, 2, 3, 4, or 5 (shRNA/P-gp 83, 84, 85, 86, or 87, respectively) show significantly reduced expression of P-gp mRNA. β-actin is shown as a positive control (bottom panel). M1=100 by DNA marker.

Gene expression of P-gp in knockdown cells (shRNA/P-gp clones #83, 84, 85, 86, and 87) was determined by observing P-gp mRNA content, protein content and protein functional activity. RT-PCR was used to determine the expression of the P-gp mRNA. Total cellular RNA was harvested and amplified using primers specific to P-gp mRNA. RT-PCR products were then separated by electrophoresis on a 2% agarose gel. It was determined that 4 of the 5 shRNA/P-gp clone cells contained substantially less P-gp mRNA than control C2BBe1 cells (FIG. 2, top panel). β-actin was amplified, in parallel, as a positive control, and its expression was not affected by the interfering shRNA (FIG. 2, bottom panel).

The PCR result for clone 84 is confounded by the apparent presence of high amounts of primer dimmer in that gel lane. Calcein-AM assays indicate that P-gp function is knocked down in all 5 clones (FIG. 1). Functional assays measuring calcein-AM uptake indicate that the knockdown of P-gp mRNA occurred at around 80% to 90% efficiency for some transducants (FIG. 1).

Figure 3:
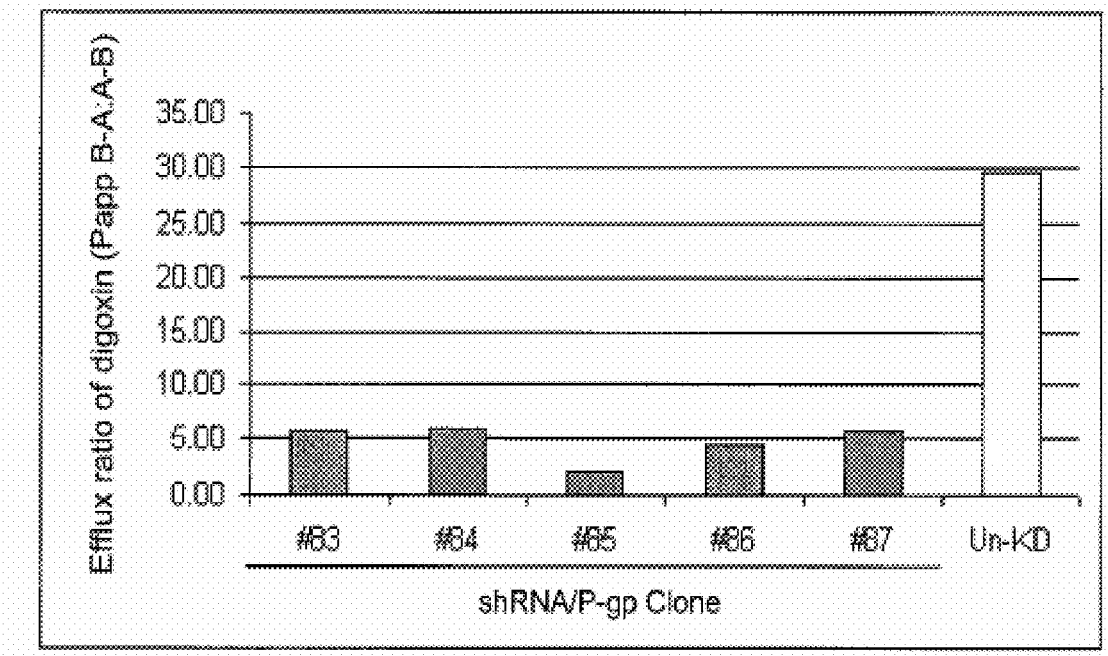
FIG. 3 shows the efflux ratio of digoxin in shRNA/P-gp clone cells. The efflux ratio (Papp B-A:A-B) is significantly reduced in cells transduced with lentiviruses containing SEQ ID NOs: 1, 2, 3, 4, or 5 (shRNA/P-gp 83, 84, 85, 86, or 87, respectively) relative to non-transformed C2BBe1 cells (Un-KD).

A bidirectional transport experiment was carried out to determine the efflux ratio of digoxin, a known P-gp substrate, on shRNA/P-gp clone cells. The results are shown in FIG. 3. Each of the shRNA/P-gp clone cells demonstrated an increase in apical to basal flux, and further demonstrated that the efflux ratio of Papp (B-A/A-B) was significantly lower than for un-knockdown control cells (Un-KD). The results confirm that P-gp efflux activity was inhibited by shRNAs targeted to the P-gp gene.

Figure 4:
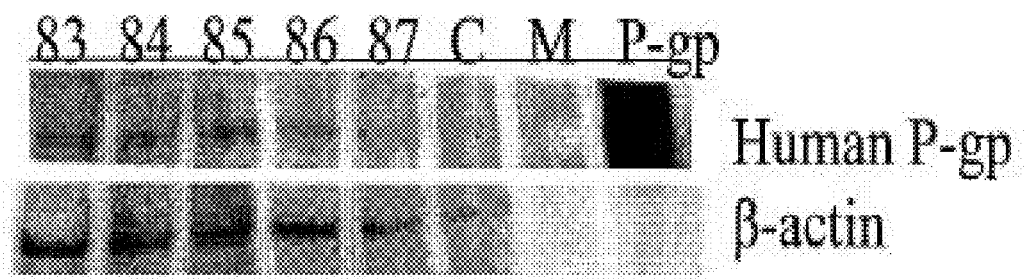
FIG. 4 shows a Western blot analysis of P-gp protein expression in C2BBe1 cells transduced with lentiviruses containing SEQ ID NOs: 1, 2, 3, 4, or 5 (shRNA/P-gp 83, 84, 85, 86, or 87, respectively). Transduced cells demonstrated significantly reduced P-gp protein expression relative to non-transduced C2BBe1 cells (C) run in parallel. P-gp expressed in insect cell microsomes was used as a positive control (P-gp). MDCK cell extract, which does not express human P-gp, was used as a negative control (M). β-actin was blotted as a standard for normalization of the amount of proteins transferred to the blotting membrane.
Figure 5:
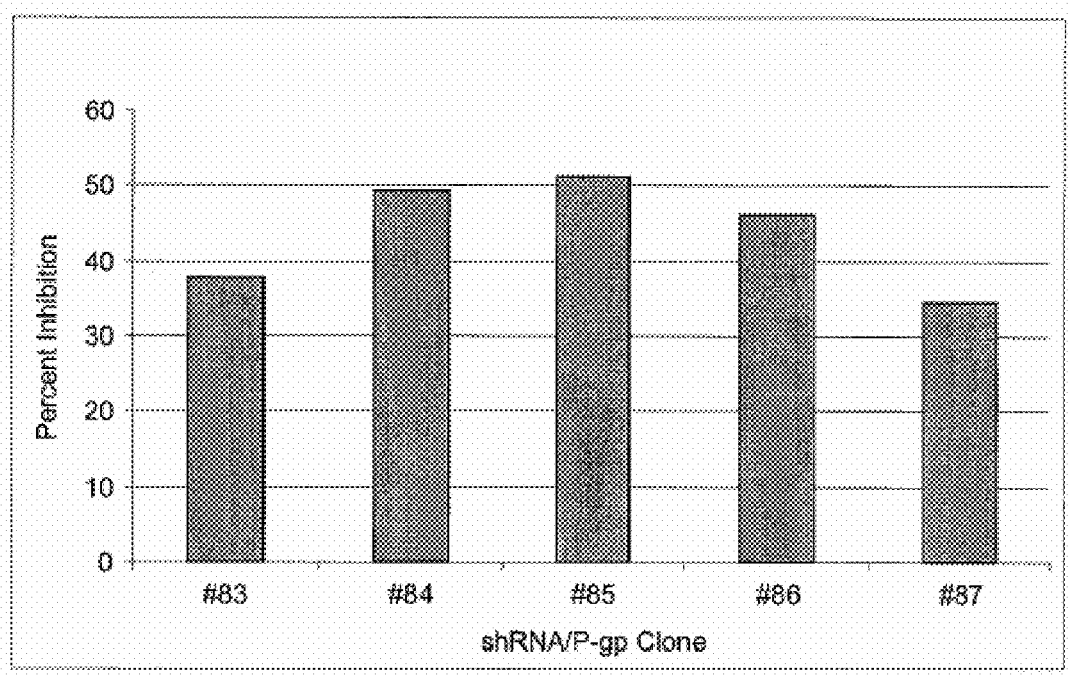
FIG. 5 shows the calculated percent inhibition of P-gp protein expression in C2BBe1 cells transduced with lentiviruses containing SEQ ID NOs: 1, 2, 3, 4, or 5 (shRNA/P-gp 83, 84, 85, 86, or 87, respectively), relative to non-transduced C2BBe1 cells, as determined by Western blot.

To further evaluate P-gp gene expression in shRNA/P-gp clone cells, protein was obtained from cell lysates, quantified, and separated on an 8% Precise® SDS-PAGE protein gel. After separation, proteins were transferred to a PVDF membrane and evaluated by immunoblotting as described in Example 1. After immunoblotting was complete, membranes were exposed to a chemiluminescent horseradish peroxidase substrate and protein content was visualized using a luminometer. As shown in FIG. 4, Western blot analysis indicated a substantial decrease in the amount of P-gp present in shRNA/P-gp clone cells, as compared to the control cells. Table 5 provides the optical density for each of the P-gp and β-actin bands on the Western blot shown in FIG. 4. The ratio of optical densities for P-gp and β-actin were calculated and used to determine percent knockdown. A graphical representation of the percent inhibition is provided in FIG. 5.

TABLE 5

Optical density for Western blot of knockdown P-gp expression in shRNA/P-gp C2BBe1 clone cells.

| Sample ID | Calibrate Value P-gp | Calibrate Value Actin | Ratio of P-gp/Actin | % of inhibition |
|---|---|---|---|---|
| shRNA/P-gp #83 | 1309 | 1474 | 0.89 | 37.71 |
| shRNA/P-gp #84 | 1240 | 1712 | 0.72 | 49.19 |
| shRNA/P-gp #85 | 1195 | 1716 | 0.70 | 51.11 |
| shRNA/P-gp #86 | 1052 | 1369 | 0.77 | 46.06 |
| shRNA/P-gp #87 | 967 | 1037 | 0.93 | 34.58 |
| C2BBe1 wild type | 958 | 672 | 1.42 | |

P-gp protein activity in shRNA/P-gp clone cells was determined using a calcein-AM assay as previously described in Example 1. Results are shown in FIG. 1. The results demonstrate that calcein fluorescence is substantially increased in all of the shRNA/P-gp genetic knockdown cells (KD), relative to the unknockdown control cells (Un-KD). Each shRNA chosen was able to significantly inhibit P-gp activity in the cells. In contrast with the results of the RT-PCR analysis, the calcein-AM assay results show that P-gp knockdown efficiency ranged from about 70% to about 90% among the different shRNAs. In parallel, shRNA/P-gp clone cells were also treated with a known chemical inhibitor of P-gp activity, cyclosporin A (CsA). In each of the different shRNA/P-gp clone cells tested, a small enhancement of calcein fluorescence, corresponding to an increase in P-gp inhibition, was observed upon treatment with CsA. Although none of the increases in fluorescence was determined to be statistically significant (Student's "t" test) over the genetic knockdown alone (FIG. 1), these results suggest that some residual P-gp activity remains.

EXAMPLE 4

Inhibition of MRP2 Expression in C2BBe1 Cells

For this example, gene expression of MRP2 in C2BBe1 cells was determined by observing both the MRP2 mRNA content as well as the protein content of the cells following viral transduction. To examine mRNA content, total cellular RNA was harvested and amplified by RT-PCR using primers specific to the MRP2 gene (SEQ ID NO: 11 and 12). The RT-PCR products were then analyzed after separation by electrophoresis on a 2% agarose gel.

To further evaluate MRP2 gene expression in MRP2 knockdown cells, cell lysates were obtained, their protein content quantified, and individual proteins separated on an 8% Precise® SDS-PAGE protein-separation gel as described in Example 1. After separation, proteins were transferred to a PVDF membrane and MRP2 was visualized by immunoblotting using 1:1000 dilution of rabbit anti-MRP2 (Abcam, Cambridge Mass., Cat# ab50213, Lot#351245). After immunoblotting, membranes were exposed to a chemiluminescent horseradish peroxidase substrate and band staining intensity was visualized using a luminometer. A decrease in band staining intensity by Western blot analysis would indicate a decrease in the amount of MRP2 protein present in MRP2 knockdown cells as compared to vector control cells.

Knockdown of MRP2 by Interfering RNA:

To target knockdown expression of MRP2, C2BBe1 cells were transduced with lentiviruses containing nucleic acid inserts SEQ ID NOs 17, 18, 19, 20, or 21, which encode interfering RNA. Our experiments indicated that shRNA targeted to MRP2 (shRNA/MRP2) required higher MOIs and longer incubation times with the lentivirus than shRNA targeted to BCRP (shRNA/BCRP) and P-gp (shRNA/P-gp) in order to achieve measurable MRP2 knockdown. After testing MOIs (multiplicity of infection) from 0.5 to 10, RT-PCR analysis showed that an MOI of 10 is optimal for high-efficiency MRP2 knockdown. The incubation time of shRNA/MRP2 viral particles also was extended to 2 days in the transduction experiments. All other experimental conditions were the same as described in Example 2.

Five puromycin-resistant isolates were prepared as individual cell clones, giving rise to shRNA/MRP2 clones #3, 4, 5, 6, and 7 (these clones correspond to transduction with lentiviruses containing SEQ ID NOs 17, 18, 19, 20, or 21, respectively). Each of the five cell clones were expanded and evaluated using the various assays described herein. shRNA/MRP2 clone #7 has been placed with the Amer. Type Cult. Coll. (10801 University Blvd., Manassas, Va. 20110-2209) on Nov. 6, 2007 and has been assigned Access. No. PTA-8751.

MRP2 Knockdown Results:

1.1 Expression of mRNA of MRP2 in Knockdown Clone Cells.

Figure 6:
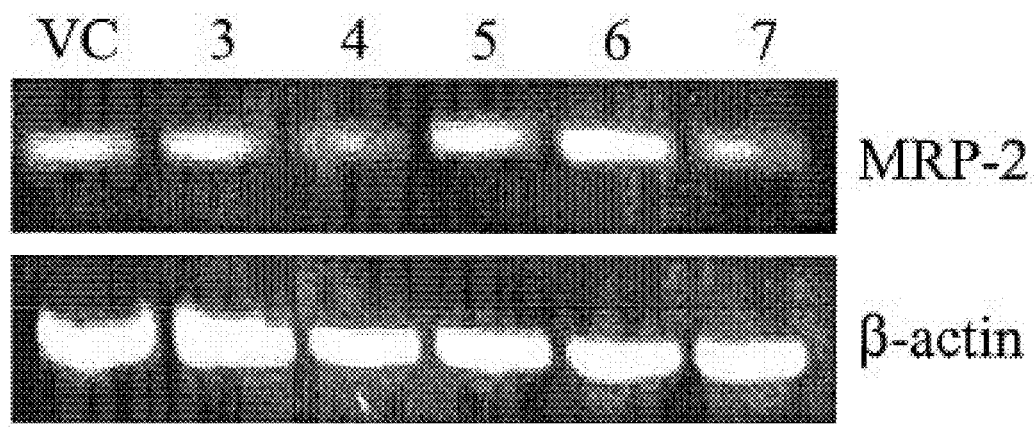
FIG. 6 shows MRP2 mRNA expression in C2BBe1 shRNA/MRP2 clone cells #3, 4, 5, 6, and 7 (transduced with SEQ ID NOs 17, 18, 19, 20, and 21, respectively). Vector control (VC) cells were transduced with a control shRNA vector described in Example 7. Total cellular RNA from cells with passages ranging from 2 to 5 was isolated after 5 to 7 days of growth, amplified with MRP2-specific primers (SEQ ID NOs: 11 and 12), and resolved by agarose gel electrophoresis. β-actin was included to account for varying efficiencies of total RNA extraction from the cell extracts.

FIG. 6 shows expression of MRP2 mRNA in C2BBe1 cells following viral transduction with shRNA/MRP2 sequences (SEQ ID NOs 17, 18, 19, 20, or 21, respectively). Vector control (VC) cells were prepared from cells transducted with lentiviruses encoding a non-interfering nucleic acid sequence (SEQ ID NO 27), as described in Example 7. Methods were described in Example 1. Total cellular RNA from cells with passage numbers ranging from 2 to 5 was isolated after 5 to 7 days of growth. Parallel RT-PCR results showed inhibition of expression of MRP2 mRNA in shRNA/MRP2 clones #3, #4 and #7 (FIG. 6). Analysis of the RT-PCR results based on the ratio of MRP2 mRNA band intensity to β-actin mRNA band intensity (see Table 6) indicated MRP2 mRNA expression was decreased from 15% to 19% by genetic MRP2 knockdown.

TABLE 6

Percent knockdown of MRP2 mRNA expression in C2BBe1 cells transduced with lentiviruses containing shRNA/MRP2 inserts.

| C2BBe1cell | Ratio of MRP2 band intensity to β-actin band intensity | Percent decrease in ratio compared to control |
|---|---|---|
| Vector Control | 0.67 | — |
| shRNA/MRP2 #3 | 0.57 | 15.12 |
| shRNA/MRP2 #4 | 0.57 | 15.31 |
| shRNA/MRP2 #5 | 0.63 | 6.04 |
| shRNA/MRP2 #6 | 0.72 | −7.59 |
| shRNA/MRP2 #7 | 0.54 | 19.53 |

1.2 Expression of Protein of MRP2 in shRNA/MRP2 Clone Cells.

Figure 7:
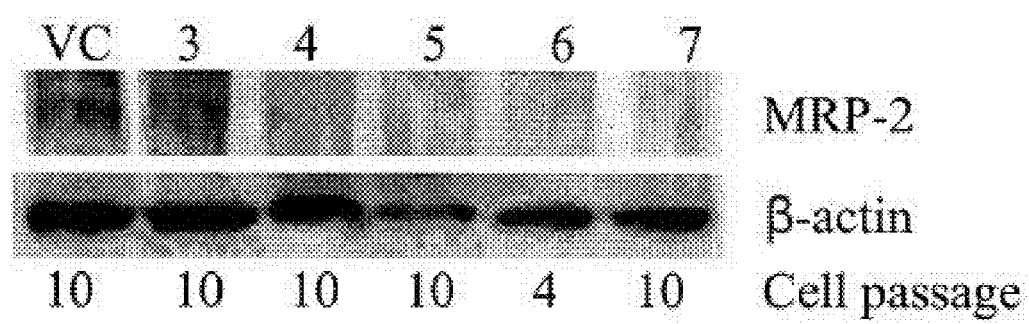
FIG. 7 shows Western blot analysis of MRP2 protein levels in C2BBe1 shRNA/MRP2 clone cells #3, 4, 5, 6, and 7 (transduced with SEQ ID NOs: 17, 18, 19, 20, and 21, respectively). Vector control (VC) cells were transduced with a control shRNA vector described in Example 7. The β-actin was included to account for variations in the amount of total protein applied to the electrophoresis gel.

Cell lysate content of MRP2 protein from shRNA/MRP2 clones cells and vector control cells was determined by Western blot analysis as described in Example 2. As seen in FIG. 7, Western blot analysis indicated a reduction of MRP2 protein in shRNA/MRP2 clones #4, 5, 6, and 7 when compared to vector control (VC) cells. Based on RT-PCR and Western blot results, C2BBe1 cells transduced with lentiviruses containing nucleic acid inserts corresponding to SEQ ID NO 21 (shRNA/MRP2 clone #7) showed the greatest degree of MRP2 knockdown of the 5 interfering sequences examined.

Functional knockdown of MRP2 will be assessed by measuring the bidirectional transport of one or more of the following compounds, known to be MRP2 substrates, across cell monolayers plated on Transwell® devices as described in Example 1: BCECF (2',7'-bis(2-carboxyethyl)-5(6)-carboxyfluorescein); Bilirubin-diglucuronide; BQ123 (cyclic pentapeptide, endothelin receptor antagonist); Chrysin; CPT11 (irinotecan); Furosemide; Genistin; Glutathione-S—S-glutathione; Glutathione-methylfluorescein; Grepafloxacin; Methotrexate; Nethylmaleimide-S-glutathione; SN 38 (CPT11 active metabolite); Sulfotaurolithocholic acid (STLC); Telmisaltan (BIBR 277) and its glucuronide metabolite; Temocaprilat; Vinblastine; Cisplatin or other established MRP2 substrates which show efflux across parental cell monolayers.

EXAMPLE 5

Inhibition of BCRP mRNA Expression and Activity in C2BBe1 Cells

1. Molecular Biological Characterization of BCRP mRNA Expression in BCRP Knockdown Cells Gene expression of BCRP in knockdown cells was determined by observing BCRP mRNA content, protein content and protein functional activity. The parental cell line, C2BBe1 (ATCC Accession Number CRL-2102), was used to evaluate genetic inhibition of BCRP expression by transformation of cells with lentiviral vectors encoding interfering RNA.

Five 21-nucleotide sequences (SEQ ID NOs: 22-26) targeting five different parts of the human BCRP gene (GeneBank Accession No. NM_004827) were designed using the MISSION® search database of the Sigma-Aldrich™ website, which is produced and distributed under a license from the Massachusetts Institute of Technology. Interfering nucleotide sequences were subcloned into MISSION® shRNA Lentiviral Transduction Particles (Sigma-Aldrich, St. Louis, Mo.), and used to transform C2BBe1 cells according to the general procedures set forth in Examples 1 and 2. Five stable shRNA/BCRP transformants, produced by transduction, at an MOI of 1.0, with lentiviruses containing SEQ ID NOs: 22, 23, 24, 25, or 26, were cloned, giving rise to shRNA/BCRP clones #798, 799, 800, 801, and 802, respectively. shRNA/BCRP clones #800 and 801 have been placed with the Amer. Type Cult. Coll. (10801 University Blvd., Manassas, Va. 20110-2209) on Nov. 6, 2007 and have been assigned Access. Nos. PTA-8754 and PTA-8755, respectively.

ShRNA/BCRP clones were evaluated for knockdown expression of the BCRP gene. Expression of BCRP was determined by observing BCRP mRNA content by RT-PCR amplification as described above, as well as by observing the protein content as measured by Western blotting.

Figure 8:
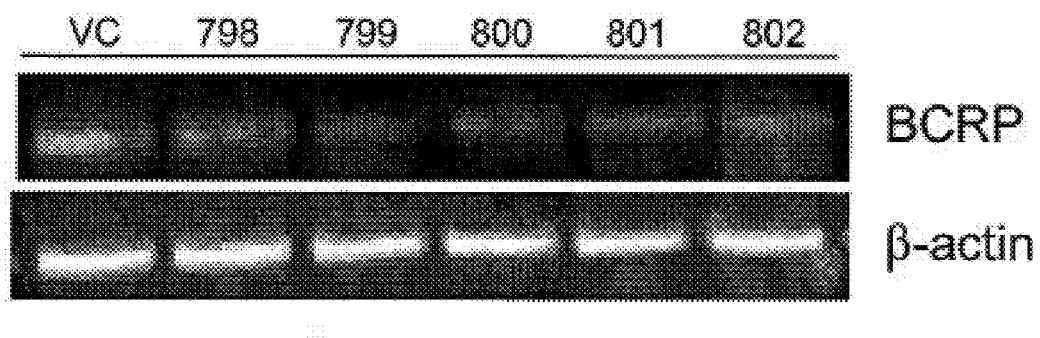
FIG. 8 shows BCRP mRNA expression in C2BBe1 cells transduced with lentiviruses containing SEQ ID NOs: 22, 23, 24, 25, or 26 (shRNA/BCRP 798, 799, 800, 801, or 802, respectively). Transduced C2BBe1 cells were cultured and grown, and total cellular RNA was extracted. Extracted RNA was amplified by RT-PCR with BCRP-specific primers (SEQ ID NOs: 13 and 14), and the products were resolved by agarose gel electrophoresis. All five shRNA/BCRP inserts significantly reduced BCRP mRNA expression relative to C2BBe1 cells transduced with a control lentivirus containing non-interfering shRNA (VC). β-actin mRNA production was also assessed to account for varying efficiencies of total RNA extraction from the cell extracts.
Figure 9:
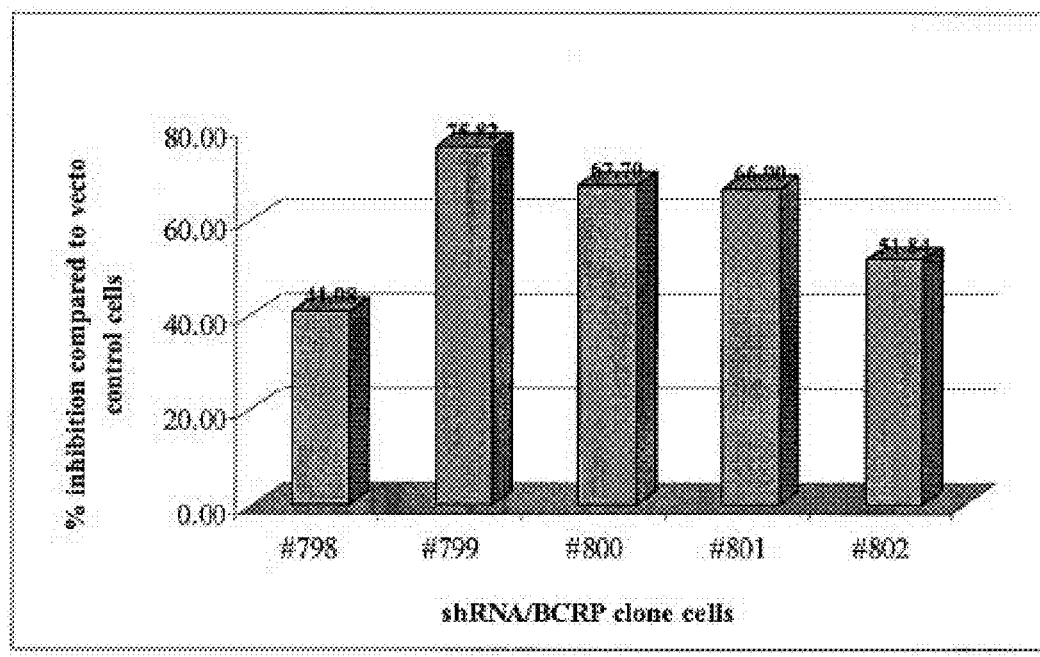
FIG. 9 shows relative levels of BCRP mRNA expression in C2BBe1 cells transduced with lentiviruses containing SEQ ID NOs: 22, 23, 24, 25, or 26 (shRNA/BCRP 798, 799, 800, 801, or 802, respectively). Transduced C2BBe1 cells were cultured and grown, and total cellular RNA was extracted. RT-PCR was carried out, and the products were resolved by agarose gel electrophoresis (FIG. 8). BCRP mRNA expression levels were compared with the level of BCRP mRNA expression in C2BBe1 cells transduced with a control lentivirus containing non-interfering shRNA (VC) to determine the degree of inhibition of BCRP mRNA expression caused by interfering shRNAs. Results are illustrated as percent inhibition of BCRP mRNA expression.

For RT-PCR, total cellular RNA was harvested as described in Examples 1 and 3 and amplified by RT-PCR using primers specific to BCRP mRNA (SEQ ID NOs: 13 and 14). The RT-PCR products were separated by electrophoresis on a 2% agarose gel and analyzed to determine whether shRNA/BCRP clone cells produced substantially less BCRP mRNA than C2BBe1 cells transduced with a non-interfering shRNA vector control. As shown in FIGS. 8 and 9, all five nucleic acid inserts specific for BCRP significantly reduced BCRP mRNA expression relative to the level expression observed for shRNA vector control C2BBe1 cells (VC). These results indicate that all five shRNA/BCRP clones inhibit production of BCRP mRNA.

Figure 10:
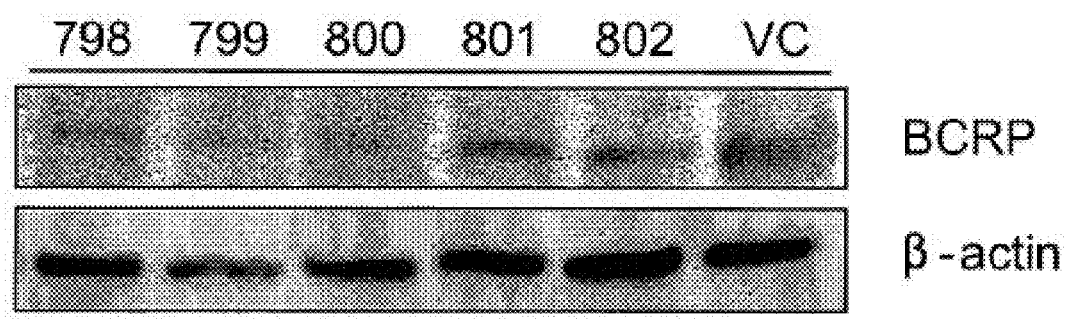
FIG. 10 shows expression of BCRP protein in C2BBe1 cells transduced with lentiviruses containing SEQ ID NOs: 22, 23, 24, 25, or 26 (shRNA/BCRP 798, 799, 800, 801, or 802, respectively). Western blot analysis indicated a substantial decrease in the amount of BCRP protein present in shRNA/BCRP clone cells #798, 799, 800, 801, and 802 (cell passage 15 to 16) as compared to C2BBe1 cells transduced with a control lentivirus containing non-interfering shRNA (VC). The β-actin was included to account for variations in the amount of total protein applied to the electrophoresis gel.
Figure 11:
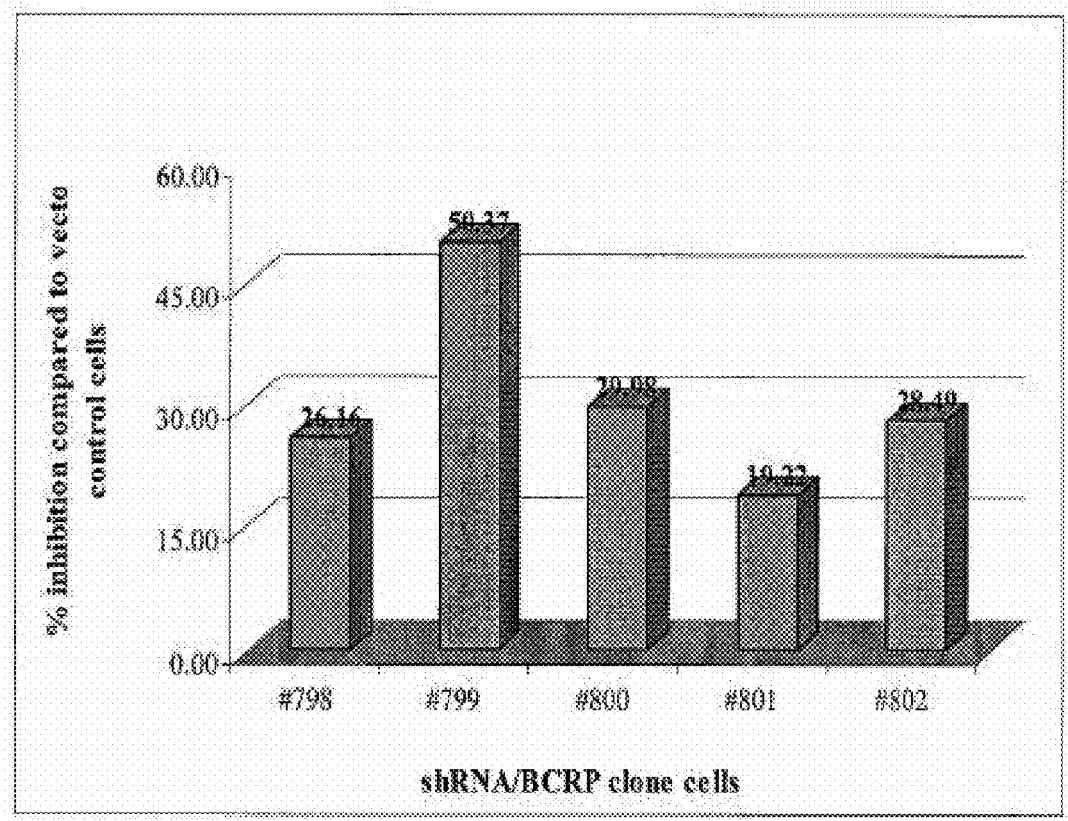
FIG. 11 shows percent inhibition of BCRP protein expression in shRNA/BCRP clone cells #798, 799, 800, 801, and 802 (as shown in FIG. 10). The ratio of optical densities for P-gp and beta-actin bands shown in FIG. 10 was used to determine percent inhibition of BCRP protein expression in shRNA/BCRP clone cells relative to expression levels in C2BBe1 cells transduced with a control lentivirus containing non-interfering shRNA.

For Western blotting, whole cell lysates were collected, the protein content quantified, and then 40 μg of protein was loaded and separated on an 8% Precise® SDS-PAGE protein gel. After separation, proteins were transferred to a PVDF membrane and immunoblotted. The primary BCRP antibody was a 1:200 dilution of mouse anti-BCRP (Sigma Cat #B7059, Lot #086K177). PVDF membranes were incubated with the primary antibody overnight at 4° C. After immunoblotting, membranes were exposed to a 1:15,000 dilution of goat anti-mouse HRP-conjugated antibody (Zymax Cat# 81-6520, Lot #50899722) for 1 hour at room temperature. Staining was visualized by the addition of a chemiluminescent horseradish peroxidase substrate, using a luminometer. Western blot analysis indicated a decrease in the amount of BCRP present in the shRNA/BCRP clone cells as compared to C2BBe1 vector control (VC) cells (FIGS. 10 and 11).

Figure 12:
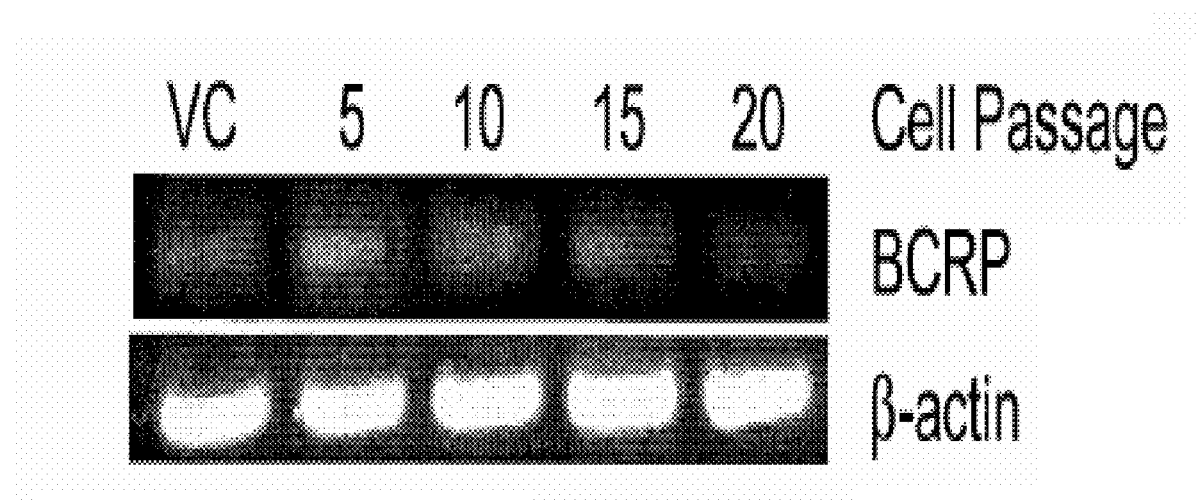
FIG. 12 shows expression of BCRP mRNA in shRNA/BCRP clone cell line #801 from cell passages 5 to 20 as measured by RT-PCR. Expression of BCRP mRNA decreased from passage 5 to passage 20. Amplified mRNAs were separated and visualized as described in Example 1. β-actin was included to account for varying efficiencies of total RNA extraction from the cell extracts.

RNA production in shRNA/BCRP clone #801 cells was also examined by RT-PCR to determine whether inhibition of BCRP mRNA was stable (FIG. 12). The results indicate that mRNA knockdown steadily increased between passages 5 and 20.

2. Functional Characterization of BCRP in Knockdown Clone Cells.

Each of the five shRNA/BCRP knockdown clone cells were seeded on transwells for three weeks for the transport assay. E3S (Estrone-3-sulfate) a BCRP substrate, was used for the permeability assay assessing BCRP function in shRNA/BCRP clone cells. Clones 798, 799, 800, and 802 were assayed after 9 passages. Clone 801 was found to grow somewhat faster, so was passaged 13 times prior to the transport assay while waiting for the other clones to grow. Bidirectional transport experiments were the same as described in Example 1 and were conducted using a the QC solution of Example 1 containing 10 μM E3S in addition to 10 μM digoxin, 10 μM propranolol and 10 μM atenolol, for 2 hours. Result indicated that the efflux ratio of Papp for E3S was significantly reduced (from 0.91 to 14.42) compared to control cells, which suggests that BCRP activity was inhibited in shRNA/BCRP clone cells (Table 7). Clone #801 showed the highest inhibition for BCRP function in E3S transport (96.43%).

TABLE 7

Transport of E3S (Estrone-3-sulfate) in shRNA/BCRP clone cells. Papp values are in units of $10^{-6}$ cm/sec calculated as described in Example 1.

| shRNA/BCRP clone cells number | A-B | Efflux of E3S B-A | efflux ratio |
|---|---|---|---|
| #798 | 0.86 | 12.46 | 14.42 |
| #799 | 0.87 | 8.88 | 10.23 |
| #800 | 0.82 | 2.67 | 3.28 |
| #801 | 0.34 | 0.31 | 0.91 |
| #802 | 0.77 | 4.38 | 5.70 |
| Control cell | 0.39 | 10.09 | 25.87 |

Atenolol and propranolol (10 μM) were used as passively permeable reference standards for the permeability assay. The permeability assay was conducted on the same cell monolayers used for the assay of E3S efflux. Atenolol and propranolol Papp values were not obviously different from that observed for vector control cells (described in Example 7), implying that BCRP knockdown did not affect the transcellular passive diffusion pathway (Table 8). Atenolol Papp in clone #801 cells was much lower than vector control cells. TEER values, determined before the permeability assay, were also similar to control cells except clone #801 cells, which, unexpectedly, had a TEER value 5 to 10-fold higher.

TABLE 8

Efflux of reference compounds in cell monolayer of shRNA/BCRP clone cells. Papp values are in units of $10^{-6}$ cm/sec calculated as described in Example 1.

| shRNA/BCRP clone cells number | Atenolol (A-B) | Propranolol (A-B) | TEER (ohm/cm$^2$) |
|---|---|---|---|
| #798 | 0.22 | 22.68 | 189 |
| #799 | 0.21 | 19.76 | 173 |
| #800 | 0.18 | 24.27 | 172 |
| #801 | 0.08 | 25.26 | 3162 |
| #802 | 0.24 | 24.21 | 317 |
| Vector control | 0.20 | 19.50 | 477 |

3. Effect of BCRP Knockdown on Expression and Function of Other Transporters (MRP2 and P-gp)).

MRP2, P-gp and BCRP are very important transporters located on the cell surface of C2BBe1 cells. Expression and function of these transporters were studied in shRNA/BCRP clone cells.

3.1 Expression of mRNA of MRP2 and P-gp in shRNA/BCRP Clone Cells

Figure 13:
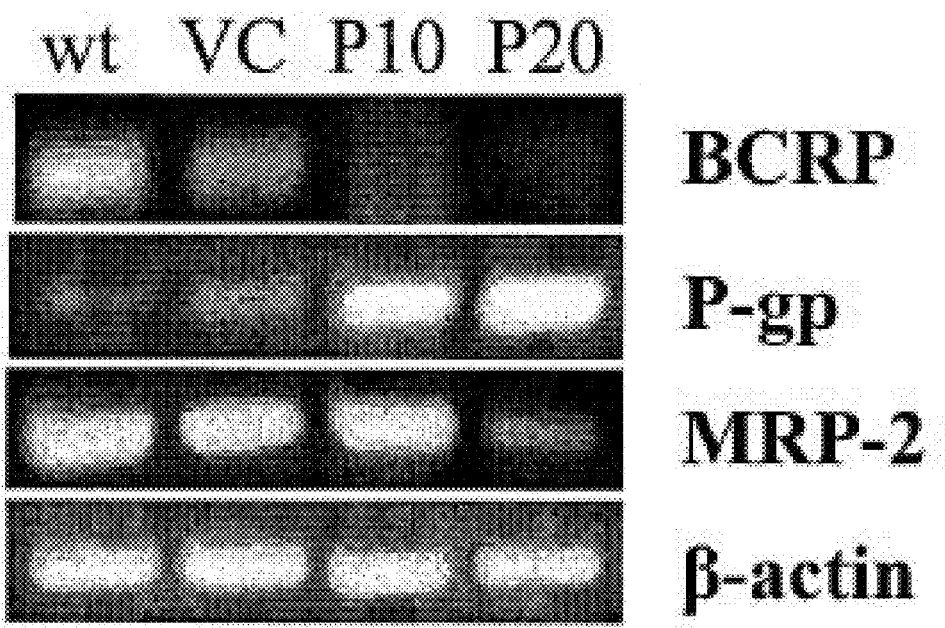
FIG. 13 shows expression of P-gp mRNA and MRP2 mRNA in shRNA/BCRP clone 801 at passages 10 and 20. Expression of P-gp mRNA in shRNA/BCRP clone 801 was increased compared to vector control cells (VC), non-transduced C2BBe1 (Wt) at both passages 10 and 20. In contrast to P-gp, MRP2 mRNA showed significantly decreased expression in clone #801 cells compared to the other cell lines tested only at passage 20. β-actin was included to account for varying efficiencies of total RNA extraction from the cell extracts.
Figure 14:
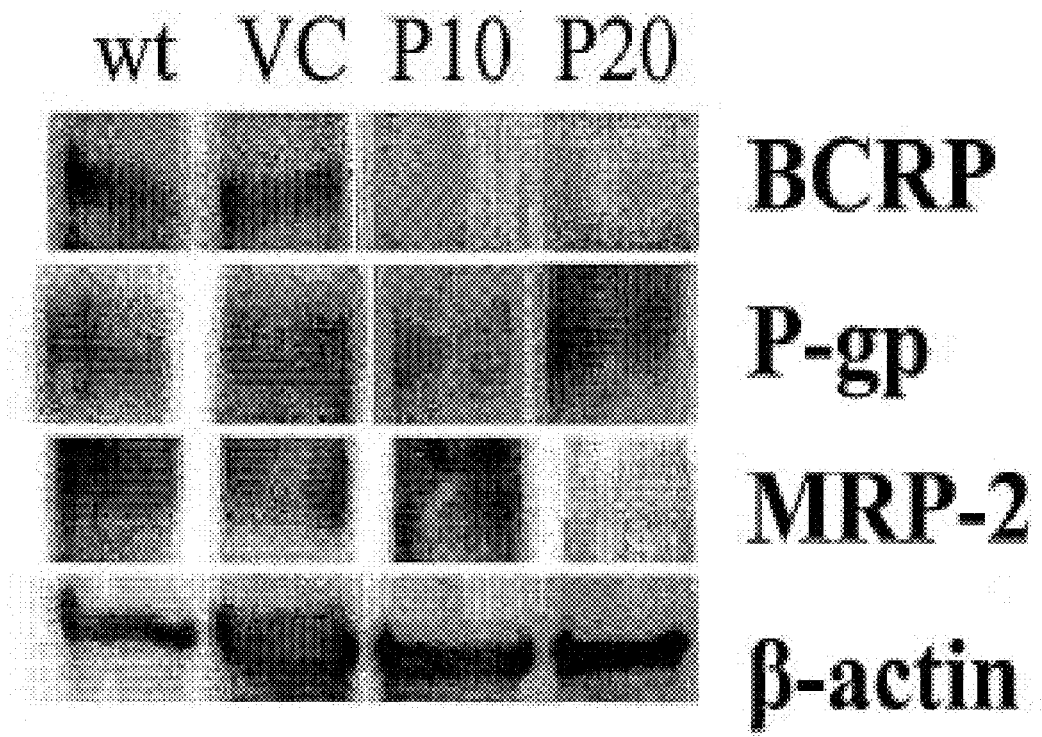
FIG. 14 shows the corresponding Western blot to FIG. 13 for the expression of BCRP, P-gp and MRP2 proteins in shRNA/BCRP clone cell line #801 for cell passages 10 and 20. The MRP2 band is present in shRNA/BCRP clone 801 passage 10, but not passage 20. The β-actin was included to account for variations in the amount of total protein applied to the electrophoresis gel.

To determine the effect of BCRP knockdown on expression of P-gp and MRP2, mRNA and protein levels were further studied in clone #801 cells and compared to clone #799 cells (see FIGS. 13 and 14). Results showed that P-gp mRNA levels appeared to be higher in clone #801 cells than in #799 and control cells. In contrast, MRP2 mRNA levels were reduced in clone #801 cells passaged 20 times (FIG. 13).

3.2 Functional Characterization of P-gp in shRNA/BCRP Clone Cells

Based on the P-gp mRNA expression profile results, P-gp function was examined in shRNA/BCRP clone cells by determining the digoxin efflux ratio across 21-day old monolayers plated into 12-well Transwell® transport plates. Experimental conditions were the same as those described in Example 1. The assay was carried out after each clone had been passaged 9 times. The digoxin efflux ratios were 72.67, 64.47 and 54.26 for clones #799, 800, 801 and parental cell monolayers, respectively, indicating higher efflux of this P-gp-specific substrate across monolayers of BCRP-knockdown cells. The results are presented in Table 9. The results suggest that P-gp function may be enhanced in shRNA/BCRP-clones #799, 800 and 801.

TABLE 9

Transport of digoxin by shRNA/BCRP clone cells

| shRNA/BCRP clone cells number | A-B | Efflux of digoxin B-A | efflux ratio |
|---|---|---|---|
| #798 | 0.33 | 7.12 | 21.43 |
| #799 | 0.11 | 8.11 | 72.67 |
| #800 | 0.06 | 3.76 | 64.47 |
| #801 | 0.05 | 2.69 | 54.26 |
| #802 | 0.22 | 3.44 | 15.77 |
| Control cell | 0.20 | 3.69 | 18.65 |

To confirm that P-gp activity was increased in shRNA/BCRP cells, as suggested by the results of the digoxin transport assay, the calcein-AM uptake assay described in Example 1 was repeated with shRNA/BCRP clone cells. Calcein-AM efflux is not mediated by BCRP. Therefore, any increase in calcein-AM uptake by the cells can be attributed to P-gp inhibition. The cells were plated in 96-well tissue culture plates and cultured for 48 hours. After 48 hours, cell culture media was removed and the cells were washed with phosphate buffered saline solution (PBS). After washing, cells were incubated with 1 µM calcein-AM for 30 minutes. Parental cells treated with Cyclosporin A, an established P-gp inhibitor, were used as a positive control to verify the P-gp inhibition increased the intracellular fluorescence in parental cell lines. After incubation with calcein-AM, the cells were rinsed with fresh control buffer and fluorescence was measured using a Fluo-star fluorescence plate reader (BMG Lab Technologies, NC) with excitation and emission filters set at wavelengths of 485 nm and 538 nm, respectively. The assay was carried out after each clone had been passaged 9 times. As shown in Table 10, clones #799, 800, 801 and 802 showed significant functional induction of P-gp activity that was comparable to vector control cells.

TABLE 10

Transport of calcein-AM by shRNA/BCRP cells

| shRNA/BCRP clone cell number | RFU/µg of protein | % decrease of Calcein-AM compared to vector control |
|---|---|---|
| #798 | 10.13 | 0.33 |
| #799 | 6.99 | 31.18 |
| #800 | 4.26 | 58.07 |
| #801 | 1.08 | 89.37 |
| #802 | 6.76 | 33.42 |
| vector control | 10.16 | |

Clone #801 showed the highest P-gp functional activity in the calcein-AM assay. A calcein-AM assay was conducted using shRNA/BCRP clone #801 cells from a higher cell passage, passage 20, to determine whether the P-gp inductive effect, suggested by the results in Table 10, persisted over numerous cell passages. Results showed that after cell passage 20 the activity of P-gp in #801 cells was increased up to 73% compared to vector control cells, results are normalized for total protein. (Table 11).

TABLE 11

Transport of calcein-AM by shRNA/BCRP clone #801 cells at passage 20

| Cell line/Passage # | Normalized Mean Fluorescence | SD | Normalized Mean Fluorescence in the Presence of CSA | SD | % Increase over Vector Control cells |
|---|---|---|---|---|---|
| 801/p20 | 5.08 | 0.50 | 72.31 | 1.51 | 72.65 |
| Vector Control cells | 23.92 | 4.38 | 62.86 | 4.34 | — |

4. Further Characterization of shRNA/BCRP Clone #801 Cells

While monitoring the growth rates of the various BCRP knockdown clones produced by lentiviral transduction, we noted that one clone, #801, started growing at an accelerated rate after being passaged about 15 times in vitro. Because the parental C2BBe1 cells take approximately 3 weeks to form monolayers suitable for drug transport assays, we investigated whether or not clone #801 would mature and form barrier properties suitable for drug transport assays sooner than the parental cell line and/or the vector control line.

4.1 Barrier Property of shRNA/BCRP Clone #801 Cells

First, TEER was determined for this cell line (Table 12) at various times after plating into Transwells®. Results showed TEER values were over 900 Ohm/cm² after 6 days, indicating that tight cell monolayers develop rapidly on Transwell® devices.

TABLE 12

TEER for shRNA/BCRP clone #801 cells as determined after 3, 6, 10, 15, 20 and 25 days of seeded on transwell.

| | Day after seeded on trasnwell | | | | | |
|---|---|---|---|---|---|---|
| | 3 | 6 | 10 | 15 | 20 | 25 |
| TEER (ohm/cm²) | 273 | 979 | 1383 | 1464 | 1934 | 2736 |

4.2 Transport of E3S, Digoxin and Permeability Reference Compounds in shRNA/BCRP Clone #801 Cells As noted, after cell passage 20 shRNA/BCRP clone #801 was found to grow faster and present TEER values much higher than the other four clones. In addition, RT-PCR results suggested that the expression of P-gp mRNA and protein was higher than in control cells (Table 9), Therefore, the transport of digoxin, which is a substrate of P-gp was conducted in the shRNA/BCRP clone #801 cell monolayers (see Table 13) to determine whether the apparent increase in P-gp mRNA levels was reflected in increased efflux transporter function. Transport of E3 S, passively absorbed reference compounds and TEER were also determined at same time.

As shown in Table 13, the digoxin efflux ratio for shRNA/BCRP clone #801 cell monolayers was higher than for the wild-type C2BBe1 control cells. Similar results were obtained using the calcein-AM assay (Table 12). The TEER values of clone #801 monolayers were about 5 times higher than those of the wild-type C2BBe1 control cells. The E3S efflux ratio in contrast was still suppressed relative to the parental cell lines indicating that BCRP functional knockdown persisted. The Papp values of the reference compound atenolol and propranolol were low and high, respectively, preserving the same rank order as in the wild-type C2BBe1 control cells.

TABLE 13

Transport of digoxin, E3S and reference compounds by shRNA/BCRP #801 clone cells 22 and 25 days after seeding on transwells

| | 22 day | | 25 day | |
|---|---|---|---|---|
| | Control wt C2BBe1 | KD #801 | Control wt C2BBe1 | KD #801 |
| ER of Digoxin | 18.65 | 54.26 | 15.38 | 42.46 |
| ER of E3S | 25.58 | 0.91 | 23.06 | 1.45 |
| TEER | 477 | 3162 | 490 | 2225 |
| Papp Atenolol A-B/×10⁶ cm/sec | 0.13 | 0.05 | 0.12 | 0.08 |
| Papp Propranolol A-B/×10⁶ cm/sec | 17.2 | 15.5 | 18.2 | 13.6 |

4.3 Stability of Expression and Function of P-gp and MRP2 in shRNA/BCRP Clone #801 Cells.

To determine the stability of the effect of BCRP knockdown on the expression of other transporter genes, mRNA levels of P-gp and MRP2 as well as protein levels were determined in shRNA/BCRP clone #801 cells from cell passage 10 to 20. The results indicated that expression of P-gp mRNA was increased and MRP2 was reduced at cell passage 20 (see FIGS. 13 and 14).

Bidirectional transport measurements of E3S, a BCRP substrate, and digoxin, a P-gp substrate as well as TEER measurements were conducted at same time in the same cell cultures. The digoxin efflux (see Table 14) was higher than vector control cell (25.13) in clone #801 cells from passage 18 to 25, and the highest efflux ratio was observed for cell passage 25 (114.98).

TABLE 14

Effect of BCRP knockdown on digoxin transport by shRNA/BCRP clone #801 cells at different cell passages.

| Cell passage | 9 | 18 | 25 | Vector control |
|---|---|---|---|---|
| Efflux ratio (Papp (B-A/A-B)) | 20.43 | 14.57 | 114.98 | 25.13 |
| TEER (ohm/cm$^2$) | 347 | 439 | 1589 | 296 |

The E3S efflux ratio (see Table 15) was kept below 3.0 from cell passage 9 to 25 in clone #801 cells compared to vector control cells (13.96). The TEER values of the clone #801 cell monolayers increased from 347 to 1589 ohms/cm$^2$ from cell passage 9 to 25, and was higher than vector control cells.

TABLE 15

Effect of BCRP knockdown on E3S transport by shRNA/BCRP clone #801 cells at different cell passages.

| Cell passage | 9 | 18 | 25 | Vector control |
|---|---|---|---|---|
| Efflux ratio (Papp (B-A/A-B)) | 0.59 | 1.54 | 0.52 | 13.96 |
| TEER (ohm/cm$^2$) | 347 | 565 | 1589 | 296 |

EXAMPLE 6

Evaluation of the Role of P-up, MRP2, and BCRP in Drug Absorption

The following prophetic example provides an experimental approach to determine the identity of a transporter(s) responsible for handling a drug of interest within the gastrointestinal tract of animals. This experimental approach comprises a combination of (a) cell lines (e.g., MDCK) expressing single (transfected) transporters, (b) C2BBe1 cells with selectively knocked-down transporters and (c) chemical inhibitors of transporters. Together, these tools will facilitate the determination of the identity of the transporters involved in a drug transport process with a high degree of certainty.

Experiment 1. Efflux transporter(s) involvement. In this experiment, bidirectional transport of a test compound can be screened in C2BBe1 WT monolayers, and the PappB-A/PappA-B ratio (i.e., efflux ratio, ER) can be calculated. Based on the results of these experiments, subsequent tests, as described below, can be carried out.

There are at least two possible outcomes for this experimental approach. In the first possible outcome, an ER<3 indicates that permeation does not involve membrane efflux transport proteins. Under this scenario, no additional testing for transporters would be required, except for possible confirmatory experiments. In the second possible outcome, an ER≧3 indicates that permeation involves at least one membrane efflux transport protein present in C2BBe1 cells (e.g., P-gp, MRP2 or BCRP). To identify which of these transporter(s) is involved in the efflux, the following experiments will be performed.

Experiment 2. Confirmation of P-gp involvement. To determine if P-pg plays a role in handling the drug of interest, bidirectional permeation experiments, as described and exemplified herein, can be carried out. Such bidirectional permeation experiments will be used to screen the following permutations: (a) test compound alone in C2BBe1 WT monolayers; (b) test compound alone in C2BBe1 P-gp-knockdown monolayers; (c) test compound with MRP inhibitor (e.g., MK571) in C2BBe1 P-gp-knockdown monolayers; (d) test compound with BCRP inhibitor (e.g., FTC) in C2BBe1 P-gp-knockdown monolayers; (e) test compound alone in MDR1-MDCK monolayers; and, (f) test compound with a P-gp inhibitor (e.g., CsA) in MDR1-MDCK monolayers Experiment 3. Confirmation of BCRP involvement. To determine if BCRP plays a role in handling the drug of interest, bidirectional permeation experiments, as described and exemplified herein, can be carried out. Such bidirectional permeation experiments will be used to screen the following permutations: (a) test compound alone in C2BBe1 WT monolayers; (b) test compound alone in C2BBe1 BCRP-knockdown monolayers; (c) test compound alone in BCRP-MDCK monolayers; and, (d) test compound with BCRP inhibitor (e.g., FTC) in BCRP-MDCK monolayers.

Experiment 4. Confirmation of MRP2 involvement. To determine if MRP2 plays a role in handling the drug of interest, bidirectional permeation experiments, as described and exemplified herein, can be carried out. Such bidirectional permeation experiments will be used to screen the following permutations: (a) test compound alone in C2BBe1 WT monolayers; (b) test compound alone in C2BBe1 MRP2-knockdown monolayers; (c) test compound alone in MRP2-MDCK monolayers; and, (d) test compound with MRP2 inhibitor (e.g., MK571) in MRP2-MDCK monolayers The following is an example of the approaches described above using two cell lines to identify whether or not compounds are substrates for P-gp or BCRP or both. Each compound was assayed in a bidirectional cell monolayer assay as described in Example 1. Concentrations of the selected compounds were determined by LC/MS/MS, as described in Example 1, by monitoring the mass transitions recorded in column 2 of Table 16. The cell monolayers consisted either of the parental C2BBe1 cells or shRNA/BCRP clone #801 cells that express only P-gp to a significant extent.

TABLE 16

Comparison of the bidirectional efflux ratios of selected P-gp substrates and non-substrates across monolayers of shRNA/BCRP clone #801 cells or parental C2BBe1 cells.

| Compound | Mass Transition | Efflux Ratio in KD Clone 801 cells | Efflux Ratio in C2BBe1 cells | P-gp Substrate? |
|---|---|---|---|---|
| Antipyrine | 189.20/56.10 | 0.92 | 0.84 | No |
| Etoposide | 589.30/229.00 | 11.53 | 13.67 | Yes |

TABLE 16-continued

Comparison of the bidirectional efflux ratios of selected P-gp substrates and non-substrates across monolayers of shRNA/BCRP clone #801 cells or parental C2BBe1 cells.

| Compound | Mass Transition | Efflux Ratio in KD Clone 801 cells | Efflux Ratio in C2BBe1 cells | P-gp Substrate? |
|---|---|---|---|---|
| Sulfasalazine | 329.00/284.90 | 0.22 | 15.45 | No |
| Furosemide | 329.00/284.90 | 1.38 | 21.76 | No |
| Diphenhydramine | 256.30/167.10 | 1.64 | 2.41 | No |
| Desipramine | 267.20/72.00 | 6.84 | 5.59 | Yes |

Antipyrine is not a substrate for P-gp because it does not show efflux in either cell line. Etoposide is a substrate because it shows efflux in both cell lines to a similar extent. Sulfasalazine is not a P-gp substrate because it is not effluxed by the shRNA/BCRP clone#801 cells even though it is effluxed by the C2BBe1 cells. This result suggests that sulfasalazine is a substrate for either BCRP and/or MRP2 which are expressed at high levels in the C2BBe1 cells, but not in shRNA/BCRP clone #801 cells. In fact, sulfasalazine is known to be a BCRP substrate (Table 1). In fact, the efflux ratio of sulfasalazine in the shRNA/BCRP clone #801 cells is 0.22, suggesting that these cells possess an uptake transporter for this compound whose activity is revealed by BCRP knockdown. Furosemide shows a similar pattern to sulfasalazine, but without evidence of the presence of an uptake transporter. Diphenhydramine is not highly effluxed by either cell line, while desipramine is, indicating that desipramine is a P-gp substrate. These results could be extended and confirmed by repeating the above study using shRNA/P-gp clones #83 or #85 and demonstrating that the efflux of the putative P-gp substrate is much lower across monolayers of the P-gp knockdown cells, while sulasalazine and furosemide still show high efflux.

EXAMPLE 7

Transduction of shRNA of Non-Target shRNA Control Transduction Particles in C2BBe1 Cells In some cases, parental C2BBe1 cells may not be appropriate positive controls for studying transport function of the knockdown cell lines, because of differences in media composition, growth rates and other possible effects produced by the presence of lentiviral gene products in the cells. When conducting experiments using shRNA clone cells, proper controls are a key element of experimental design to permit accurate interpretation of knockdown results and provide assurance of the specificity of responses observed. MISSION® non-target shRNA control vector containing SEQ ID NO: 27 available from Sigma-Aldrich, St. Louis, Mo., is a useful negative control that will activate the RISC and the RNAi pathway, but does not target any human genes.

Non-target shRNA MISSION® shRNA Lentiviral Transduction Particles (cat. no. SHC002V) were obtained from Sigma-Aldrich, St. Louis, Mo. and used to generate C2BBe1 cell lines transduced with non-target shRNA. Lentiviruses containing the non-target shRNA were used to transform C2BBe1 cells according to the manufacturer's protocols. In brief, C2BBe1 cells were seeded into a 96 well plate at 1.6× $10^4$ cells per well in cell culture media (90% DMEM+10% FBS), and incubated at 37° C. for 24 hours prior to transduction. On the day of transduction, media was removed from the wells and lentiviral particles were added to the wells at 0.5, 1.0, or 5.0 MOI (multiplicity of infection) and incubated with the cells for 24 hours at 37° C. Media containing unbound lentiviral particles was removed after this incubation, and fresh media was supplied. At 48 hours post-transduction, selective medium containing 10 Mg/mL puromycin was added and changed every 3-4 days thereafter to select for transduced cells. Positive cells were prepared as individual cell clones, then grown and evaluated in the various functional assays described herein. Clones shown to express P-gp, BCRP and MRP2 at levels similar or identical to that in the parental cell lines as well as possessing similar passive permeability properties were used as positive controls in some of the experiments described in Examples 4 and 5.

Experimental Results of Testing Control Cells:

C2BBe1 cells were transformed with a shRNA lentiviral vector containing SEQ ID NO. 27 as described in Example 2. To determine the optimal degree of multiplicity of infection (MOI), three MOIs were used to transduce the cells (0.5, 1.0 and 5.0). The molecular and functional assays were done as describe in Examples 3 to 5 for the same assays in gene knockdown cells. Expression of BCRP, MRP2 and P-gp in shRNA vector control cells was examined by RT-PCR and Western blot, which were conducted by the same methods used to examine knockdown cells. The results indicate that the vector control cells still express the transporter mRNAs (Table 17).

TABLE 17

Expression of BCRP, MRP2 and P-gp mRNA in shRNA vector control (VC) cells.

| Cell Group | MOI | Ratio of trasnporter/B-actin | | |
|---|---|---|---|---|
| | | P-gp | BCRP | MRP-2 |
| C2B Bel | — | 0.62 | 0.70 | 1.54 |
| Vector control | 0.5 | 0.66 | 0.73 | 1.53 |
| | 1.0 | 0.97 | 0.78 | 2.04 |
| | 5.0 | 0.85 | 0.66 | 1.74 |

Comparison of Typical Transport Properties Between shRNA Vector Control and Parental C2BBe1 Cells.

Vector control and C2BBe1 cell lines were cultured on 12-well Transwell® plates for 21 days prior to conducting the transport assays indicated in Table 18. The assays were performed under conditions described in Example 1. The results indicate that the vector control cells form monolayers on Transwell® devices with barrier properties suitable for in vitro drug transport assays and that they express efflux activity against digoxin, a P-gp substrate, and estrone-3-sulfate, a BCRP substrate (Table 18).

TABLE 18

Comparison of typical transport properties between shRNA vector control (MOI = 1) and parental C2BBe1 cell.

| Papp & Substrate | shRNA vector control | Parental C2BBe1 |
|---|---|---|
| Papp A-B (E3S) (×$10^6$ cm/sec) | 0.74 | 0.63 |
| Papp B-A (×$10^6$ cm/sec) | 10.36 | 10.69 |
| Ratio of Papp(B-A/A-B) | 14 | 17 |
| Papp A-B (Digoxin) (×$10^6$ cm/sec) | 0.33 | 0.2 |
| Papp B-A (×$10^6$ cm/sec) | 8.24 | 3.69 |
| Ratio of Papp(B-A/A-B) | 25 | 19 |
| Papp A-B (Atenolol) (×$10^6$ cm/sec) | 0.39 | 0.35 |
| Papp A-B (Propranolol) (×$10^6$ cm/sec) | 13.88 | 22.4 |
| TEER (ohms · cm$^2$) | 446 | 477 |

The present invention is not limited to the embodiments described and exemplified above, but is capable of variation and modification within the scope of the appended claims.

What is claimed:

1. A host cell transformed with a vector comprising a nucleic acid sequence encoding a nucleic acid molecule for inhibiting expression of p-glycoprotein, wherein the nucleic acid sequence comprises SEQ ID NO: 1, 2, 3, 4, or 5.

2. The host cell of claim 1, wherein the cell expresses p-glycoprotein.

3. The host cell of claim 1, wherein the cell is an intestinal epithelial cell.

4. A cell culture comprising the host cell of claim 3.

5. The host cell of claim 1, wherein said host cell has been deposited with the American Type Culture Collection and assigned accession number PTA-8752 or PTA-8753.

6. The host cell of claim 1, wherein the cell is a Caco-2 cell.

7. The host cell of claim 1, wherein the cell is derived from a Caco-2 cell.

8. The host cell of claim 1, wherein the cell is a C2BBe1 cell.

9. A kit for determining the absorption characteristics of a chemical compound, comprising the cell of claim 1.

10. A nucleic acid sequence comprising SEQ ID NO: 1, 2, 3, 4, or 5.

11. A nucleic acid encoded by the nucleic acid sequence of claim 10.

12. A vector comprising a nucleic acid sequence encoding a nucleic acid molecule for inhibiting expression of p-glycoprotein, wherein the nucleic acid sequence comprises SEQ ID NO: 1, 2, 3, 4, or 5.

* * * * *